United States Patent
Tanimoto et al.

(10) Patent No.: US 8,163,759 B2
(45) Date of Patent: *Apr. 24, 2012

(54) PYRAZOLO[1,5-A] PYRIMIDINE COMPOUNDS AS CB1 RECEPTOR ANTAGONIST

(75) Inventors: Koichi Tanimoto, Osaka (JP); Mariko Oi, Osaka (JP); Yasunori Tsuboi, Osaka (JP); Yasunori Moritani, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 503 days.

This patent is subject to a terminal disclaimer.

(21) Appl. No.: 12/303,177

(22) PCT Filed: Jul. 4, 2007

(86) PCT No.: PCT/JP2007/063762
§ 371 (c)(1),
(2), (4) Date: Dec. 2, 2008

(87) PCT Pub. No.: WO2008/004698
PCT Pub. Date: Jan. 10, 2008

(65) Prior Publication Data
US 2009/0258867 A1   Oct. 15, 2009

Related U.S. Application Data

(60) Provisional application No. 60/819,388, filed on Jul. 10, 2006.

(30) Foreign Application Priority Data

Jul. 5, 2006 (JP) ................. 2006-185036
Jan. 19, 2007 (JP) ................. 2007-009706
Mar. 9, 2007 (JP) ................. 2007-059332
Apr. 20, 2007 (JP) ................. 2007-111340

(51) Int. Cl.
*A01N 43/90* (2006.01)
*A61K 31/519* (2006.01)
*C07D 487/00* (2006.01)

(52) U.S. Cl. ................. 514/259.3; 544/281

(58) Field of Classification Search .......... None
See application file for complete search history.

(56) References Cited

U.S. PATENT DOCUMENTS

2005/0187224 A1  8/2005  Gebauer et al.
2009/0069298 A1* 3/2009  Moritani et al. ......... 514/217.06

FOREIGN PATENT DOCUMENTS

JP    2006-285609 A     10/2006
WO    WO-03/101993 A1   12/2003
WO    WO03101993    *  12/2003

(Continued)

OTHER PUBLICATIONS

Colombo et al., "Appetite Suppression and Weight Loss after the Cannabinoid Antagonist SR 141716," Life Sciences, vol. 63, No. 8, pp. 113-117, 1998.

(Continued)

*Primary Examiner* — Jeffrey Murray
(74) *Attorney, Agent, or Firm* — Birch, Stewart, Kolasch & Birch, LLP

(57) ABSTRACT

The present invention provides a pyrazolo[1,5-a]pyrimidine compound, having CB1 receptor-antagonizing activity, of the following formula [I]: in which $R^1$ and $R^2$ are the same or different and each an optionally substituted aryl group etc, $R^0$ is hydrogen atom, an alkyl group etc, E is a group of the formula: —C(=O)— or —SO$_2$—, R is a group of the following formula [i], [ii]or [iii] etc: Ring A is (a) a $C_{3-8}$ cycloalkyl group optionally fused to a benzene ring or (b) a benzene ring, Q is a single bond or a methylene group, Ring B is a 4- to 7-membered aliphatic heterocyclic group, said cyclic group binding via its ring-carbon atom to the adjacent nitrogen atom, X is sulfur atom etc, $R^3$ is an alkyl group optionally substituted by an alkylthio group, $R^4$ is hydrogen atom, an alkyl group etc, one of $R^A$ and $R^B$ is an alkyl group etc, and the other is hydrogen atom, an alkyl group etc, or a pharmaceutically acceptable salt thereof.

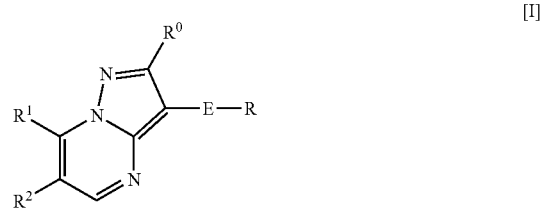

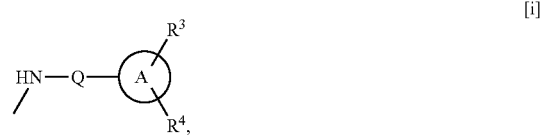

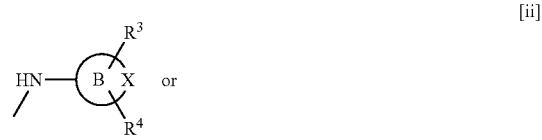

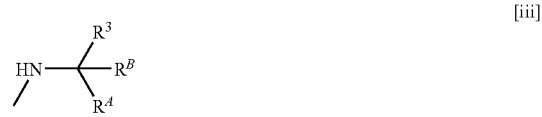

30 Claims, No Drawings

FOREIGN PATENT DOCUMENTS

| WO | WO-2004/069838 | A1 | 8/2004 |
| WO | WO 2004/094417 | A1 | 11/2004 |
| WO | WO 2004/106341 | A1 | 12/2004 |
| WO | WO 2005/018645 | A1 | 3/2005 |
| WO | WO-2005/061507 | A1 | 7/2005 |
| WO | WO 2005/082907 | A2 | 9/2005 |
| WO | WO-2005/103052 | A1 | 11/2005 |
| WO | WO 2006/016715 | A1 | 2/2006 |
| WO | WO 2006/072828 | A1 | 7/2006 |
| WO | WO-2007/046548 | A1 | 4/2007 |

OTHER PUBLICATIONS

Lange et al., "Synthesis, Biological Properties, and Molecular Modeling Investigations of Novel 3, 4-Diarylpyrazolines as Potent and Selective CB-Cannabinoid Receptor Antagonists," Journal of Medicinal Chemistry, vol. 47, No. 3, pp. 627-643, 2003.

Matsuda et al., "Structure of a Cannabinoid receptor and functional expression of the cloned cDNA," Nature, vol. 346, pp. 561-564, 1990.

Munro et al., "Molecular characterization of a peripheral receptor for cannabinoids," Nature, vol. 365, pp. 61-65, 1993.

Office Action for corresponding U.S. Appl. No. 12/083,268 dated Aug. 19, 2010.

Office Action for corresponding U.S. Appl. No. 12/083,268 dated Jun. 29, 2010.

Office Action for corresponding U.S. Appl. No. 12/083,268 dated Mar. 3, 2011.

Office Action dated Jul. 26, 2011 for Japanese Application No. 2007-175769.

* cited by examiner

PYRAZOLO[1,5-A] PYRIMIDINE COMPOUNDS AS CB1 RECEPTOR ANTAGONIST

This application is the National Phase of PCT/JP2007/063762 filed on Jul. 4, 2007, which claims priority under 35 U.S.C. 119(e) to U.S. Provisional Application No. 60/819,388 filed on Jul. 10, 2006 and under 35 U.S.C. 119(a) to Patent Application Nos. 2006-185036, 2007-009706, 2007-059332 and 2007-111340 filed in JAPAN on Jul. 5, 2006, Jan. 19, 2007, Mar. 9, 2007 and Apr. 20, 2007, respectively. All of which are hereby expressly incorporated by reference into the present application.

TECHNICAL FIELD

The present invention relates to a novel pyrazolo[1,5-a] pyrimidine compound or a pharmaceutically acceptable salt thereof which has potent central cannabinoid receptor (CB1) antagonizing activity and hence is useful as a medicine.

BACKGROUND ART

It is well known that, by intake of marijuana, various psychiatric or neurological reactions such as confusion of temporal or space sense, euphoria, alteration of memories, analgesia, hallucination and the like would be produced. The compounds generally referred to as "cannabinoid" including delta 9-tetrahydro-cannabinol (delta 9-THC) are responsible for many of such reactions. The effect of cannabinoid is considered to be produced by an interaction between the compound and its endogenous specific/high-affinity receptors. Two subtypes of cannabinoid receptors (CB1 and CB2) have been identified and cloned. The CB1 receptor is distributed in central nervous system (CNS) regions including brain (Nature, Vol. 346, 1990, pp 561-564) while the CB2 receptor is distributed in immune system including spleen (Nature, Vol. 365, 1993, pp 61-65).

Substances having affinity to such cannabinoid receptors (agonists, antagonists or inverse agonists) may produce various pharmacological effects like marijuana. In particular, substances having affinity to central CB1 receptor may be useful for treatment of a CNS disease such as a psychotic disorder, a neurological disorder and the like.

There have been known various compounds, including pyrazol-3-carboxamide compounds such as SR141716 (Life Science, Vol. 63, 1998, PL113-117), 4,5-dihydro-pyrazole compounds such as SLV-319 (Journal of Medicinal Chemistry, Vol. 47(3), 2004, p. 627-643), dihydropyrazolo[3,4-c]pyridin-7-one compounds, 2H-pyrazolo[4,3-d]-pyrimidin-7(6H)-one compounds (WO2004/094417), 1-[2- and/or 3-(substituted aryl)-pyrazolo[1,5-a]pyrimidin-7-yl]piperidine compounds (WO2004/069838) and the like as the substances having affinity to such cannabinoid receptors. Meanwhile, the present applicant filed a patent application directing to pyrazolo[1,5-a]pyrimidine-3-carboxamide or sulfonamide compounds (WO2007/046548). Among them, at least SR141716 and SLV-319 are under clinical studies on the efficacy thereof as anorexigenics (anti-obesity agent).

DISCLOSURE OF INVENTION

The object of the present invention is to provide a novel pyrazolo[1,5-a]-pyrimidine compound which has a potent CB1 receptor-antagonizing activity and hence is useful as a medicine.

The present invention relates to a novel pyrazolo[1,5-a] pyrimidine compound of the formula [I]:

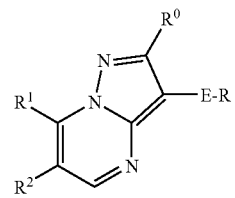

[I]

wherein
$R^1$ and $R^2$ are the same or different and each an optionally substituted aryl group or an optionally substituted saturated or unsaturated heterocyclic group,
$R^0$ is (a) hydrogen atom; (b) an alkyl group optionally substituted by one to three halogen atom(s); (c) an alkyloxyalkyl group; (d) a group of the formula: —CON($R^e$)($R^f$); (e) an aminoalkyl group, the amino moiety of said group being optionally substituted by one to two alkyl group(s); (f) an amino group optionally substituted by a group selected from an alkyl group, an alkylcarbonyl group and an alkylsulfonyl group; (g) a 4- to 6-membered nitrogen-containing aliphatic heterocyclic group; (h) a group of the formula: —$SO_2N(R^{01})(R^{02})$; (i) a group of the formula: —NHCONHR$^{03}$; (j) an alkyloxy group optionally substituted by hydroxyl group; (k) a hydroxyalkyl group; or (l) carboxyl group, $R^e$ and $R^f$ are the same or different and each a hydrogen atom, an alkyl group or a dialkylamino group, $R^{01}$ and $R^{02}$ are the same or different and each hydrogen atom, an alkyl group or a carbamoylalkyl group, $R^{03}$ is a hydrogen atom or an alkyl group,
E is a group of the formula: —C(=O)— or —$SO_2$—,
R is A) a group of the following formula [i], [ii] or [iii]:

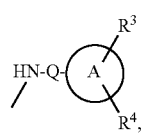

[i]

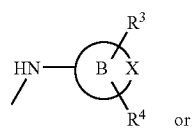

[ii]

or

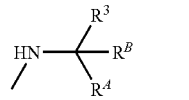

[iii]

when $R^0$ is (a) hydrogen atom; (b) an alkyl group optionally substituted by one to three halogen atom(s); (c) an alkyloxyalkyl group; (e) an aminoalkyl group, the amino moiety of said group being optionally substituted by one to two alkyl group(s); (f) an amino group optionally substituted by a group selected from an alkyl group, an alkylcarbonyl group and an alkylsulfonyl group; (g) a 4- to 6-membered nitrogen-containing aliphatic heterocyclic group; or (j) an alkyloxy group optionally substituted by hydroxyl group and B) (a) an alkyloxy group or (b) a group of the formula: —N($R^5$)($R^6$) when $R^0$ is a group of the formula: —$SO_2N(R^{01})(R^{02})$; a group of the formula: —NHCONHR$^{03}$, a group of the formula: —CON($R^e$)($R^f$); carboxyl group or a hydroxyalkyl group, Ring A is (a) a $C_{3-8}$ cycloalkyl group optionally fused to a benzene ring or (b) a benzene ring, Q is a single bond or methylene group, Ring B is a 4- to 7-membered aliphatic heterocyclic group, said cyclic group binding via its ring-carbon atom to the adjacent nitrogen atom, X is sulfur atom, a group of the formula: —SO—, a group of the formula: —SO$_2$—, oxygen atom or a group of the formula: —NR$^k$—, R$^k$ is an alkyl group, an alkylcarbonyl group, an alkyloxycarbonyl group, an alkylsulfonyl group, an aminosulfonyl group optionally substituted by one or two alkyl group(s), or a carbamoyl group optionally substituted by one or two alkyl group(s), R$^3$ is (a) an alkyl group optionally substituted by a group selected from hydroxyl group, amino group, an acylamino group, a dialkylcarbamoyl-amino group, an alkylsulfonyl-amino group and a dialkylsulfamoyl-amino group; (b) cyano group; (c) carboxyl group; (d) an alkyloxycarbonyl group; (e) a group of the formula: —N(R$^a$)(R$^b$); (f) a group of the formula: —CON(R$^a$)(R$^b$); (g) a group of the formula:

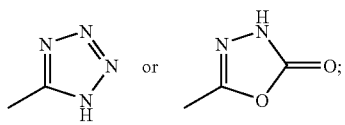

or (h) hydroxyl group, R$^a$ and R$^b$ are the same or different and each hydrogen atom, hydroxyl group, cyano group, an alkyl group, a cyanoalkyl group; a trihalogenoalkyl group, a hydroxyalkyl group, an alkyloxyalkyl group, a cycloalkyl group, an acyl group, an alkylsulfonyl group or an aminoalkyl group (the amino moiety of said group being optionally substituted by one or two alkyl group(s)), or both R$^a$ and R$^b$ combine each other at their termini together with the adjacent nitrogen atom to form a saturated or unsaturated nitrogen-containing heterocyclic group optionally containing a heteroatom(s), other than the nitrogen atom, selected from sulfur atom and oxygen atom, R$^4$ is (a) hydrogen atom; (b) an alkyl group; (c) cyano group; (d) carboxyl group; (e) an alkylcarbonyl group; (f) an alkyloxycarbonyl group; (g) a group of the formula: —CON(R$^c$)(R$^d$); (h) phenyl group; (i) benzyl group; or (j) an acylamino group, R$^c$ and R$^d$ are the same or different and each hydrogen atom or an alkyl group, one of R$^A$ and R$^B$ is (a) an alkyl group optionally substituted by hydroxyl group, an alkyloxy group, amino group, an alkylamino group or a dialkylamino group; (b) a phenyl group substituted by one to two group(s) selected from a halogen atom, an alkyloxy group and a trihalogenoalkyl group; (c) benzyl group; (d) a heteroaryl group; or (e) a cycloalkyl group and the other is (a) hydrogen atom; or (b) an alkyl group optionally substituted by hydroxyl group, an alkyloxy group, amino group, an alkylamino group or a dialkylamino group, R$^5$ and R$^6$ are as follows:

A) one of R$^5$ and R$^6$ is hydrogen atom or an alkyl group and the other is (a) an alkyl group optionally substituted by one to three group(s) selected from a halogen atom, hydroxyl group, cyano group, an alkyloxy group, a cycloalkyl group, an amino group optionally substituted by one or two alkyl group(s), an alkylthio group, an alkylsulfinyl group, an alkylsulfonyl group, an acyl group, an optionally substituted aryl group and an optionally substituted saturated or unsaturated heterocyclic group; (b) an optionally substituted cycloalkyl group; (c) a group of the formula: —N(R$^8$)(R$^9$); (d) an optionally substituted aryl group; or (e) an optionally substituted saturated or unsaturated heterocyclic group, or B) both R$^5$ and R$^6$ combine each other at their termini together with the adjacent nitrogen atom to form a saturated or unsaturated nitrogen-containing heterocyclic group, one of R$^8$ and R$^9$ is hydrogen atom or an alkyl group and the other is (a) an alkyl group optionally substituted by one to three groups selected from a halogen atom, cyano group and an aryl group; (b) an optionally substituted cycloalkyl group; (c) an optionally substituted aryl group; (d) an acyl group; or (e) an optionally substituted saturated or unsaturated heterocyclic group, excluding 6-phenyl-7-(4-chlorophenyl)-3-(N-isopropylcarbamoyl)-pyrazolo[1,5-a]pyrimidine; 6-(2-chlorophenyl)-7-(4-chloro-phenyl)-3-(N-isopropylcarbamoyl) pyrazolo[1,5-a]pyrimidine; 6-(2-chlorophenyl)-7-(4-chlorophenyl)-3-[N-(4-cyano-4-tetrahydrothiopyranyl) carbamoyl]pyrazolo[1,5-a]pyrimidine; 6-(2-chlorophenyl)-7-(4-chlorophenyl)-3-[N-(α-dimethylbenzyl)carbamoyl]-pyrazolo[1,5-a]pyrimidine; 6-(2-chlorophenyl)-7-(4-chlorophenyl)-3-[N-(α-methyl-benzyl)-carbamoyl]pyrazolo [1,5-a]pyrimidine; 6-(2-chlorophenyl)-7-(4-chlorophenyl)-3-[N-[1-(2-pyridyl)ethyl]carbamoyl]-pyrazolo[1,5-a] pyrimidine; 6-(2-chlorophenyl)-7-(4-trifluoromethylphenyl)-3-[N-[1-(2-pyridyl)ethyl] carbamoyl]-pyrazolo[1,5-a]pyrimidine; 6-(2-chlorophenyl)-7-(4-chlorophenyl)-3-[N-(4-cyanobenzyl)carbamoyl] pyrazolo[1,5-a]pyrimidine; and 6-(2-chlorophenyl)-7-(4-chlorophenyl)-3-[N-(1,1-dioxotetrahydro-thien-3-yl) carbamoyl]pyrazolo[1,5-a]pyrimidine, or a pharmaceutically acceptable salt thereof.

BEST MODE TO CARRY OUT INVENTION

The present invention includes as one embodiment a compound of the formula [I-I]:

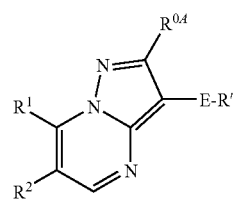

[I-I]

wherein

R$^{0A}$ is (a) hydrogen atom; (b) an alkyl group optionally substituted by one to three halogen atom(s); (c) an alkyloxyalkyl group; (d) an aminoalkyl group, the amino moiety of said group being optionally substituted by one to two alkyl group(s); (e) an amino group optionally substituted by a group selected from an alkyl group, an alkylcarbonyl group and an alkylsulfonyl group; (f) a 4- to 6-membered nitrogen-containing aliphatic heterocyclic group; or (g) an alkyloxy group optionally substituted by a hydroxyl group, R' is a group of the following formula [i], [ii] or [iii]:

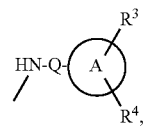

[i]

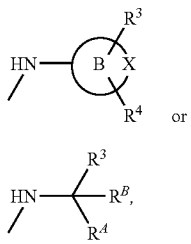

and the other symbols are the same as defined above, excluding 6-phenyl-7-(4-chlorophenyl)-3-(N-isopropylcarbamoyl)pyrazolo[1,5-a]pyrimidine; 6-(2-chlorophenyl)-7-(4-chlorophenyl)-3-(N-isopropylcarbamoyl)-pyrazolo[1,5-a]pyrimidine; 6-(2-chlorophenyl)-7-(4-chlorophenyl)-3-[N-(4-cyano-4-tetrahydrothiopyranyl)-carbamoyl]pyrazolo[1,5-a]pyrimidine; 6-(2-chlorophenyl)-7-(4-chlorophenyl)-3-[N-(α-dimethylbenzyl)carbamoyl]-pyrazolo[1,5-a]pyrimidine; 6-(2-chlorophenyl)-7-(4-chlorophenyl)-3-[N-(α-methylbenzyl)carbamoyl]pyrazolo[1,5-a]pyrimidine; 6-(2-chlorophenyl)-7-(4-chlorophenyl)-3-[N-[1-(2-pyridyl)ethyl]carbamoyl]pyrazolo[1,5-a]pyrimidine; 6-(2-chlorophenyl)-7-(4-trifluoromethylphenyl)-3-[N-[1-(2-pyridyl)ethyl]carbamoyl]pyrazolo[1,5-a]pyrimidine; and 6-(2-chlorophenyl)-7-(4-chlorophenyl)-3-[N-(4-cyanobenzyl)-carbamoyl]pyrazolo[1,5-a]pyrimidine,
or a pharmaceutically acceptable salt thereof.

Besides, the present invention also includes as another embodiment a compound of the formula [I-II]:

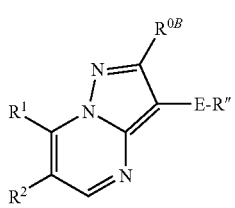

wherein $R^{OB}$ is a group of the formula: —$SO_2N(R^{O1})(R^{O2})$; a group of the formula: —$NHCONHR^{O3}$; a group of the formula: —$CON(R^e)(R^f)$; carboxyl group; or a hydroxyalkyl group, $R^{O1}$ and $R^{O2}$ are the same or different and each hydrogen atom, an alkyl group or a carbamoylalkyl group, $R^{O3}$ is hydrogen atom or an alkyl group, $R^e$ and $R^f$ are the same or different and each hydrogen atom, an alkyl group or a dialkylamino group, R″ is an alkyloxy group or a group of the formula: —$N(R^5)(R^6)$, and the other symbols are the same as defined above, excluding 6-(2-chlorophenyl)-7-(4-chloro-phenyl)-3-[N-(1,1-dioxotetrahydrothien-3-yl)-carbamoyl]-2-(hydroxymethyl)pyrazolo[1,5-a]pyrimidine, or a pharmaceutically acceptable salt thereof.

In case that $R^1$ and/or $R^2$ in the compounds [I] of the present invention is an aryl group, examples of said aryl group include a 6- to 10-membered monocyclic or bicyclic aryl group such as phenyl group or a naphthyl group, among them, phenyl group is preferred.

In case that $R^1$ and/or $R^2$ in the compounds [I] of the present invention is a saturated or unsaturated heterocyclic group, examples of said heterocyclic group include a saturated or unsaturated 5- to 7-membered heteromonocyclic group containing one to three heteroatom(s) selected from sulfur atom, oxygen atom and nitrogen atom. More concrete examples of said heterocyclic group may be a 5- to 6-membered oxygen-containing heterocyclic group such as a furyl group, a tetrahydrofuranyl group, a pyranyl group or a tetrahydropyranyl group, a 5- to 6-membered sulfur-containing heterocyclic group such as a thienyl group, a tetrahydrothienyl group, a thiopyranyl group or a tetrahydrothiopyranyl group or a 5- to 7-membered nitrogen-containing heterocyclic group such as a pyrrolidinyl group, an imidazolyl group, a pyrazolyl group, an oxazolyl group, an isoxazolyl group, a thiazolyl group, an isothiazolyl group, a pyridyl group, a piperidyl group, a pyrimidinyl group, a pyrazinyl group, a pyridazinyl group, a morpholinyl group, a thiomorpholinyl group or an azacycloheptyl group. Among them, a 5- to 6-membered sulfur- or nitrogen-containing heteromonocyclic group such as a thienyl group, a pyrrolidinyl group, a piperidyl group or a pyridyl group is preferred.

The aryl group in $R^1$ and/or $R^2$ may be substituted by the same or different one to three group(s) selected from a halogen atom, cyano group, an alkyl group optionally substituted by one to three halogen atom(s), an alkyloxy group optionally substituted by one to three halogen atom(s), an amino group optionally substituted by one to two alkyl group(s), an alkylthio group, an alkylsulfinyl group and an alkylsulfonyl group.

The saturated or unsaturated heterocyclic group in $R^1$ and/or $R^2$ may be substituted by the same or different one to three group(s) selected from a halogen atom, cyano group, oxo group, an alkyl group optionally substituted by one to three halogen atom(s), an alkyloxyalkyl group, an alkyloxy group optionally substituted by one to three halogen atom(s), an alkyloxyalkyloxy group, an amino group optionally substituted by one to two alkyl group(s), an alkylthio group, an alkylsulfinyl group and an alkylsulfonyl group.

In case that $R^0$ or $R^{OA}$ in the compound [I] of the present invention is a 4- to 6-membered nitrogen-containing aliphatic heterocyclic group, examples of said aliphatic heterocyclic group include an azetidyl group, a pyrrolidinyl group, an imidazolidinyl group, a piperidyl group, a piperazinyl group and a morpholinyl group.

Examples of the saturated or unsaturated nitrogen-containing heterocyclic group in $R^3$ [a group of the formula: —$N(R^a)(R^b)$ or a group of the formula: —$CON(R^a)(R^b)$] include a saturated or unsaturated 5- to 6-membered nitrogen-containing heteromonocyclic group such as a pyrrolyl group, a pyrrolidinyl group, a piperidino group, a piperazino group, a morpholino group or a thiomorpholino group. Among them, a pyrrolidinyl group or a morpholino group is preferred.

In case that $R^A$ or $R^B$ is a heteroaryl group, examples of such heteroaryl group include a 5- to 6-membered nitrogen-containing monocyclic heteroaryl group such as a pyridyl group.

In case that $R^5$, $R^6$, $R^8$ or $R^9$ in the compound [I] is a cycloalkyl group, said cycloalkyl group may be substituted by one to two group(s) selected from (a) cyano group, (b) an alkyl group, (c) carboxyl group, (d) an alkyloxycarbonyl group, (e) an amino group optionally substituted by one or two alkyl group(s) and (f) a carbamoyl group optionally substituted by one or two alkyl group(s).

Examples of the aryl group in $R^5$, $R^6$, $R^8$ or $R^9$ include a 6- to 10-membered monocyclic or bicyclic aryl group such as phenyl group or a naphthyl group, among them, phenyl group is preferred. Said aryl group may be substituted by one or two halogen atom(s).

In case that $R^5$, $R^6$, $R^8$ or $R^9$ is a saturated or unsaturated heterocyclic group, examples of the heterocyclic group include (a) a saturated or unsaturated, 4- to 7-membered heteromonocyclic group, said heteromonocyclic group containing one to four heteroatom(s) selected from oxygen atom, sulfur atom and nitrogen atom; (b) a saturated or unsaturated, 8- to 15-membered nitrogen-containing bicyclic or tricyclic heterocyclic group formed by fusing the aforementioned heteromonocyclic group with one or two other cyclic group(s) selected from a $C_{3-8}$ cycloalkyl group, a 5- to 6-membered monocyclic aryl group and a saturated or unsaturated, 4- to 7-membered heteromonocyclic group, said heteromonocyclic group containing one to four heteroatom(s) selected from oxygen atom, sulfur atom and nitrogen atom; and (c) a saturated or unsaturated, 8- to 11-membered nitrogen-containing spiro-heterocyclic group.

Examples of the saturated or unsaturated heterocyclic group in $R^5$, $R^6$, $R^8$ or $R^9$ include:

(A) a saturated or unsaturated oxygen- or sulfur-containing heterocyclic group selected from a furyl group, a tetrahydrofuranyl group, a pyranyl group, a tetrahydro-pyranyl group, a thiacyclobutyl group, a thienyl group, a tetrahydrothienyl group, a thiopyranyl group, a tetrahydrothiopyranyl group, a benzofuranyl group, a dihydro-benzofuranyl group, an isobenzofuranyl group, a chromanyl group, an isochromanyl group, a chromenyl group, an isochromenyl group, a benzothienyl group and a dihydro-benzothienyl group; or (B) a saturated or unsaturated nitrogen-containing heterocyclic group selected from an azetidyl group, a pyrrolidinyl group, a pyrrolinyl group, an imidazolidinyl group, an imidazolinyl group, a pyrazolidinyl group, a pyrazolinyl group, a pyrrolyl group, a 2H-pyrrolyl group, an imidazolyl group, a pyrazolyl group, a dihydropyrazolyl group, a thiazolidinyl group, a thiazolyl group, an isothiazolyl group, an isoxazolyl group, an oxazolidinyl group, a pyridyl group, a dihydropyridyl group, a tetrahydropyridyl group, a piperidyl group, a pyrazinyl group, a piperazinyl group, a pyrimidinyl group, a tetrahydropyrimidinyl group, a pyridazinyl group, a morpholinyl group, an azocinyl group, an azacycloheptyl group, an indolizinyl group, a benzimidazolyl group, a benzotriazolyl group, an indolyl group, an isoindolyl group, a 3H-indolyl group, an indolinyl group, an isoindolinyl group, a 1H-indazolyl group, a pyrrolopyridyl group, a pyrrolopyrimidinyl group, a tetrazolyl group, a purinyl group, a pteridinyl group, a 4H-quinolizinyl group, a quinolyl group, a dihydroquinolyl group, a tetrahydroquinolyl group, an isoquinolyl group, a dihydroisoquinolyl group, a tetrahydroisoquinolyl group, a phthalazinyl group, a dihydrophthalazinyl group, a naphthyridinyl group, a dihydronaphthyridinyl group, a tetrahydronaphthyridinyl group, a quinoxalinyl group, a quinazolinyl group, a dihydrobenzothiazinyl group, a dihydrobenzoxazinyl group, a cinnolinyl group, a pteridinyl group, a xanthenyl group, a carbazolyl group, a beta-carbolinyl group, a phenanthridinyl group, an acridinyl group, a 5H-dihydro-dibenzazepinyl group and a spiro-heterocyclic group of the formula:

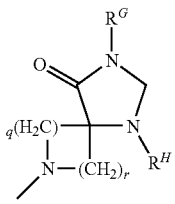

wherein $R^G$ and $R^H$ are the same or different and each a hydrogen atom or an alkyl group, and q and r are an integer of 1 or 2.

Among the saturated or unsaturated heterocyclic group in $R^5$, $R^6$, $R^8$ or $R^9$, examples of the preferred heterocyclic group include a tetrahydrofuranyl group, a pyrrolyl group, a pyrrolidinyl group, a piperidyl group, an azacycloheptyl group, a tetrahydropyranyl group, a piperazinyl group, a morpholinyl group, a thiomorpholinyl group, a thiacyclobutyl group, a tetrahydrothienyl group, a tetrahydrothiopyranyl group, a thiazolyl group, a pyridyl group, a pyrimidinyl group, an indolinyl group, a pyrrolopyridyl group or a tetrahydronaphthyridinyl group, Examples of the saturated or unsaturated heterocyclic group formed by combining $R^5$ with $R^6$ include (a) a saturated or unsaturated, 4- to 7-membered hetero-monocyclic group, said heteromonocyclic group optionally containing two or more nitrogen atoms and one to two heteroatom(s) other than the nitrogen atom selected from oxygen atom and sulfur atom; (b) a saturated or unsaturated, 8- to 15-membered nitrogen-containing bicyclic or tricyclic heterocyclic group formed by fusing the aforementioned heteromonocyclic group with one or two other cyclic group(s) selected from a $C_{3-8}$ cycloalkyl group, a 5- to 6-membered monocyclic aryl group and a saturated or unsaturated, 4- to 7-membered heteromonocyclic group, said heteromonocyclic group containing one to four heteroatom(s) selected from oxygen atom, sulfur atom and nitrogen atom; and (c) a saturated or unsaturated, 8- to 11-membered nitrogen-containing spiro-heterocyclic group.

Examples of the above-mentioned saturated or unsaturated nitrogen-containing heterocyclic group formed by combining $R^5$ with $R^6$ is a saturated or unsaturated nitrogen-containing heterocyclic group selected from an azetidyl group, a pyrrolidinyl group, a pyrrolinyl group, an imidazolidinyl group, an imidazolinyl group, a pyrazolidinyl group, a pyrazolinyl group, a pyrrolyl group, an imidazolyl group, a pyrazolyl group, a dihydropyrazolyl group, a thiazolidinyl group, an oxazolidinyl group, a dihydropyridyl group, a tetrahydropyridyl group, a piperidyl group, a piperazinyl group, a tetrahydropyrimidinyl group, a morpholinyl group, an azacycloheptyl group, a benzimidazolyl group, a benzotriazolyl group, an indolyl group, an isoindolyl group, an indolinyl group, an isoindolinyl group, a 1H-indazolyl group, a tetrazolyl group, a purinyl group, a dihydroquinolyl group, a tetrahydroquinolyl group, a dihydro-isoquinolyl group, a tetrahydroisoquinolyl group, a dihydrophthalazinyl group, a dihydroquinazolinyl group, a dihydrobenzothiazinyl group, a dihydrobenzoxazinyl group, a carbazolyl group, a beta-carbolinyl group, a 5H-dihydro-dibenzazepinyl group and a spiro-heterocyclic group of the formula:

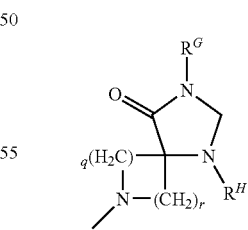

wherein $R^G$ and $R^H$ are the same or different and each a hydrogen atom or an alkyl group, and q and r are an integer of 1 or 2. Among them, the preferred examples of said saturated or unsaturated nitrogen-containing heterocyclic group include a saturated or unsaturated 5- to 7-membered nitrogen-containing heterocyclic group such as morpholino group, thiomorpholino group, piperidino group, piperazino group or an azacycloheptyl group.

Further, the saturated or unsaturated heterocyclic group in $R^5$, $R^6$, $R^8$ or $R^9$ or the heterocyclic group formed by combining $R^5$ with $R^6$ may be substituted by the same or different one to four group(s) selected from a halogen atom, hydroxyl group, cyano group, oxo group, an alkyl group, an alkyl group substituted by one to three halogen atom(s), an alkyloxyalkyl group, an aminoalkyl group, a cycloalkyl group, an arylalkyl group, an alkyloxy group, an alkyloxy group substituted by one to three halogen atom(s), an acyl group, an amino group optionally substituted by one to two alkyl group(s), an acylamino group, an alkylsulfonyl group, an aminosulfonyl group optionally substituted by one to two alkyl group(s), an aryl group optionally substituted by one to two halogen atom(s) and a saturated or unsaturated 5- to 6-membered nitrogen-containing heterocyclic group.

The acyl group in $R^3$, $R^4$, $R^5$, $R^6$, $R^8$ or $R^9$ may be an acyl group of the formula: $R^XCO-$ which is formed by removing one hydroxyl group from a carboxylic acid of the following formula:

$$R^X\text{—COOH} \qquad [Ac-1]$$

wherein $R^X$ is (a) hydrogen atom, (b) an alkyl group optionally substituted by one to three group(s) selected from a halogen atom, cyano group, an alkylsulfonyl group and a pyridyl group, (c) an alkyloxy group optionally substituted by an aryl group, (d) a cycloalkyl group, (e) an aryl group optionally substituted by one to two group(s) selected from a halogen atom, cyano group, an alkyl group, a trihalogenoalkyl group and an alkyloxy group, (f) an amino group optionally substituted by one or two alkyl group(s) or (g) a saturated or unsaturated 5- to 7-membered heterocyclic group optionally substituted by one to two group(s) selected from a halogen atom, cyano group, an alkyl group and a trihalogenoalkyl group. Examples of said acyl group include (a1) formyl group, (b1) a $C_{1-6}$ alkyl-carbonyl group such as acetyl group or propionyl group, a trihalogeno-$C_{1-6}$ alkyl-carbonyl group such as trifluoroacetyl group, a cyano-$C_{1-6}$ alkyl-carbonyl group such as cyanoacetyl group or a pyridyl-$C_{1-6}$ alkyl-carbonyl group such as a pyridylacetyl group, (cl) a $C_{1-6}$ alkyloxy-carbonyl such as methoxycarbonyl group, ethoxycarbonyl group or tert-butoxycarbonyl group or an aryl-$C_{1-6}$ alkyloxy-carbonyl group such as benzyloxycarbonyl group, (dl) a $C_{3-8}$ cycloalkyl-carbonyl group such as cyclopropylcarbonyl group or cyclopentylcarbonyl group, (e1) an aryl-carbonyl group such as benzoyl group, a mono- or di-halogenoaryl-carbonyl group such as a chlorobenzoyl group, a fluorobenzoyl group or a difluoro-benzoyl group, a cyanoaryl-carbonyl group such as a cyanobenzoyl group, a trihalogeno-$C_{1-6}$ alkyl-aryl-carbonyl group such as a trifluoromethylbenzoyl group or a $C_{1-6}$ alkyloxy-aryl-carbonyl group such as a methoxybenzoyl group, (f1) carbamoyl group, a N—$C_{1-6}$ alkyl-carbamoyl group, or (g1) a 5- to 6-membered heteroaryl-carbonyl group (the heteroaryl moiety of said group being optionally substituted by one to two group(s) selected from a halogen atom, cyano group, an alkyl group and a trihalogenoalkyl group) such as a furoyl group, a thenoyl group, a bromothenoyl group, a cyanothenoyl group, a pyridylcarbonyl group, a chloropyridylcarbonyl group, a cyanopyridylcarbonyl group, a trifluoromethylpyridylcarbonyl group or a pyrazinyl-carbonyl group.

The present invention includes as a more concrete embodiment a compound of the formula [I-I-A]:

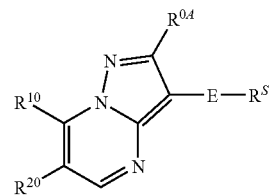

wherein $R^{10}$ and $R^{20}$ are the same or different and each (i) a 6- to 10-membered monocyclic or bicyclic aryl group optionally substituted by one to three group(s) selected from a halogen atom, cyano group, an alkyl group optionally substituted by one to three halogen atom(s), an alkyloxy group optionally substituted by one to three halogen atom(s), an amino group optionally substituted by one to two alkyl group(s), an alkylthio group, an alkylsulfinyl group and an alkylsulfonyl group, or (ii) a 4- to 7-membered saturated or unsaturated, sulfur-, oxygen- or nitrogen-containing hetero-monocyclic group optionally substituted by one to three group(s) selected from a halogen atom, cyano group, oxo group, an alkyl group optionally substituted by one to three halogen atom(s), an alkyloxy group optionally substituted by one to three halogen atom(s), an amino group optionally substituted by one to two alkyl group(s), an alkylthio group, an alkylsulfinyl group and an alkylsulfonyl group, $R^S$ is a group of the following formula [i-a], [ii-a] or [iii-a]:

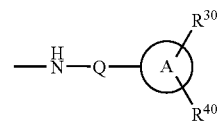

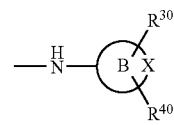

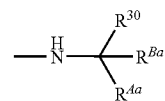

$R^{30}$ is (a) an alkyl group optionally substituted by a group selected from hydroxyl group, amino group, an acylamino group, a dialkylcarbamoyl-amino group, an alkylsulfonylamino group and a dialkylsulfamoyl-amino group; (b) cyano group; (c) carboxyl group; (d) an alkyloxycarbonyl group; (e) a group of the formula: —N($R^{aa}$)($R^{bb}$); (f) a group of the formula: —CON($R^{aa}$)($R^{bb}$); (g) a group of the formula:

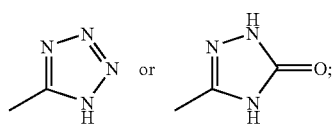

or (h) hydroxyl group, $R^{aa}$ and $R^{bb}$ are the same or different and each hydrogen atom, hydroxyl group, cyano group, an alkyl group, a cyanoalkyl group, a trihalogenoalkyl group, a hydroxyalkyl group, an alkyloxyalkyl group, a cycloalkyl group, a group of the formula: $R^{xa}CO—$, an alkylsulfonyl group or an aminoalkyl group optionally substituted by one or two alkyl group(s) at the amino moiety, or both $R^{aa}$ and $R^{bb}$ combine each other at their termini to form a saturated or unsaturated nitrogen-containing heterocyclic group, said heterocyclic group optionally further containing other heteroatom(s) than the nitrogen atom(s) selected from oxygen atom and sulfur atom, $R^{xa}$ is (a) hydrogen atom, (b) an alkyl group optionally substituted by one to three group(s) selected from a halogen atom, cyano group, an alkylsulfonyl group and a pyridyl group, (c) an alkyl oxy group optionally substituted by a 6- to 10-membered monocyclic or bicyclic aryl group, (d) a cycloalkyl group, (e) a 6- to 10-membered monocyclic or bicyclic aryl group optionally substituted by one to two group(s) selected from a halogen atom, cyano group, an alkyl group, a trihalogenoalkyl group and an alkyloxy group, (f) an amino group optionally substituted by one or two alkyl group(s) or (g) a saturated or unsaturated 4- to 7-membered sulfur-, oxygen- or nitrogen-containing heteromonocyclic group optionally substituted by one to two group(s) selected from a halogen atom, cyano group, an alkyl group and a trihalogenoalkyl group, $R^{40}$ is (a) hydrogen atom; (b) an alkyl group; (c) cyano group; (d) carboxyl group; (e) an alkylcarbonyl group; (f) an alkyloxycarbonyl group; (g) a group of the formula: —CON($R^{cc}$)($R^{dd}$); (h) phenyl group; (i) benzyl group; or (j) a group of the formula: $R^{xa}CONH—$, $R^{cc}$ and $R^{dd}$ are the same or different and each hydrogen atom or an alkyl group, one of $R^{Aa}$ and $R^{Bb}$ is (a) an alkyl group optionally substituted by hydroxyl group, an alkyloxy group, amino group, an alkylamino group or a dialkylamino group; (b) a phenyl group optionally substituted by one to two group(s) selected from a halogen atom, an alkyloxy group and a trihalogenoalkyl group; (c) benzyl group; (d) a 5- to 6-membered nitrogen-containing heteroaryl group; or (e) a cycloalkyl group and the other is (a) hydrogen atom or (b) an alkyl group optionally substituted by hydroxyl group, an alkyloxy group, amino group, an alkylamino group or a dialkylamino group and the other symbols are the same as defined above, excluding 6-(2-chlorophenyl)-7-(4-chlorophenyl)-3-[N-(4-cyanobenzyl)-carbamoyl]pyrazolo[1,5-a]pyrimidine; 6-(2-chlorophenyl)-7-(4-chlorophenyl)-3-[N-(4-cyano-4-tetrahydrothiopyranyl)carbamoyl]pyrazolo[1,5-a]pyrimidine; 6-phenyl-7-(4-chlorophenyl)-3-(N-isopropylcarbamoyl)-pyrazolo[1,5-a]pyrimidine; 6-(2-chloro-phenyl)-7-(4-chlorophenyl)-3-(N-isopropylcarbamoyl)pyrazolo[1,5-a]pyrimidine; 6-(2-chlorophenyl)-7-(4-chlorophenyl)-3-[N-(α-dimethylbenzyl)carbamoyl]pyrazolo[1,5-a]pyrimidine; 6-(2-chlorophenyl)-7-(4-chlorophenyl)-3-[N-(α-methylbenzyl)-carbamoyl]pyrazolo[1,5-a]pyrimidine; 6-(2-chlorophenyl)-7-(4-chlorophenyl)-3-[N-[1-(2-pyridyl)ethyl]carbamoyl]-pyrazolo[1,5-a]pyrimidine; 6-(2-chlorophenyl)-7-(4-trifluoromethylphenyl)-3-[N-[1-(2-pyridyl)ethyl] carbamoyl]-pyrazolo[1,5-a]pyrimidine; and 6-(2-chlorophenyl)-7-(4-chlorophenyl)-3-[N-(4-cyanobenzyl) carbamoyl]pyrazolo[1,5-a]pyrimidine, or a pharmaceutically acceptable salt thereof.

The above mentioned compound [I-I-A] of the present invention includes as a further concrete embodiment, a compound of the following formula [I-I-a]:

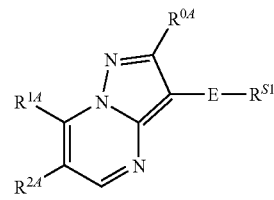

wherein $R^{1A}$ is (a) a phenyl group optionally substituted by one to two group(s) selected from a halogen atom, a difluoroalkyl group, a trifluoroalkyl group and a dialkylamino group or (b) a saturated or unsaturated 5- to 6-membered nitrogen-containing hetero-cyclic group optionally substituted by a group selected from an alkyl group, a trifluoro-alkyl group and an alkyloxy group, $R^{2A}$ is a phenyl group optionally substituted by one to two group(s) selected from a halogen atom and cyano group, $R^{S1}$ is a group of the following formula [i-b], [i-c], [i-d], [ii-b], [iii-b] or [iii-c]:

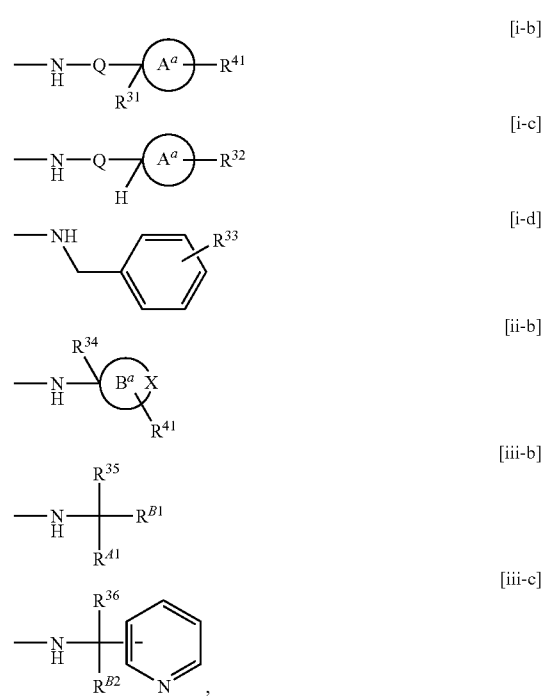

Ring $A^a$ is (a) a $C_{3-8}$ cycloalkyl group or (b) a $C_{5-6}$ cycloalkyl fused to a benzene ring, Q is a single bond or methylene group, Ring $B^a$ is a 4- to 7-membered aliphatic heteromonocyclic group binding via its ring carbon atom to the adjacent nitrogen atom, $R^{31}$ is cyano group, an alkyl group, a hydroxyalkyl group, an aminoalkyl group optionally substituted by, at the amino moiety, an alkylcarbonyl group, dialkylsulfamoyl group, an alkylsulfonyl group or a dialkylcarbamoyl group at the amino moiety, a carboxyalkyl group, carboxyl group, an alkyloxycarbonyl group, a carbamoyl group optionally substituted by one to two group(s) selected from an alkyl group and a dialkylaminoalkyl group, or a group of the following formula:

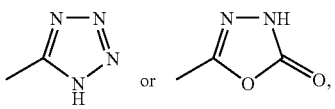 or $R^{41}$ is hydrogen atom, amino group or a group of the formula: $R^{xa}CONH-$ $R^{32}$ is hydroxyl group, carboxyl group, an alkyloxycarbonyl group, amino group or a group of the formula: $R^{xa}-CONH-$, $R^{33}$ is carboxyl group or an alkyloxycarbonyl group, $R^{34}$ is cyano group, an alkyl group, a hydroxyalkyl group, an aminoalkyl group, a carboxyalkyl group, carboxyl group, an alkyloxycarbonyl group, a carbamoyl group optionally substituted by one to two group(s) selected from an alkyl group, a hydroxyalkyl group, a cyanoalkyl group, a trihalogenoalkyl group, an alkyloxyalkyl group, a cycloalkyl group, an alkylsulfonyl group and a dialkylamino-alkyl group, a group of the formula:

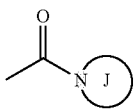

or a group of the following formula:

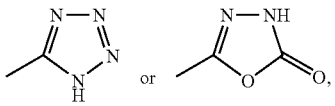

Ring J is a saturated or unsaturated nitrogen-containing 4- to 7-membered heteromonocyclic group optionally containing oxygen atom(s) as a heteroatom(s) other than the nitrogen atom, $R^{35}$ is a hydroxyalkyl group, carboxyl group, an alkyloxycarbonyl group or a carbamoyl group optionally substituted by one or two alkyl group(s), $R^{A1}$ is an alkyl group, a cycloalkyl group, a phenyl group optionally substituted by one to two group(s) selected from a halogen atom, an alkyloxy group and a trihalogenoalkyl group or benzyl group, $R^{B1}$ is hydrogen atom or an alkyl group, $R^{36}$ is an alkyl group or a carbamoyl group, $R^{B2}$ is hydrogen atom or an alkyl group, and the other symbols are the same as defined above, excluding 6-(2-chlorophenyl)-7-(4-chlorophenyl)-3-[N-(4-cyano-4-tetrahydrothiopyranyl)carbamoyl]pyrazolo[1,5-a]pyrimidine; 6-(2-chlorophenyl)-7-(4-chlorophenyl)-3-[N-[1-(2-pyridyl)-ethyl]carbamoyl]pyrazolo[1,5-a]pyrimidine; and 6-(2-chlorophenyl)-7-(4-trifluoromethylphenyl)-3-[N-[1-(2-pyridyl)ethyl]carbamoyl]pyrazolo[1,5-a]pyrimidine, or a pharmaceutically acceptable salt thereof.

The present invention includes as another more concrete embodiment (1) a compound of the following formula [I-II-i]:

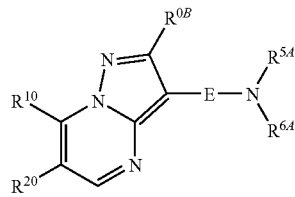

[I-II-i]

wherein $R^{5A}$ is hydrogen atom or an alkyl group, $R^{6A}$ is (A) an alkyl group optionally substituted by one to three group(s) selected from (a) a halogen atom, (b) hydroxyl group, (c) cyano group, (d) an alkyloxy group, (e) carboxyl group, (f) a carbamoyl group optionally substituted by one or two alkyl group(s), (g) an alkylthio group, (h) an alkylsulfonyl group, (i) a cycloalkyl group optionally substituted by one to two group(s) selected from an alkyl group and hydroxyl group, (j) an amino group optionally substituted by one or two alkyl group(s) and (k) a saturated or unsaturated 4- to 10-membered monocyclic or bicyclic nitrogen-, sulfur- or oxygen-containing heterocyclic group; or (B) a cycloalkyl group optionally fused to a benzene ring and optionally substituted by one to two group(s) selected from (a) an alkyl group optionally substituted by hydroxyl group, carboxyl group and amino group; (b) cyano group; (c) carboxyl group; (d) a group of the formula: $R^{xa}CO-$; (e) a group of the formula: $-N(R^{a1})(R^{b1})$; (f) a group of the formula: $-CON(R^{a1})(R^{b1})$; (g) a 6- to 10-membered monocyclic or bicyclic aryl group; (h) an alkyl group substituted by a 6- to 10-membered monocyclic or bicyclic aryl group; and (i) a saturated or unsaturated 4- to 7-membered nitrogen-containing heteromonocyclic group optionally substituted by one or two oxo group(s), $R^{a1}$ and $R^{b1}$ are the same or different and each hydrogen atom, hydroxyl group, cyano group, an alkyl group, a group of the formula: $R^{xa}CO-$, an alkylsulfonyl group, an aminoalkyl group, a monoalkylamino-alkyl group or a dialkylamino-alkyl group; or (C) a 6- to 10-membered monocyclic or bicyclic aryl group optionally substituted by one to two group(s) selected from cyano group, a trihalogenoalkyl group, an alkyloxy group and carboxyl group; or (D) a saturated or unsaturated 4- to 10-membered nitrogen-containing monocyclic or bicyclic heterocyclic group containing at least one heteroatom selected from sulfur atom, oxygen atom and nitrogen atom and optionally substituted by one to four group(s) selected from (a) a halogen atom, (b) hydroxyl group, (c) oxo group, (d) cyano group, (e) an alkyl group, (f) a trihalogenoalkyl group, (g) a hydroxyalkyl group, (h) an alkyloxyalkyl group, (i) an alkyloxy group, (j) a group of the formula: $R^{xa}CO-$, (k) a cycloalkyl group, (l) an alkylsulfonyl group, (m) an aminosulfonyl group optionally substituted by one or two alkyl group(s), (n) phenylsulfonyl group, (o) amino group, (p) a group of the formula: $R^{xa}-CONH-$, (q) a carbamoyl group optionally substituted by one or two alkyl group(s), (r) a 6- to 10-membered monocyclic or bicyclic aryl group optionally substituted by a halogen atom(s), and (s) a saturated or unsaturated 4- to 7-membered sulfur-, oxygen- or nitrogen-containing heteromonocyclic group optionally substituted by one to two group(s) selected from an alkyl group and a trihalogenoalkyl group; or (E) a group of the formula: —N($R^{81}$)($R^{91}$), $R^{81}$ is hydrogen atom or an alkyl group, $R^{91}$ is (a) an alkyl group optionally substituted by one to three group(s) selected from a halogen atom, cyano group and a 6- to 10-membered monocyclic or bicyclic aryl group; (b) a cycloalkyl group; (c) a 6- to 10-membered monocyclic or bicyclic aryl group optionally substituted by a group selected from a halogen atom, cyano group, an alkyl group, a trihalogenoalkyl group, an alkyloxy group, a trihalogenoalkyloxy group, an alkylthio group, an alkylsulfonyl group and a group of the formula: $R^{xa}CO$—; (d) a group of the formula: $R^{xa}CO$—; or (e) a saturated or unsaturated 4- to 7-membered sulfur-, oxygen- or nitrogen-containing heteromonocyclic group optionally substituted by a group selected from a halogen atom, an alkyl group, a trihalogenoalkyl group and an alkyloxy group; or (F) both $R^{5A}$ and $R^{6A}$ combine each other together with the adjacent nitrogen atom to form a saturated or unsaturated 4- to 10-membered nitrogen-containing monocyclic or bicyclic heterocyclic group optionally containing one or two heteroatom(s) other than the nitrogen atom selected from sulfur atom and oxygen atom and optionally substituted by one or two group(s) selected from a halogen atom, oxo group, an alkyl group, a group of the formula: $R^{xa}CO$— and a dialkylamino-sulfonyl group, and the other symbols are the same as defined above, excluding 6-(2-chlorophenyl)-7-(4-chlorophenyl)-3-[N-(1,1-dioxotetrahydrothien-3-yl)carbamoyl-2-(hydroxymethyl)-pyrazolo[1,5-a]pyrimidine, or a pharmaceutically acceptable salt thereof, and (2) a compound of the following formula [I-II-ii]:

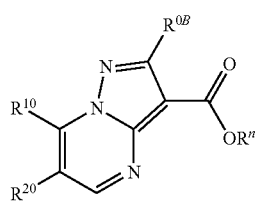

[I-II-ii]

wherein $R^n$ is an alkyl group and the other symbols are the same as defined above or a pharmaceutically acceptable salt thereof.

The present invention includes as another further concrete embodiment, (1) a compound [I-II-i] in which $R^{10}$ is (a) a phenyl group optionally substituted by one to two group(s) selected from a halogen atom, an alkyl group, a difluoroalkyl group, a trifluoroalkyl group and a dialkylamino group or (b) a saturated or unsaturated 5- to 6-membered nitrogen-containing heterocyclic group optionally substituted by a group selected from an alkyl group, a trifluoroalkyl group and an alkyloxy group, $R^{20}$ is a phenyl group optionally substituted by one to two group(s) selected from a halogen atom and cyano group, $R^{6A}$ is (A) an alkyl group optionally substituted by a group selected from one to three halogen atom(s), hydroxyl group, cyano group, carboxyl group and an alkyloxycarbonyl group; or (B) a group of the following formula:

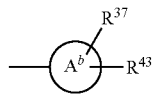

in which Ring $A^b$ is (a) a $C_{3-8}$ cycloalkyl group or (b) a $C_{3-8}$ cycloalkyl group fused to a benzene ring, $R^{37}$ is hydrogen atom, cyano group, an alkyl group, a hydroxyalkyl group, an aminoalkyl group, a carboxyalkyl group, carboxyl group, an alkyloxycarbonyl group, a carbamoyl group optionally substituted by one to two group(s) selected from an alkyl group and a dialkylamino-alkyl group, or a group of the following formula:

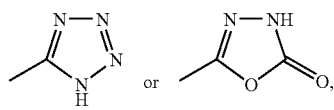

and $R^{43}$ is hydrogen atom, amino group, an alkyloxycarbonylamino group or benzyloxy-carbonyl group; or (C) a phenyl group optionally substituted by one to two group(s) selected from a halogen atom, an alkyloxy group, a trihalogenoalkyl group, carboxyl group and an alkyloxycarbonyl group; or (D) a cyclic group of the following formula:

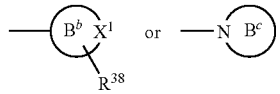

in which Ring $B^b$ is a 4- to 7-membered aliphatic heteromonocyclic group, said cyclic group binding via its ring-carbon atom to the adjacent nitrogen atom, Ring $B^c$ is a 4- to 7-membered nitrogen-containing aliphatic heteromonocyclic group, $X^1$ is sulfur atom, a group of the formula: —SO—, a group of the formula: —SO$_2$—, oxygen atom or a group of the formula: —N$R^m$—, $R^m$ is an alkyl group, an alkylcarbonyl group, an alkyloxycarbonyl group, an alkylsulfonyl group, an aminosulfonyl group optionally substituted by one or two alkyl group(s) or a carbamoyl group optionally substituted by one or two alkyl group(s), $R^{38}$ is hydrogen atom, cyano group, an alkyl group, a hydroxyalkyl group, an aminoalkyl group, a carboxyalkyl group, carboxyl group, an alkyloxycarbonyl group, a carbamoyl group optionally substituted by one to two group(s) selected from an alkyl group and a dialkylamino-alkyl group or a group of the following formula:

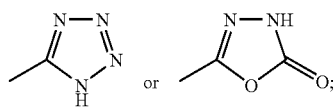

or (E) a group of the formula: —N($R^{8a}$)($R^{9a}$) in which $R^{8a}$ is hydrogen atom or an alkyl group, $R^{9a}$ is an alkyl group, a trihalogenoalkyl group, a cyanoalkyl group, benzyl group, a cycloalkyl group, a phenyl group optionally substituted by a group selected from a halogen atom, cyano group, an alkyl group, a trihalogenoalkyl group, an alkyloxy group, a trihalogenoalkyloxy group, an alkylthio group, an alkylsulfonyl group, an alkyloxycarbonyl group and benzyloxycarbonyl group, an alkyloxycarbonyl group, benzyloxycarbonyl group or a 5- to 6-membered nitrogen-containing heteroaryl group; or (F) a group of the following formula:

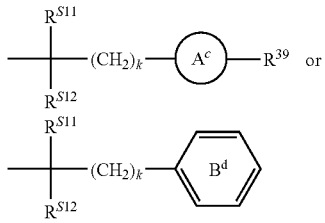

in which Ring $A^c$ is a $C_{3-8}$ cycloalkyl group optionally fused to a benzene ring, Ring $B^d$ is (a) a phenyl group optionally substituted by a halogen atom, a cyano group, an alkyloxy group, a trihalogenoalkyl group or a carboxyl group or (b) a pyridyl group, $R^{S11}$ is hydrogen atom or an alkyl group, $R^{S12}$ is hydrogen atom, an alkyl group, carboxyl group, carbamoyl group or a mono- or di-alkylcarbamoyl group, $R^{39}$ is hydrogen atom, a halogen atom, cyano group, an alkyl group, a hydroxyalkyl group, a trihalogenoalkyl group, an aminoalkyl group, an alkyloxy group, a carboxyalkyl group, carboxyl group, a carbamoyl group optionally substituted by one to two group(s) selected from an alkyl group and a dialkylaminoalkyl group, amino group, an alkyloxycarbonylamino group or benzyloxycarbonylamino group, and k is an integer of 0 to 2; and (2) a compound [I-II-ii] in which $R^{10}$ is (a) a phenyl group optionally substituted by one to two group(s) selected from a halogen atom, a difluoroalkyl group, a trifluoroalkyl group and a dialkylamino group or (b) a saturated or unsaturated 5- to 6-membered nitrogen-containing heterocyclic group optionally substituted by a group selected from an alkyl group, a trifluoroalkyl group and an alkyloxy group and $R^{20}$ is a phenyl group optionally substituted by one to two group(s) selected from a halogen atom and cyano group.

Among the compounds [I] of the present invention, examples of the preferred compound include a compound [I-I] in which $R^1$ and $R^2$ are the same or different and each (a) a phenyl group optionally substituted by one to three group(s) selected from a halogen atom, cyano group, an alkyl group optionally substituted by one to three halogen atom(s) and an amino group optionally substituted by one or two alkyl group(s) or (b) a saturated or unsaturated 5- to 7-membered nitrogen-containing heterocyclic group optionally substituted by a group selected from an alkyl group optionally substituted by one to three halogen atom(s) and an alkyloxy group, and A1) R' is a group of the formula [i], $R^3$ is (a) an alkyl group optionally substituted by a group selected from hydroxyl group and amino group, (b) cyano group, (c) carboxyl group, (d) an alkyloxycarbonyl group, (e) a group of the formula: —CON($R^e$)($R^f$) or (f) an acylamino group, $R^e$ and $R^f$ are the same or different and each hydrogen atom, an alkyl group or a dialkylaminoalkyl group, $R^4$ is hydrogen atom or an acylamino group; or A2) R' is a group of the formula [ii], X is sulfur atom, a group of the formula: —$SO_2$—, oxygen atom or a group of the formula: —$NR^k$—, $R^k$ is an alkyloxycarbonyl group, an alkylsulfonyl group, an alkylcarbonyl group or a dialkylaminosulfonyl group, $R^3$ is (a) an alkyl group optionally substituted by hydroxyl group, (b) carboxyl group, (c) an alkyloxycarbonyl group or (d) a group of the formula: —CON($R^e$)($R^f$), $R^e$ and $R^f$ are the same or different and each hydrogen atom, an alkyl group or a trihalogenoalkyl group, $R^4$ is hydrogen atom; or A3) R' is a group of the formula [iii], $R^A$ is an alkyl group optionally substituted hydroxyl group, a phenyl group optionally substituted by a halogen atom or a trihalogenoalkyl group or a 5- to 6-membered nitrogen-containing heteroaryl group, $R^B$ is hydrogen atom or an alkyl group, $R^3$ is an alkyl group, carboxyl group or a group of the formula: —CON($R^a$)($R^b$), $R^a$ and $R^b$ are the same or different and each hydrogen atom or an alkyl group; and $R^{OA}$ is hydrogen atom, an alkyl group optionally substituted by one to three halogen atom(s), an alkyloxy group optionally substituted by hydroxyl group, a hydroxyalkyl group, an amino group optionally substituted by one to two group(s) selected from an alkyl group, an alkylcarbonyl group and an alkylsulfonyl group or a 4- to 6-membered nitrogen-containing aliphatic heterocyclic group.

Among the preferred compounds [I-I] of the present invention, examples of the more preferred compound include:

A1) a compound [I-I] in which R' is a group of the formula [i], $R^3$ is (a) a $C_{1-6}$ alkyl group, (b) a hydroxy-$C_{1-6}$ alkyl group, (c) an amino-$C_{1-6}$ alkyl group, (d) cyano group, (e) carboxyl group, (f) a $C_{1-6}$ alkyloxy-carbonyl group, (g) carbamoyl group, (h) a mono- or di($C_{1-6}$ alkyl)carbamoyl group, (i) a di($C_{1-6}$ alkyl)amino-$C_{1-6}$ alkyl-carbamoyl group or (j) a $C_{1-6}$ alkyloxy-carbonylamino group, and $R^4$ is hydrogen atom or a phenyl-$C_{1-6}$ alkyloxy-carbonylamino group;

A2) a compound [I-I] in which R' is a group of the formula [ii], X is sulfur atom, a group of the formula: —$SO_2$—, oxygen atom or a group of the formula: —$NR^k$—, $R^k$ is a $C_{1-6}$ alkyloxy-carbonyl group, a $C_{1-6}$ alkylsulfonyl group, a $C_{1-6}$ alkyl-carbonyl group or a di($C_{1-6}$ alkyl)aminosulfonyl group, $R^3$ is (a) carbamoyl group, (b) a mono- or di($C_{1-6}$ alkyl)-carbamoyl group, (c) a mono(trihalogeno-$C_{1-6}$ alkyl)carbamoyl group, (d) a $C_{1-6}$ alkyloxy-carbonyl group, (e) a $C_{1-6}$ alkyl group or (f) a hydroxy-$C_{1-6}$ alkyl group and $R^4$ is hydrogen atom; or A3) a compound [I-I] in which R' is a group of the formula [iii], $R^A$ is a $C_{1-6}$ alkyl group, a hydroxy-$C_{1-6}$ alkyl group, phenyl group, a halogenophenyl group, a trihalogeno($C_{1-6}$ alkyl)-phenyl group or a pyridyl group, $R^B$ is hydrogen atom or a $C_{1-6}$ alkyl group and $R^3$ is a $C_{1-6}$ alkyl group, carboxyl group, a $C_{1-6}$ alkyloxy-carbonyl group or carbamoyl group.

Among the compounds [I-I] of the above group A1 to A3, examples of the further preferred compound include those in which $R^1$ is a phenyl group substituted by one to two group(s) selected from a halogen atom, a dihalogeno-$C_{1-6}$ alkyl group, a trihalogeno-$C_{1-6}$ alkyl group and a di($C_{1-6}$ alkyl)amino group, a $C_{1-6}$ alkyloxy-pyrrolidinyl group, a $C_{1-6}$ alkyl-piperidyl group or a $C_{1-6}$ alkyloxy-piperidyl group, $R^2$ is (a) a phenyl group substituted by one or two halogen atom(s), (b) a cyanophenyl group or (c) a trihalogeno($C_{1-6}$ alkyl)-pyridyl group and $R^{OA}$ is hydrogen atom, a $C_{1-6}$ alkyl group, a dihalogeno-$C_{1-6}$ alkyl group, a trihalogeno-$C_{1-16}$ alkyl group, a $C_{1-6}$ alkyloxy group, a hydroxy-$C_{1-6}$ alkyloxy group, amino group, a $C_{1-6}$ alkyl-carbonylamino group, a mono($C_{1-6}$ alkyl) carbamoyl group or a 4- to 6-membered nitrogen-containing aliphatic heterocyclic group.

Among the compounds [I-I], the particularly preferred compound may be a compound selected from the group consisting of 6-(2-chlorophenyl)-7-(4-chlorophenyl)-3-[N-(1-cyanocyclohexyl)carbamoyl]-pyrazolo[1,5-a]pyrimidine;
6-(2-chlorophenyl)-7-(4-chlorophenyl)-3-[N-(1-cyanocyclopentyl)carbamoyl]-pyrazolo[1,5-a]pyrimidine;
6-(2-chlorophenyl)-7-(4-chlorophenyl)-3-[N-(1-methylcyclohexyl)carbamoyl]-pyrazolo[1,5-a]pyrimidine;
6-(2-chlorophenyl)-7-(4-chlorophenyl)-3-[N-(1-methylcyclopropyl)carbamoyl]pyrazolo[1,5-a]pyrimidine;
6-(2-chlorophenyl)-3-[N-(1-cyanocyclopentyl)-carbamoyl]-7-(4-trifluoromethylphenyl)-2-methylpyrazolo[1,5-a]pyrimidine;
6-(2-chlorophenyl)-3-[N-(1-cyanocyclohexyl)carbamoyl]-7-(4-trifluoromethylphenyl)-2-methylpyrazolo[1,5-a]pyrimidine;
3-[N-(4-carbamoyl-1,1-dioxo-tetrahydrothiopyran-4-yl)carbamoyl]-6-(2-chlorophenyl)-7-(4-chlorophenyl)-pyrazolo[1,5-a]pyrimidine;
2-acetylamino-6-(2-chlorophenyl)-7-(4-trifluoromethylphenyl)-3-[N-[1-(2-pyridyl)ethyl]carbamoyl]-pyrazolo[1,5-a]pyrimidine;
6-(2-chlorophenyl)-7-(4-chloro-2-fluorophenyl)-3-[N-[1-(2-pyridyl)ethyl]carbamoyl]pyrazolo[1,5-a]pyrimidine;
6-(2-chlorophenyl)-7-(4-trifluoromethylphenyl)-3-[N-[1-(2-pyridyl)ethyl]carbamoyl]-2-(1-pyrrolidinyl)-pyrazolo[1,5-a]pyrimidine;
3-[N-(1-carbamoylcyclohexyl)carbamoyl]-6-(2-chlorophenyl)-7-(4-chlorophenyl)pyrazolo[1,5-a]pyrimidine;
6-(2-chlorophenyl)-7-(4-chlorophenyl)-3-[N-[1-methyl-1-(2-pyridyl)ethyl]carbamoyl]pyrazolo[1,5-a]pyrimidine;
6-(2-chlorophenyl)-7-(4-trifluoromethylphenyl)-3-[N-[1-methyl-1-(2-pyridyl)-ethyl]carbamoyl]pyrazolo[1,5-a]pyrimidine;
3-[N-(4-carbamoyl-1,1-dioxo-tetrahydrothiopyran-4-yl)carbamoyl]-6-(2-chlorophenyl)-7-(4-trifluoromethylphenyl)pyrazolo[1,5-a]pyrimidine;
3-[N-(1-carboxycyclohexyl)carbamoyl]-6-(2-chlorophenyl)-7-(4-chlorophenyl)pyrazolo[1,5-a]pyrimidine;
6-(2-chlorophenyl)-7-(4-chlorophenyl)-3-[[1-[N-[2-(N,N-dimethylamino)ethyl]carbamoyl]cyclohexyl]carbamoyl]-pyrazolo[1,5-a]pyrimidine;
6-(2-chlorophenyl)-7-(4-chlorophenyl)-3-[N-[1-(N-methylcarbamoyl)cyclohexyl]carbamoyl]pyrazolo[1,5-a]pyrimidine;
6-(2-chlorophenyl)-7-(4-chlorophenyl)-3-[N-[1-(N,N-dimethylcarbamoyl)cyclohexyl]carbamoyl]pyrazolo[1,5-a]pyrimidine;
(S)-3-[N-(1-carboxy-2-methylpropyl)carbamoyl]-6-(2-chlorophenyl)-7-(4-chlorophenyl)pyrazolo[1,5-a]pyrimidine;
(S)-3-[N-(1-carboxy-2-phenylethyl)carbamoyl]-6-(2-chlorophenyl)-7-(4-trifluoromethylphenyl)pyrazolo[1,5-a]pyrimidine;
(S)-3-[N-(1-carboxy-2-methylpropyl)carbamoyl]-6-(2-chlorophenyl)-7-(4-trifluoromethylphenyl)pyrazolo[1,5-a]pyrimidine;
(S)-3-[N-(α-carboxybenzyl)carbamoyl]-6-(2-chlorophenyl)-7-(4-trifluoromethylphenyl)pyrazolo[1,5-a]pyrimidine;
(S)-3-[N-(1-carboxy-2-methylpropyl)carbamoyl]-6-(2-chlorophenyl)-7-(4-chlorophenyl)-2-methylpyrazolo[1,5-a]pyrimidine;
3-[N-(1-carboxy-1-methylethyl)carbamoyl]-6-(2-chlorophenyl)-7-(4-chlorophenyl)-2-methylpyrazolo[1,5-a]pyrimidine;
3-[N-(α-carboxybenzyl)carbamoyl]-6-(2-chlorophenyl)-7-(4-chlorophenyl)pyrazolo[1,5-a]pyrimidine;
3-[N-(1-carboxy-1-methylethyl)carbamoyl]-6-(2-chlorophenyl)-7-(4-trifluoromethylphenyl)pyrazolo[1,5-a]pyrimidine;
3-[N-(1-carboxy-2-phenylethyl)carbamoyl]-6-(2-chlorophenyl)-7-(4-chlorophenyl)pyrazolo[1,5-a]pyrimidine;
3-[N-(4-carboxy-1-cyclohexyl)carbamoyl]-6-(2-chlorophenyl)-7-(4-trifluoromethylphenyl)pyrazolo[1,5-a]pyrimidine;
3-[N-(4-carboxybenzyl)carbamoyl]-6-(2-chlorophenyl)-7-(4-trifluoromethylphenyl)pyrazolo[1,5-a]pyrimidine;
3-[N-(3-carboxybenzyl)carbamoyl]-6-(2-chlorophenyl)-7-(4-trifluoromethylphenyl)pyrazolo[1,5-a]pyrimidine;
6-(2-chlorophenyl)-7-(4-chlorophenyl)-3-[N-[1-(2-pyridyl)ethyl]carbamoyl]pyrazolo[1,5-a]pyrimidine;
6-(2-chlorophenyl)-3-[N-(1-cyanocyclohexyl)carbamoyl]-7-(4-trifluoromethylphenyl)pyrazolo[1,5-a]pyrimidine;
p0 6-(2-chlorophenyl)-7-(4-chlorophenyl)-3-[N-(1-methoxycarbonylcyclohexyl)carbamoyl]pyrazolo[1,5-a]pyrimidine;
6-(2-chlorophenyl)-7-(4-chlorophenyl)-2-(methylsulfonylamino)-3-[N-[1-(2-pyridyl)ethyl]carbamoyl]-pyrazolo[1,5-a]pyrimidine;
6-(2-chlorophenyl)-7-(4-chlorophenyl)-2-[N-methyl-N-(methylsulfonyl)amino]-3-[N-[1-(2-pyridyl)ethyl]carbamoyl]-pyrazolo[1,5-a]pyrimidine;
6-(2-chlorophenyl)-7-(4-methylpiperidin-1-yl)-3-[N-[1-methyl-1-(2-pyridyl)ethyl]carbamoyl]pyrazolo[1,5-a]pyrimidine;
6-(2-chlorophenyl)-7-(4-methoxypiperidin-1-yl)-3-[N-[1-methyl-1-(2-pyridyl)ethyl]carbamoyl]pyrazolo[1,5-a]pyrimidine;
6-(2-chlorophenyl)-7-(3-methoxypyrrolidin-1-yl)-3-[N-[1-methyl-1-(2-pyridyl)ethyl]carbamoyl]pyrazolo[1,5-a]pyrimidine;
6-(2-chlorophenyl)-7-(4-trifluoromethylphenyl)-3-[N-(1-methoxycarbonylcyclohexyl)sulfamoyl]-2-methylpyrazolo[1,5-a]pyrimidine;
3-[N-(1-carboxycyclohexyl)sulfamoyl]-6-(2-chlorophenyl)-7-(4-trifluoromethylphenyl)-2-methylpyrazolo[1,5-a]pyrimidine;
6-(2-chlorophenyl)-7-(4-trifluoromethylphenyl)-3-[N-(4-methoxycarbonyl-1,1-dioxo-tetrahydrothiopyran-4-yl)carbamoyl]pyrazolo[1,5-a]pyrimidine;
6-(2-chlorophenyl)-7-(4-trifluoromethylphenyl)-3-[N-(4-methyl-1,1-dioxo-tetrahydrothiopyran-4-yl)carbamoyl]-pyrazolo[1,5-a]pyrimidine;
6-(2-chlorophenyl)-7-(4-chlorophenyl)-2-methyl-3-[N-(4-methyl-1,1-dioxo-tetrahydrothiopyran-4-yl)carbamoyl]-pyrazolo[1,5-a]pyrimidine;
6-(2-chlorophenyl)-7-(4-trifluoromethylphenyl)-2-methyl-3-[N-(4-methyl-1,1-dioxo-tetrahydrothiopyran-4-yl)carbamoyl]pyrazolo[1,5-a]pyrimidine;
6-(2-chlorophenyl)-7-(4-chlorophenyl)-3-[N-(3-hydroxy-2-methylprop-2-yl)carbamoyl]-2-methylpyrazolo[1,5-a]pyrimidine;
6-(2-chlorophenyl)-7-(4-trifluoromethylphenyl)-3-[N-(4-hydroxymethyl-1,1-dioxo-tetrahydrothiopyran-4-yl)-carbamoyl]pyrazolo[1,5-a]pyrimidine;
6-(2-chlorophenyl)-7-(4-chlorophenyl)-2-trifluoromethyl-3-[N-(4-methyl-1,1-dioxo-tetrahydrothiopyran-4-yl)carbamoyl]pyrazolo[1,5-a]pyrimidine;
6-(2-chlorophenyl)-7-(4-chlorophenyl)-2-ethoxy-3-[N-(4-methyl-1,1-dioxo-tetrahydrothiopyran-4-yl)carbamoyl]-pyrazolo[1,5-a]pyrimidine;

6-(2-chlorophenyl)-7-(2-fluoro-4-trifluoromethylphenyl)-3-[N-(4-methyl-1,1-dioxo-tetrahydrothiopyran-4-yl)carbamoyl]pyrazolo[1,5-a]pyrimidine;

6-(2-chlorophenyl)-7-(4-trifluoromethylphenyl)-3-[N-(3-methoxycarbonyl-1,1-dioxothietan-3-yl)carbamoyl]-pyrazolo[1,5-a]pyrimidine;

6-(2-chlorophenyl)-7-(4-chlorophenyl)-3-[N-(1-cyanocyclohexyl)carbamoyl]-2-methylpyrazolo[1,5-a]pyrimidine;

6-(2-chlorophenyl)-7-(4-chlorophenyl)-2-(2-hydroxyethoxy)-3-[N-(3-methyl-1,1-dioxo-tetrahydrothien-3-yl)carbamoyl]pyrazolo[1,5-a]pyrimidine;

6-(2-chlorophenyl)-7-(4-trifluoromethylphenyl)-2-(2-hydroxyethoxy)-3-[N-(3-methyl-1,1-dioxotetrahydrothien-3-yl)carbamoyl]pyrazolo[1,5-a]pyrimidine;

6-(2-chlorophenyl)-7-(4-trifluoromethylphenyl)-3-[N-(3-methyl-1,1-dioxotetrahydrothien-3-yl)carbamoyl]-pyrazolo[1,5-a]pyrimidine;

6-(2-chlorophenyl)-2-(difluoromethyl)-7-(4-trifluoromethylphenyl)-3-[N-(3-methyl-1,1-dioxotetrahydrothien-3-yl)carbamoyl]pyrazolo[1,5-a]pyrimidine;

6-(2-chlorophenyl)-7-(4-chlorophenyl)-2-(trifluoromethyl)-3-[N-(3-methyl-1,1-dioxotetrahydrothien-3-yl)carbamoyl]pyrazolo[1,5-a]pyrimidine;

6-(2-chlorophenyl)-7-(4-trifluoromethylphenyl)-3-[N-[4-(N-methylcarbamoyl)-1,1-dioxotetrahydrothiopyran-4-yl]-carbamoyl]pyrazolo[1,5-a]pyrimidine;

6-(2-chlorophenyl)-3-[N-[4-[N-(2,2,2-trifluoroethyl)-carbamoyl]-1,1-dioxotetrahydrothiopyran-4-yl]carbamoyl]-7-(4-trifluoromethylphenyl)pyrazolo[1,5-a]pyrimidine; and 6-(2-chlorophenyl)-3-[N-[4-[N-(2,2,2-trifluoroethyl)-carbamoyl]-1,1-dioxotetrahydrothiopyran-4-yl]carbamoyl]-7-(4-trifluoromethylphenyl)-2-methylpyrazolo[1,5-a]pyrimidine or a pharmaceutically acceptable salt thereof.

Examples of another preferred compound of the present invention include:

B1) a compound [I-II] in which $R^1$ and $R^2$ are the same or different and each a phenyl group optionally substituted by one to two group(s) selected from a halogen atom, cyano group, an alkyl group, a dihalogenoalkyl group and a trihalogenoalkyl group, R" is a group of the formula: —N($R^5$)($R^6$), $R^5$ is hydrogen atom or an alkyl group and $R^6$ is (a) an alkyl group optionally substituted by one to three group(s) selected from a halogen atom, hydroxyl group, cyano group, an alkyloxy group, a $C_{3-8}$ cycloalkyl group, a hydroxy-$C_{3-8}$ cycloalkyl group, an amino-$C_{3-8}$ cycloalkyl group, a $C_{3-8}$ cycloalkyl group substituted by one or two halogen atom(s), a dialkylamino group, carboxyl group, a carbamoyl group optionally substituted by one or two alkyl group(s), a phenyl group optionally substituted by one or two halogen atom(s), a trihalogenoalkyl-phenyl group, an alkyloxyphenyl group, a carboxyphenyl group and a saturated or unsaturated 5- to 6-membered nitrogen- or oxygen-containing heterocyclic group, (b) a $C_{3-8}$ cycloalkyl group, said cycloalkyl group being optionally fused to a benzene ring and optionally substituted by one to two group(s) selected from cyano group, an alkyl group, a hydroxyalkyl group, a carboxyalkyl group, an aminoalkyl group, an alkylcarbonylamino-alkyl group, a dialkylcarbamoyl-amino-alkyl group, an alkylsulfonylamino-alkyl group, a dialkylsulfamoylamino-alkyl group, carboxyl group, an alkyloxycarbonyl group, a phenylalkyloxycarbonyl group, a group of the formula: —CON($R^{a1}$)($R^{b1}$) and a tetrazolyl group, $R^{a1}$ and $R^{b1}$ are the same or different and each hydrogen atom, an alkyl group or a dialkylamino-alkyl group, (c) a saturated or unsaturated 4- to 6-membered nitrogen-, sulfur- or oxygen-containing heterocyclic group optionally substituted by one to three group(s) selected from oxo group, hydroxy group, cyano group, an alkyl group, a hydroxyalkyl group, carboxyl group, an alkyloxycarbonyl group, an alkylsulfonyl group, a group of the formula: —CON($R^{a2}$)($R^{b2}$), pyrrolidinylcarbonyl group or morpholinocarbonyl group and $R^{a2}$ and $R^{b2}$ are the same or different and each hydrogen atom, an alkyl group, a trihalogenoalkyl group, a cyanoalkyl group, a hydroxyalkyl group, an alkyloxyalkyl group, an alkylsulfonyl group or a $C_{3-8}$ cycloalkyl group or (d) an amino group optionally substituted by one to two group(s) selected from an alkyl group and a pyridyl group, excluding 6-(2-chlorophenyl)-7-(4-chlorophenyl)-3-[N-(1,1-dioxo-tetrahydrothien-3-yl)-carbamoyl]-2-(hydroxymethyl)pyrazolo[1,5-a]pyrimidine; and B2) a compound [I-II] in which $R^1$ and $R^2$ are the same or different and each a phenyl group optionally substituted by one to two group(s) selected from a halogen atom, cyano group, a dihalogenoalkyl group and a trihalogenoalkyl group, $R^{OB}$ is a group of the formula: —$SO_2N(R^{O1})(R^{O2})$ and R" is an alkyloxy group.

Among the compounds [I-II], the more preferred compound may be a compound in which E is a group of the formula: —C(=O)—.

Among the compounds [I-II], examples of the further preferred compound include:

B1-1) a compound in which $R^1$ and $R^2$ are the same or different and each a phenyl group optionally substituted by one to two group(s)-selected from a halogen atom, cyano group, an alkyl group, a dihalogenoalkyl group and a trihalogenoalkyl group, $R^{OB}$ is a group of the formula: —NHCONH$R^{O3}$, E is a group of the formula: —C(=O)—, R" is a group of the formula: —N($R^5$)($R^6$), $R^5$ is hydrogen atom and $R^6$ is (a) an alkyl group, (b) a trihalogenoalkyl group, (c) a $C_{3-8}$ cycloalkyl group, (d) a dialkylamino group or (e) a saturated or unsaturated 5- to 6-membered sulfur-containing heterocyclic group optionally substituted by one to three group(s) selected from oxo group, an alkyl group and carbamoyl group;

B1-2) a compound in which $R^1$ and $R^2$ are the same or different and each (i) a phenyl group optionally substituted by one to two group(s) selected from a halogen atom, cyano group, an alkyl group, a dihalogenoalkyl group, a trihalogenoalkyl group and an alkyloxy group or (ii) a saturated or unsaturated 5- to 6-membered nitrogen-containing heteromonocyclic group, $R^{OB}$ is a group of the formula: —$SO_2N(R^{O1})(R^{O2})$, $R^{O1}$ is hydrogen atom or an alkyl group, $R^{O2}$ is hydrogen atom, an alkyl group or a carbamoylalkyl group, E is a group of the formula: —C(=O)—, R" is a group of the formula: —N($R^5$)($R^6$), $R^5$ is hydrogen atom or an alkyl group and $R^6$ is (a) an alkyl group optionally substituted by one to three group(s) selected from a halogen atom, hydroxyl group, cyano group, an alkyloxy group, a $C_{3-8}$ cycloalkyl group optionally substituted by one to two halogen atom(s), an amino group optionally substituted by one to two alkyl group(s) and a pyridyl group, (b) a $C_{3-8}$ cycloalkyl group optionally substituted by a group selected from an alkyl group and carbamoyl group, (c) an amino group optionally substituted by one to two group(s) selected from an alkyl group and a pyridyl group or (d) a saturated or unsaturated 5- to 6-membered nitrogen- or sulfur-containing heterocyclic group optionally substituted by one to three group(s) selected from oxo group, an alkyl group and carbamoyl group;

B1-3) a compound in which $R^1$ and $R^2$ are the same or different and each a phenyl group optionally substituted by one to two group(s) selected from a halogen atom and a trihalogenoalkyl group, $R^{OB}$ is a group of the formula: —CON($R^e$)($R^f$), $R^e$ is hydrogen atom or an alkyl group, $R^f$ is hydrogen atom, an alkyl group or a dialkylamino group, E is a group of the formula: —C(=O)—, R" is a group of the formula: —N($R^5$)($R^6$), $R^5$ is hydrogen atom and $R^6$ is (a) an alkyl group optionally substituted by one to three halogen atom(s), (b) a $C_{3-8}$ cycloalkyl group or (c) a saturated or unsaturated 4- to 6-membered sulfur-containing heterocyclic group optionally substituted by one to three group(s) selected from an oxo group and an alkyl group;

B1-4) a compound in which $R^1$ and $R^2$ are the same or different and each a phenyl group optionally substituted by one to two group(s) selected from a halogen atom and a trihalogenoalkyl group, $R^{OB}$ is a hydroxyalkyl group, E is a group of the formula: —C(=O)—, R" is a group of the formula: —N($R^5$)($R^6$), $R^5$ is hydrogen atom and $R^6$ is (a) an alkyl group optionally substituted by one to three halogen atom(s), (b) an alkyl group substituted by a pyridyl group, (c) a $C_{3-8}$ cycloalkyl group optionally substituted by a group selected from cyano group and carbamoyl group or (d) a saturated or unsaturated 4- to 6-membered nitrogen- or sulfur-containing heterocyclic group optionally substituted by one to three group(s) selected from oxo group and an alkyl group, excluding 6-(2-chlorophenyl)-7-(4-chlorophenyl)-3-[N-(1,1-dioxotetrahydro-thien-3-yl)-carbamoyl]-2-(hydroxymethyl)pyrazolo[1,5-a]pyrimidine;

B1-5) a compound in which $R^1$ and $R^2$ are the same or different and each a phenyl group optionally substituted by one to two group(s) selected from a halogen atom and a trihalogenoalkyl group, $R^{OB}$ is carboxyl group, E is a group of the formula: —C(=O)—, R" is a group of the formula: —N($R^5$)($R^6$), $R^5$ is hydrogen atom and $R^6$ is a saturated or unsaturated 5- to 6-membered sulfur-containing heterocyclic group optionally substituted by one to three group(s) selected from oxo group and an alkyl group; and B2-1) a compound in which $R^1$ and $R^2$ are the same or different and each a halogenophenyl group, $R^{OB}$ is a sulfamoyl group optionally substituted by one to two alkyl group(s), E is a group of the formula: —C(=O)— and R" is an alkyloxy group.

Among the above compounds [I-II], examples of the particularly preferred compound may be:

B1-a) a compound in which $R^1$ is (i) a phenyl group optionally substituted by one to two group(s) selected from a halogen atom, a $C_{1-6}$ alkyl group, a dihalogeno-$C_{1-6}$ alkyl group and a trihalogeno-$C_{1-6}$ alkyl group or (ii) piperidino group, $R^2$ is a phenyl group optionally substituted by one to two group(s) selected from a halogen atom and cyano group, $R^{OB}$ is a group of the formula: —$SO_2$N($R^{O1}$)($R^{O2}$), $R^{O1}$ is hydrogen atom or a $C_{1-6}$ alkyl group, $R^{O2}$ is hydrogen atom, a $C_{1-6}$ alkyl group or a carbamoyl-$C_{1-6}$ alkyl group, $R^5$ is hydrogen atom, $R^6$ is (a) a $C_{1-6}$ alkyl group optionally substituted by one to three group(s) selected from a halogen atom, a $C_{1-6}$ alkyloxy group, a $C_{3-8}$ cycloalkyl group and a pyridyl group, (b) a $C_{3-8}$ cycloalkyl group optionally substituted by a $C_{1-6}$ alkyl group, (c) an amino group optionally substituted by one to two group(s) selected from a $C_{1-6}$ alkyl group and a pyridyl group or (d) a saturated or unsaturated 5- to 6-membered nitrogen- or sulfur-containing heterocyclic group optionally substituted by one to two oxo group(s); or B1-b) a compound in which $R^1$ is a trihalogeno-$C_{1-6}$ alkylphenyl group, $R^2$ is a halogenophenyl group, $R^{OB}$ is a group of the formula: —CON($R^e$)($R^f$), $R^e$ is hydrogen atom or a $C_{1-6}$ alkyl group, $R^f$ is hydrogen atom or a $C_{1-6}$ alkyl group, $R^5$ is hydrogen atom, $R^6$ is (a) $C_{1-6}$ alkyl group optionally substituted by one to three halogen atom(s) or (b) a saturated or unsaturated 5- to 6-membered sulfur-containing heterocyclic group optionally substituted by one to three group(s) selected from an oxo group and a $C_{1-6}$ alkyl group; or B1-c) a compound in which $R^1$ is a trihalogeno-$C_{1-6}$ alkylphenyl group, $R^2$ is a halogenophenyl group, $R^{OB}$ is a hydroxy-$C_{1-6}$ alkyl group, $R^5$ is hydrogen atom, $R^6$ is (a) a trihalogeno-$C_{1-6}$ alkyl group, (b) a pyridyl-$C_{1-6}$ alkyl group, (c) a $C_{5-7}$ cycloalkyl group substituted by a group selected from cyano group and carbamoyl group or (d) a saturated or unsaturated 5- to 6-membered sulfur-containing heterocyclic group optionally substituted by one to three group(s) selected from an oxo group and a $C_{1-6}$ alkyl group, excluding 6-(2-chlorophenyl)-7-(4-chlorophenyl)-3-[N-(1,1-dioxo-tetrahydrothien-3-yl)carbamoyl]-2-(hydroxymethyl)-pyrazolo[1,5-a]pyrimidine; or B2-a) a compound in which $R^1$ and $R^2$ are the same or different and each a halogenophenyl group, $R^{OB}$ is a $C_{1-6}$ alkyl-sulfamoyl group and R" is a $C_{1-6}$ alkyloxy group.

Examples of the particularly preferred compounds [I-II] mentioned above include a compound selected from the group consisting of:

6-(2-chlorophenyl)-7-(4-chlorophenyl)-3-ethoxycarbonyl-2-(N-methylsulfamoyl)pyrazolo[1,5-a]pyrimidine;

6-(2-chlorophenyl)-7-(4-chlorophenyl)-3-ethoxycarbonyl-2-(N,N-dimethylsulfamoyl)pyrazolo[1,5-a]pyrimidine;

(R)-6-(2-chlorophenyl)-7-(4-chlorophenyl)-2-(N-methylsulfamoyl)-3-[N-(1,1-dioxotetrahydrothien-3-yl)-carbamoyl]pyrazolo[1,5-a]pyrimidine;

6-(2-chlorophenyl)-7-(4-chlorophenyl)-3-[N-(cyclopentyl)carbamoyl]-2-(N-methylsulfamoyl)pyrazolo[1,5-a]pyrimidine;

6-(2-chlorophenyl)-7-(4-chlorophenyl)-3-[[N'-methyl-N'-(2-pyridyl)hydrazino]carbonyl]-2-(N-methylsulfamoyl)-pyrazolo[1,5-a]pyrimidine;

(R)-6-(2-chlorophenyl)-7-(4-chlorophenyl)-2-(N,N-dimethylsulfamoyl)-3-[N-(1,1-dioxotetrahydrothien-3-yl)-carbamoyl]pyrazolo[1,5-a]pyrimidine;

6-(2-chlorophenyl)-7-(4-chlorophenyl)-3-[N-(cyclopentyl)carbamoyl]-2-(N,N-dimethylsulfamoyl)-pyrazolo[1,5-a]pyrimidine;

6-(2-chlorophenyl)-7-(4-chlorophenyl)-2-(N,N-dimethylsulfamoyl)-3-[N-(1-pyrrolidinyl)carbamoyl]-pyrazolo[1,5-a]pyrimidine;

6-(2-chlorophenyl)-7-(4-chlorophenyl)-3-[[N'-methyl-N'-(2-pyridyl)hydrazino]carbonyl]-2-(N,N-dimethylsulfamoyl)pyrazolo[1,5-a]pyrimidine;

6-(2-chlorophenyl)-7-(4-chlorophenyl)-2-(N-methylsulfamoyl)-3-[N-(1-pyrrolidinyl)carbamoyl]-pyrazolo[1,5-a]pyrimidine;

(R)-6-(2-chlorophenyl)-7-(4-chlorophenyl)-3-[N-(1,1-dioxotetrahydrothien-3-yl)carbamoyl]-2-sulfamoylpyrazolo[1,5-a]pyrimidine;

6-(2-chlorophenyl)-7-(4-chlorophenyl)-3-[N-(1-pyrrolidinyl)carbamoyl]-2-sulfamoylpyrazolo[1,5-a]pyrimidine;

6-(2-chlorophenyl)-7-(4-chlorophenyl)-3-[[N'-methyl-N'-(2-pyridyl)hydrazino]carbonyl]-2-sulfamoylpyrazolo[1,5-a]pyrimidine;

(S)-6-(2-chlorophenyl)-7-(4-chlorophenyl)-3-[N-(1,1-dioxotetrahydrothien-3-yl)carbamoyl]-2-sulfamoylpyrazolo[1,5-a]pyrimidine;

6-(2-chlorophenyl)-7-(4-chlorophenyl)-3-[N-(cyclopentyl)carbamoyl]-2-sulfamoylpyrazolo[1,5-a]pyrimidine;

6-(2-chlorophenyl)-7-(4-chlorophenyl)-3-[N-(1,1-dioxotetrahydrothiopyran-4-yl)carbamoyl]-2-sulfamoylpyrazolo[1,5-a]pyrimidine;

(R)-6-(2-chlorophenyl)-7-(4-trifluoromethylphenyl)-3-[N-(1,1-dioxotetrahydrothien-3-yl)carbamoyl]-2-sulfamoylpyrazolo[1,5-a]pyrimidine;

(S)-6-(2-chlorophenyl)-7-(4-trifluoromethylphenyl)-3-[N-(1,1-dioxotetrahydrothien-3-yl)carbamoyl]-2-sulfamoylpyrazolo[1,5-a]pyrimidine;

6-(2-chlorophenyl)-3-[N-(cyclopentyl)carbamoyl]-7-(4-trifluoromethylphenyl)-2-sulfamoylpyrazolo[1,5-a]pyrimidine;

(R)-7-(4-chlorophenyl)-6-(2-cyanophenyl)-3-[N-(1,1-dioxotetrahydrothien-3-yl)carbamoyl]-2-sulfamoylpyrazolo[1,5-a]pyrimidine;

7-(4-chlorophenyl)-6-(2-cyanophenyl)-3-[N-(cyclopentyl)carbamoyl]-2-sulfamoylpyrazolo[1,5-a]pyrimidine;

7-(4-chlorophenyl)-6-(2-cyanophenyl)-3-[[N'-methyl-N'-(2-pyridyl)hydrazino]carbonyl]-2-sulfamoylpyrazolo[1,5-a]pyrimidine;

(R)-2-[N-(carbamoylmethyl)sulfamoyl]-6-(2-chlorophenyl)-7-(4-chlorophenyl)-3-[N-(1,1-dioxotetrahydrothien-3-yl)carbamoyl]pyrazolo[1,5-a]pyrimidine;

2-[N-(carbamoylmethyl)sulfamoyl]-6-(2-chlorophenyl)-7-(4-chlorophenyl)-3-[N-(cyclopentyl)carbamoyl]pyrazolo[1,5-a]pyrimidine;

2-[N-(carbamoylmethyl)sulfamoyl]-6-(2-chlorophenyl)-7-(4-chlorophenyl)-3-[[N'-methyl-N'-(2-pyridyl)hydrazino]-carbonyl]pyrazolo[1,5-a]pyrimidine;

2-[N-(carbamoylmethyl)sulfamoyl]-6-(2-chlorophenyl)-7-(4-chlorophenyl)-3-[N-(1-pyrrolidinyl)carbamoyl]-pyrazolo[1,5-a]pyrimidine;

3-[N-(1-carboxycyclohexyl)carbamoyl]-6-(2-chlorophenyl)-7-(4-chlorophenyl)-2-(N-methylsulfamoyl)-pyrazolo[1,5-a]pyrimidine;

3-[N-(1-carbamoylcyclohexyl)carbamoyl]-6-(2-chlorophenyl)-7-(4-chlorophenyl)-2-sulfamoylpyrazolo[1,5-a]pyrimidine;

6-(2-chlorophenyl)-7-(4-trifluoromethylphenyl)-2-hydroxymethyl-3-[N-[1-methyl-1-(2-pyridyl)ethyl]carbamoyl]-pyrazolo[1,5-a]pyrimidine;

6-(2-chlorophenyl)-7-(4-trifluoromethylphenyl)-2-hydroxymethyl-3-[N-(3-methyl-1,1-dioxotetrahydrothien-3-yl)carbamoyl]pyrazolo[1,5-a]pyrimidine;

6-(2-chlorophenyl)-3-[N-(1-cyanocyclohexyl)carbamoyl]-7-(4-trifluoromethylphenyl)-2-(hydroxymethyl)pyrazolo[1,5-a]pyrimidine;

6-(2-chlorophenyl)-7-(4-trifluoromethylphenyl)-2-hydroxymethyl-3-[N-(4-methyl-1,1-dioxotetrahydrothiopyran-4-yl)carbamoyl]pyrazolo[1,5-a]pyrimidine;

2-carbamoyl-6-(2-chlorophenyl)-7-(4-trifluoromethylphenyl)-3-[N-(4-methyl-1,1-dioxotetrahydrothiopyran-4-yl)carbamoyl]pyrazolo[1,5-a]pyrimidine;

6-(2-chlorophenyl)-7-(4-trifluoromethylphenyl)-2-(N-methylcarbamoyl)-3-[N-(4-methyl-1,1-dioxotetrahydrothiopyran-4-yl)carbamoyl]pyrazolo[1,5-a]pyrimidine;

6-(2-chlorophenyl)-7-(4-chlorophenyl)-3-[N-(2,2-dimethylpropyl)carbamoyl]-2-sulfamoylpyrazolo[1,5-a]pyrimidine;

6-(2-chlorophenyl)-7-(4-chlorophenyl)-3-[N-(cyclohexylmethyl)carbamoyl]-2-sulfamoylpyrazolo[1,5-a]pyrimidine;

6-(2-chlorophenyl)-7-(4-chlorophenyl)-3-[N-(2,2,2-trifluoroethyl)carbamoyl]-2-sulfamoylpyrazolo[1,5-a]pyrimidine;

6-(2-chlorophenyl)-7-(4-chlorophenyl)-3-[N-(3-methylpropyl)carbamoyl]-2-sulfamoylpyrazolo[1,5-a]pyrimidine;

6-(2-chlorophenyl)-7-(4-chlorophenyl)-3-[N-(2,2-difluoroethyl)carbamoyl]-2-sulfamoylpyrazolo[1,5-a]pyrimidine;

6-(2-chlorophenyl)-7-(4-chlorophenyl)-3-[N-(cyclopropylmethyl)carbamoyl]-2-sulfamoylpyrazolo[1,5-a]pyrimidine;

6-(2-chlorophenyl)-7-(4-chlorophenyl)-3-[N-(1-methylcyclopropyl)carbamoyl]-2-sulfamoylpyrazolo[1,5-a]pyrimidine;

6-(2-chlorophenyl)-3-[N-(2,2,2-trifluoroethyl)-carbamoyl]-7-(4-trifluoromethylphenyl)-2-(hydroxymethyl)-pyrazolo[1,5-a]pyrimidine;

6-(2-chlorophenyl)-7-(4-difluoromethylphenyl)-3-[N-(isobutyl)carbamoyl]-2-sulfamoylpyrazolo[1,5-a]pyrimidine;

2-carbamoyl-6-(2-chlorophenyl)-3-[N-(2,2,2-trifluoroethyl)carbamoyl]-7-(4-trifluoromethylphenyl)-pyrazolo[1,5-a]pyrimidine;

6-(2-chlorophenyl)-7-(4-chloro-2-fluorophenyl)-3-[N-(2,2,2-trifluoroethyl)carbamoyl]-2-sulfamoylpyrazolo[1,5-a]pyrimidine;

6-(2-chlorophenyl)-7-(4-difluoromethylphenyl)-3-[N-(2,2,2-trifluoroethyl)carbamoyl]-2-sulfamoylpyrazolo[1,5-a]pyrimidine;

6-(2-chlorophenyl)-7-(4-trifluoromethylphenyl)-3-[N-(n-propyl)carbamoyl]-2-sulfamoylpyrazolo[1,5-a]pyrimidine;

6-(2-chlorophenyl)-7-(4-trifluoromethylphenyl)-3-[N-(isobutyl)carbamoyl]-2-sulfamoylpyrazolo[1,5-a]pyrimidine;

6-(2-chlorophenyl)-7-(4-trifluoromethylphenyl)-3-[N-(1-methylpropyl)carbamoyl]-2-sulfamoylpyrazolo[1,5-a]pyrimidine;

6-(2-chlorophenyl)-7-(4-trifluoromethylphenyl)-3-[N-(3-methoxyprop-2-yl)carbamoyl]-2-sulfamoylpyrazolo[1,5-a]pyrimidine;

6-(2-chlorophenyl)-7-(4-trifluoromethylphenyl)-3-[N-(1-methylcyclopropyl)carbamoyl]-2-sulfamoylpyrazolo[1,5-a]pyrimidine;

6-(2-chlorophenyl)-3-[N-(2,2,2-trifluoroethyl)-carbamoyl]-7-(4-fluorophenyl)-2-sulfamoylpyrazolo[1,5-a]pyrimidine;

6-(2-chlorophenyl)-7-(4-trifluoromethylphenyl)-3-[[N'-methyl-N'-(2-pyridyl)hydrazino]carbonyl]-2-sulfamoylpyrazolo[1,5-a]pyrimidine;

6-(2-chlorophenyl)-7-(4-trifluoromethylphenyl)-3-[N-(2,2,2-trifluoroethyl)carbamoyl]-2-(dimethylcarbamoyl)-pyrazolo[1,5-a]pyrimidine;

6-(2-chlorophenyl)-7-(4-trifluoromethylphenyl)-3-[N-[1-methyl-1-(2-pyridyl)ethyl]carbamoyl]-2-sulfamoylpyrazolo[1,5-a]pyrimidine;

6-(2-chlorophenyl)-3-[N-(3-methoxyprop-2-yl)-carbamoyl]-7-(4-methylphenyl)-2-sulfamoylpyrazolo[1,5-a]pyrimidine;

6-(2-chlorophenyl)-3-[N-(2,2,2-trifluoroethyl)-carbamoyl]-7-(4-methylphenyl)-2-sulfamoylpyrazolo[1,5-a]pyrimidine;

6-(2-chlorophenyl)-3-[N-(isobutyl)carbamoyl]-7-(4-methylphenyl)-2-sulfamoylpyrazolo[1,5-a]pyrimidine; and 6-(2-chlorophenyl)-3-[N-(cyclopentyl)carbamoyl]-7-(4-methylphenyl)-2-sulfamoylpyrazolo[1,5-a]pyrimidine;

or a pharmaceutically acceptable salt thereof.

When the compound [I] of the present invention has an asymmetric carbon atom(s) in its molecule, it may exist in the form of a stereoisomer thereof (diastereoisomers, optical isomers) owing to said asymmetric carbon atom(s) thereof, and the present invention also includes one of the stereoisomers and a mixture thereof.

A compound [I] of the present invention shows a high affinity to CB1 receptors and hence may be useful as a CB1 receptor ligand, particularly as a CB1 receptor antagonist. Based on the antagonistic activity, the compound may be useful as an agent for prevention and/or treatment of a CB1 receptor-mediated diseases such as psychosis including schizophrenia, anxiety disorders, stress, depression, epilepsy, neurodegenerative disorders, spinocerebellar disorders, cognitive disorders, craniocerebral trauma, panic attack, peripheral neuropathy, glaucoma, migraine, Parkinson's disease, Alzheimer's disease, Huntington's disease, Raynaud's syndrome, tremor, obsessive-compulsive disorders, amnesia, geriatric dementia, thymic disorders, Tourette's syndrome, tardive dyskinesia, bipolar disorders, cancer, drug-induced dyskinesia, dystonia, septic shock, hemorrhagic shock, hypotension, insomnia, immunological diseases including inflammations, multiple sclerosis, emesis, diarrhea, asthma, appetite disorders such as bulimarexia, anorexia and the like, obesity, non insulin-dependent diabetes mellitus (NIDDM), memory disorders, urinary disorders, cardiovascular disorders, infertility disorders, infections, demyelination-related diseases, neuroinflammation, viral encephalitis, cerebral vascular incidents, cirrhosis of the liver or gastrointestinal disorders including intestinal transit disorders.

In addition, a compound [I] of the present invention may be useful as an agent for withdrawal from a chronic treatment, alcohol dependence or drug abuse (e.g., an opioid, barbiturate, marijuana, cocaine, anphetamine, phencyclidine, a hallucinogenic agent, a benzodiazepine compound and the like).

Furthermore, a compound [I] of the present invention may be useful as an agent for enhancing analgesic activity of analgesic or narcotic drugs and the like; or an agent for smoking cessation (withdrawal from smoking or nicotine dependence).

Moreover, a compound [I] of the present invention can be useful for treatment of a condition relating to metabolic diseases including obesity, diabetes, impaired glucose tolerance, hyperinsulinemia, hyperlipidemia, hypercholesterolemia, hypertriglyceridemia, lipid metabolism disorder, atherosclerosis, hypertension, cardiovascular disease, coronary heart disease, depression, anxiety, drug addiction, and substance addiction.

Besides, the compound [I] of the present invention can be advantageous as a medicine due to its low toxicity.

Meanwhile, the compounds [I] of the present invention include compounds which may be useful as a selective antagonist to peripheral CB1 receptors from a viewpoint of their low brain penetration.

The compound [I] of the present invention can be clinically used either in the free form or in the form of a pharmaceutically acceptable salt thereof. The pharmaceutically acceptable salt of the compound [I] includes a salt with an inorganic acid such as hydrochloride, sulfate, phosphate or hydrobromide, or a salt with an organic acid such as acetate, fumarate, oxalate, citrate, methanesulfonate, benzenesulfonate, tosylate or maleate. Besides, when the compound [I] of the present invention has a carboxyl group(s) and the like in its molecule, examples of the pharmaceutically acceptable salt include, salts with a base such as alkaline metal (e.g., sodium salt, potassium salt) or alkaline earth metal (e.g., calcium salt).

The compound [I] or a pharmaceutically acceptable salt thereof includes either intramolecular salt or an additive thereof, and solvates or hydrates thereof.

The present compound [I] or a pharmaceutically acceptable salt thereof can be either orally or parenterally, and can be formulated into a conventional pharmaceutical preparation such as tablets, granules, capsules, powders, injections or inhalants.

The dose of the compound [I] of the present invention or a pharmaceutically acceptable salt thereof may vary in accordance with the administration routes, and the ages, weights and conditions of the patients. For example, when administered in an injection preparation, it is usually in the range of about 0.0001 to 1.0 mg/kg/day, preferably in the range of about 0.001 to 0.1 mg/kg/day. When administered in an oral preparation, it is usually in the range of about 0.001 to 100 mg/kg/day, preferably in the range of 0.01 to 10 mg/kg/day.

A compound [I] of the present invention may also be useful as adjunctive, add-on or supplementary therapy for the treatment of the above-mentioned diseases or disorders. The adjunctive, add-on or supplementary therapy means the concomitant or sequential administration of a compound of the present invention to a patient who has already received administration of, who is receiving administration of, or who will receive administration of one or more additional therapeutic agents for the treatment of the indicated conditions, for example one or more known anti-depressant, anti-psychotics or anxiolytic agents.

The compound [I] of the present invention can be prepared by the following methods but should not be construed to be limited thereto.

(Method A)

Among the compounds [I] of the present invention, a compound having the following formula [I-A]:

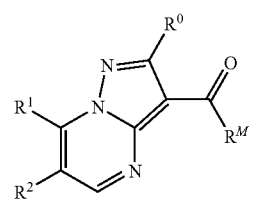

[I-A]

wherein $R^M$ is a group of the formula:

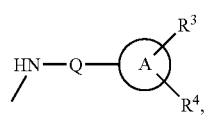

[i]

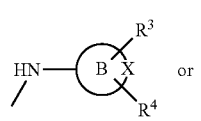

[ii]

or

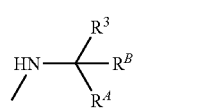

[iii]

or a group of the formula: —N($R^5$)($R^6$) and the other symbols are the same as defined above can be prepared by reacting a compound of the following formula [II-A]:

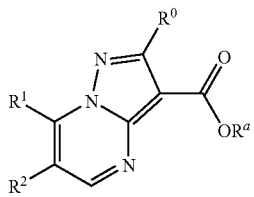

wherein $R^a$ is hydrogen atom, an alkyl group or benzyl group with an amine compound of the formula [III]:

$$HR^M \quad [III]$$

wherein $R^M$ is the same as defined above or a salt thereof.

When $R^a$ is hydrogen atom, the above-mentioned reaction can be carried out in a solvent in the presence of a condensing agent, and in the presence or absence of an activating agent and a base. Examples of the solvent include any solvent which does not disturb the reaction, such as methylene chloride, chloroform, dimethylformamide, dimethylacetamide, tetrahydrofuran, dioxane, toluene, benzene, 1,2-dichloroethane, 1-methylpyrrolidinone, 1,2-dimethoxyethane and the like. The condensing agent may be dicyclohexylcarbodiimide (DCC), 1-ethyl-3-(3-dimethylaminopropyl)carbodiimide hydrochloride (WSC HCl), diphenylphosphoryl azide (DPPA), carbonyldiimidazole (CDI), diethylcyanophosphonate (DEPC), diisopropylcarbodiimide (DIPCI), benzotriazol-1-yloxytrispyrrolidinophosphonium hexafluorophosphate (PyBOP), carbonylditriazole, N-cyclohexylcarbodiimide-N'-propyloxymethylpolystyrene (PS-carbodiimide), N-ethoxycarbonyl-2-ethoxy-1,2-dihydroquinoline (EEDQ), 2-(7-azabenzotriazol-1-yl)-1,1,3,3-tetramethyluronium hexafluorophosphate (HATU), 2-(1H-benzotriazol-1-yl-1,1,3,3-tetramethyluronium hexafluorophosphate (HBTU), bromotrispyrrolidinophosphonium hexafluorophosphate (PyBroP), 2-(1H-benzotriazol-1-yl)-1,1,3,3-tetramethyluronium tetrafluoroborate (TBTU), chloro-1,1,3,3-tetramethyl-uronium hexachloroantimonate (ACTU) and the like. Examples of the activating agent include 1-hydroxybenzotriazole (HOBt), 1-hydroxysuccinimide (HOSu), dimethylaminopyridine (DMAP), 1-hydroxy-7-azabenzotriazole (HOAt), hydroxyphthalimide (HOPht), pentafluorophenol (Pfp-OH), 1-hydroxybenzotriazole-6-sulfonamidomethylpolystyrene (PS-HOBt) and the like. The base includes, for example, pyridine, triethylamine, diisopropylethylamine, 4-methylmorpholine, 1,8-diazabicyclo[5,4,0]-7-undecene (DBU) and the like.

In the above-mentioned process, the compound [II-A] can be used in an amount of 0.33 to 1.5 moles, preferably 0.5 to 1.2 moles per one mole of the compound [III]. The condensing agent can be used in an amount of 1.0 to 3.0 moles, preferably 1.0 to 1.2 moles per one mole of the compound [II-A] or [III]. The base can be used in an amount of 1.0 to 3.0 moles, preferably 1.0 to 1.2 moles per one mole of the compound [II-A] or [III]. The activating agent can be used in an amount of 0.01 to 2.0 moles, preferably 0.1 to 1.0 moles per one mole of the compound [II-A] or [III]. The reaction can be carried out at 0 to 150° C., preferably 20 to 80° C.

When $R^a$ in the compound [II-A] is hydrogen atom, the compound [I-A] can be prepared by converting the compound [II-A] to a corresponding reactive derivative (e.g., an acid halide, a mixed acid anhydride) and then reacting such reactive derivative with the compound [III] in the presence of the base in or without the solvent.

When $R^a$ in the compound [II-A] is an alkyl group or benzyl group, the present process A can be also carried out by converting the ester compound to a corresponding carboxylic acid compound of the following formula [II-Aa]:

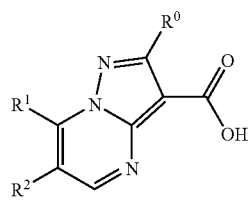

wherein the symbols are the same as defined above by a conventional manner such as hydrolysis, acidolysis with hydrochloric acid, formic acid, trifluoroacetic acid and the like or hydrogenation and then reacting the carboxylic acid compound [II-Aa] with the compound [III] in the same manner as described above.

(Method B)
Among the compounds [I] of the present invention, a compound in which E is a group of the formula: —$SO_2$— (compound [I-B]) can be prepared by, for example, reacting a sulfonylhalide compound of the formula [II-B]:

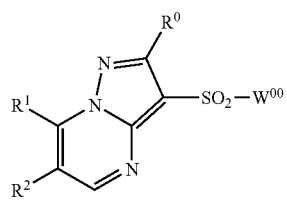

wherein $W^{00}$ is a halogen atom and the other symbols are the same as defined above with the amine compound [III]. The present reaction can be conducted in a solvent in the presence of a base. Examples of the solvent include any solvent which does not disturb the reaction, such as chloroform, dichloromethane, tetrahydrofuran and the like. Examples of the base include pyridine, triethylamine, diisopropylethylamine and the like. The amine compound [III] can be used in an amount of 0.5 to 5.0 moles, preferably 0.8 to 1.5 moles per one mole of the compound [II-B]. The base can be used in an amount of 1.0 to 5.0 moles, preferably 1.0 to 1.5 moles per one mole of the compound [II-B]. The reaction can be carried out at −10 to 100° C., preferably 0 to 40° C.

(Method C)
Among the compounds [I] of the present invention, a compound of the following formula [I-C]:

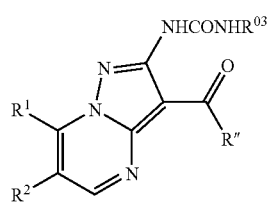

wherein the symbols are the same as defined above can be prepared by, for example, reacting a compound of the formula [II-C]:

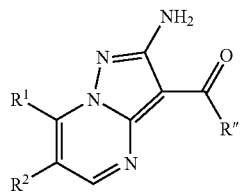

wherein the symbols are the same as defined above with an alkyl isocyanate compound of the following formula:

R$^{o3}$NCO wherein the symbol is the same as defined above without solvent. The alkyl isocyanate compound can be used, allowing for its function as solvent, in excessive moles per one mole of the compound [II-C]. The reaction can be carried out at 20 to 120° C., preferably 50 to 90° C. Meanwhile, other solvent such as chloroform, dichloromethane, tetrahydrofuran and the like may be used in the reaction.

The objective compound [I] of the present invention can be also prepared by, for example, converting the substituent(s) in $R^1$, $R^2$ and the like of such a compound [I] as obtained above to the other desired substituent(s). The intramolecular conversion processes can be selected according to the kinds of the objective substituents, and may be carried out, for example, in the following methods (a) to (h).

Method (a): A compound [I] having cyano group (or a cyano-containing group) as a substituent can be obtained by reacting a corresponding compound [I] having a halogen atom or an alkylsulfonyl group (or a halogen- or alkylsulfonyl-containing group) as a substituent with cyanide compound (e.g., zinc cyanide, copper cyanide, trimethylsilyl cyanide, potassium cyanide and the like) in the presence or absence of a catalyst, a base and an additive. Examples of the base include triethylamine, N-methylpiperidine, diisopropylethylamine and the like. Examples of said catalyst include a palladium catalyst such as palladium acetate, tris(dibenzylidene-acetone)dipalladium, trans-dichlorobis-(tricyclohexylphosphine)palladium, tetrakis-(triphenylphosphine)palladium and the like, a nickel catalyst such as dibromobis-(triphenylphosphine)nickel and the like. Examples of the additive include a phosphine compound such as 1,1'-bis-(diphenylphosphino)ferrocene, racemic 2,2'-bis-(diphenyl-phosphino)-1,1-binaphthyl, 2-(di-tert-butylphosphino)biphenyl, 2-(dicyclohexyl-phosphino)biphenyl, 2-dicyclohexylphosphino-2'-(N,N'-dimethylamino)biphenyl, tri-tert-butylphospine and the like.

Method (b): A compound [I] having an alkylamino group or a cycloalkylamino group (or an alkylamino- or cycloalkylamino-containing group) as a substituent can be obtained by reacting a corresponding compound [I] having a halogen atom (or a halogen-containing group) as a substituent with a mono- or di-alkylamine or a cycloalkylamine in an appropriate solvent in the presence of a catalyst, an additive and a base. Examples of the catalyst may be the palladium compounds or copper compounds used in Method (a). Examples of the additive may be the phosphine compounds used in Method (a). Examples of the base include potassium acetate, potassium carbonate, cesium carbonate, potassium tert-butoxide and the like.

Method (c): A compound [I] having an alkyloxy group (or a an alkyloxy-containing group) as a substituent can be obtained by, for example, (i) reacting a corresponding compound [I] having hydroxyl group (or a hydroxy-containing group) as a substituent with an alkyl halide in a solvent, or (ii) reacting a corresponding compound [I] having hydroxyl group (or a hydroxyl-containing group) as a substituent with an alkanol in a solvent in the presence of a base (e.g., potassium carbonate, cesium carbonate, sodium hydride and the like) or an activating agent (e.g., diethyl azodicarboxylate and the like) and in the presence of a tri-substituted phosphine or (iii) reacting a corresponding compound [I] having an alkylsulfonyl group (or an alkylsulfonyl-containing group) as a substituent with an alkali metal alkoxide in an appropriate solvent.

Method (d): A compound [I] having an alkylsulfinyl group or an alkylsulfonyl group (or an alkylsulfinyl- or alkylsulfonyl-containing group) as a substituent can be obtained by reacting a corresponding compound [I] having an alkylthio group (or an alkylthio-containing group) as a substituent with an oxidizing agent such as 3-chloroperbenzoic acid in an appropriate solvent.

Method (e): A compound [I] having an acylamino group such as an alkylcarbonylamino group (or an acylamino-containing group) as a substituent can be obtained by reacting a corresponding compound [I] having an amino group (or an amino-containing group) as a substituent with a carboxylic acid compound of the following formula:

R$^X$—COOH [Ac-1]

wherein $R^X$ is the same as defined above or a reactive derivative thereof (e.g., a corresponding acid anhydride or a corresponding acid halide). The present reaction can be carried out in a solvent in the presence of a base such as triethylamine and the like or a condensing agent such as water-soluble carbodiimide and in the presence or absence of an activating agent such as 1-hydroxybenzotriazole. Besides, such acyl group can be removed, in accordance with the kind of said acyl group, by a conventional manner such as acid treatment or catalytic hydrogenation.

Method (f): A compound [I] having a substituted or unsubstituted carbamoyl group of the formula: —CON(R$^e$)(R$^f$) (or a substituted or unsubstituted carbamoyl-containing group) as a substituent can be obtained by reacting a corresponding compound [I] having carboxyl group or an alkyloxycarbonyl group (or a carboxyl- or alkyloxycarbonyl-containing group) as a substituent with an amine compound of the formula: HN(R$^e$)(R$^f$) such as ammonia, a mono- or di-alkylamine and the like in an appropriate solvent.

Method (g): A compound [I] having an alkylcarbamoylamino group (or an alkylcarbamoylamino-containing group) as a substituent can be obtained by reacting a corresponding compound [I] having an amino group (or an amino-containing group) as a substituent with an alkyl isocyanate in an appropriate solvent.

Method (h): A compound [I] having a group of the formula:

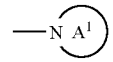

wherein Ring $A^1$ is a 5- to 7-membered nitrogen-containing aliphatic heteromonocyclic group as a substituent can be obtained by reacting a corresponding compound [I] having an amino group as a substituent with a compound of the formula:

X$^{o1}$-Alk$^1$-X$^{o2}$ wherein $X^{01}$ and $X^{02}$ are a halogen atom and $Alk^1$ is an alkylene group in a solvent such as acetonitrile in the presence of a base such as potassium carbonate and in the presence or absence of an additive such as sodium iodide. Examples of such nitrogen-containing aliphatic heterocyclic group include 1-pyrrolidinyl group, 1-piperidyl group and the like.

Method (i): A compound [I] having carboxyl group (or a carboxy-containing group) as a substituent can be obtained by treating a corresponding compound [I] having hydroxymethyl group (or a hydroxymethyl-containing group) as a substituent with an oxidizing agent such as pyridinium dichromate in an appropriate solvent.

If necessary, the compounds [I] of the present invention obtained in the aforementioned Processes can be converted to a pharmaceutically acceptable salt thereof by a conventional manner.

[Preparation of Intermediate Compound]

(i) Among the intermediate compounds [II-A] in the present invention, a compound of the following formula [II-A1]:

wherein the symbols are the same as defined above can be prepared in a manner as described in the following reaction scheme A1 to A3.

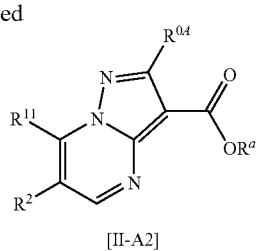

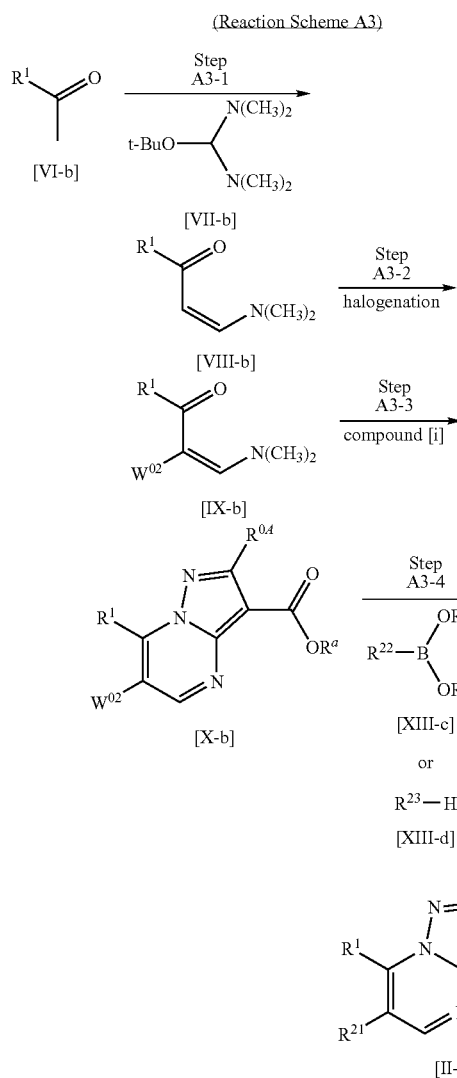

In the above-mentioned reaction scheme A1 to A3, $R^{001}$ is an alkyl group, $R^{11}$ and $R^{21}$ are each an optionally substituted aryl group, an optionally substituted heteroaryl group or an optionally substituted nitrogen-containing aliphatic heterocyclic group, $R^{12}$ and $R^{22}$ are each an optionally substituted aryl group or an optionally substituted heteroaryl group, $R^{13}$ and $R^{23}$ are each an optionally substituted nitrogen-containing aliphatic heterocyclic group, $R^{002}$ and $R^{003}$ are the same or different and each hydrogen atom or an alkyl group or both of them combine each other to form an alkylene group, t-Bu is tert-butyl group, $W^{01}$ and $W^{02}$ are each a halogen atom and the other symbols are the same as defined above.

Examples of the aryl group in $R^{11}$, $R^{12}$, $R^{21}$ or $R^{22}$ include a 6- to 10-membered mono- or bicyclic aryl group such as phenyl group or a naphthyl group. Among them, phenyl group is preferable.

Examples of the heteroaryl group in $R^{11}$, $R^{12}$, $R^{21}$ or $R^{22}$ include a 5- to 10-membered mono- or bicyclic heteroaryl group having one to three heteroatom(s) selected from oxygen atom, sulfur atom and nitrogen atom. Among them, a furyl group, a thienyl group or a pyridyl group is preferable.

Examples of the nitrogen-containing aliphatic heterocyclic group in $R^{11}$, $R^{12}$, $R^{21}$ or $R^{22}$ include a 5- to 7-membered aliphatic heteromonocyclic group optionally having further one or two heteroatom(s) selected from oxygen atom, sulfur atom and nitrogen atom. Among them, a 1-pyrrolidinyl group, 1-piperidyl group, morpholino group or thiomorpholino group is preferable.

Each of the aryl group, heteroaryl group or nitrogen-containing aliphatic heterocyclic group in $R^{11}$, $R^{12}$, $R^{21}$ or $R^{22}$ may be substituted by one to three group(s) selected from a halogen atom, cyano group, an alkyl group optionally substituted by one to three halogen atom(s), an alkyloxy group optionally substituted by one to three halogen atom(s) and an alkylsulfonyl group.

The alkylene group formed by combining $R^{002}$ with $R^{003}$ may be a straight or branched chain $C_{2-6}$ alkylene group such as ethylene group, trimethylene group or 1,1,2,2-tetramethylethylene group. Example of the substituent of said alkylene group include an alkyl group such as methyl group.

Each reaction described in the above-mentioned scheme A1 to A3 can be carried out, for example, in accordance with the manner as illustrated bellow.

Step A1-1:

The reaction of the compound [VI] with the compound [VII] can be carried out in an appropriate solvent under heating. Examples of the solvent include any solvent which does not disturb the reaction, such as dimethylformamide, dimethylacetamide, dioxane, 1,2-dichloroethane, toluene, xylene and the like. The compound [VII] can be used in an amount of 1.0 to 10 moles, preferably 1.0 to 3.0 moles per one mole of the compound [VI]. The reaction can be carried out at 50 to 200° C., preferably 80 to 150° C.

Step A1-2:

The reaction of the compound [VIII] with the compound [i] can be conducted in an appropriate solvent in the presence or absence of a base. Examples of the base include piperidine, morpholine, N-methylpiperazine, diethylamine and the like. Examples of the solvent include any solvent which does not disturb the reaction, such as acetic acid, methanol, ethanol, isopropanol, ethyleneglycol and the like. The compound [i] can be used in an amount of 0.5 to 2.0 moles, preferably 0.8 to 1.2 moles per one mole of the compound [VIII]. The base can be used in an amount of 0.01 to 2.0 moles, preferably 0.1 to 1.0 moles per one mole of the compound [VIII]. The reaction can be carried out at 50 to 150° C., preferably 70 to 100° C.

Besides, the present reaction can be carried out in a solvent in the presence or absence of an acid. Examples of the acid include hydrobromic acid, hydrochloric acid, acetic acid and the like. Examples of the solvent include any solvent which does not disturb the reaction, such as acetic acid, methanol, ethanol, isopropanol, ethyleneglycol and the like. The compound [i] can be used in an amount of 0.5 to 2.0 moles, preferably 0.8 to 1.2 moles per one mole of the compound [VIII]. The acid can be used in an amount of 0.1 to 3.0 moles, preferably 0.3 to 1.0 moles per one mole of the compound [VIII]. The reaction can be carried out at 0 to 150° C., preferably 60 to 100° C.

Step A2-1:

The reaction of the compound [VI-a] with the compound [VII] can be carried out in the same manner as described in Step A1-1.

Step A2-2:

The reaction of compound [VIII-a] with compound [i] can be carried out in the same manner as described in Step A1-2. Besides, the compound [X-a] can be obtained without conducting the next step A2-3, when the present reaction is conducted in the presence of acetic acid.

Step A2-3:

The intramolecular cyclization of the compound [IX-a] can be carried out in a solvent in the presence of a base. Examples of the solvent include any solvent which does not disturb the reaction, such as ethanol, acetonitrile, chloroform, tetrahydrofuran, dioxane, toluene, N,N-dimethylformamide and the like. Examples of the base include sodium carbonate, cesium carbonate, triethylamine, diisopropylethylamine, dimethylaminopyridine and the like. The base can be used in an amount of 0.1 to 10.0 moles, preferably 1.2 to 3.0 moles per one mole of the compound [IX-a]. The reaction can be carried out at 30 to 150° C., preferably 60 to 100° C.

Step A2-4:

The conversion of the compound [X-a] to the compound [XII-a] can be carried out in a solvent in the presence of a halogenating agent and in the presence or absence of a base. Examples of the solvent include any solvent which does not disturb the reaction, such as acetonitrile, chloroform, tetrahydrofuran, dioxane, toluene, N,N-dimethylformamide and the like. Examples of the halogenating agent include phosphorus oxychloride, thionyl chloride, phosphorus pentachloride, oxalyl chloride and the like. Examples of the base include N,N-dimethylaniline, diisopropylethyl-amine, N-methylmorpholine and the like. The halogenating agent can be used in an amount of 1.1 to 5.0 moles, preferably 1.2 to 1.5 moles per one mole of the compound [X-a]. The base can be used in an amount of 1.2 to 10.0 moles, preferably 1.5 to 2.0 moles per one mole of the compound [X-a]. The reaction can be carried out at 50 to 200° C., preferably 80 to 150° C.

Step A2-5:

(1) The reaction of the compound [XII-a] with the boronic acid compound [XIII-a] can be carried out in a solvent in the presence of a catalyst and a base. Examples of the boronic acid compound [XIII-a] include a compound in which $R^{002}$ and $R^{003}$ are each a hydrogen atom or an alkyl group such as methyl group, ethyl group, isopropyl group and the like, or both $R^{002}$ and $R^{003}$ combine each other to form an alkylene group such as ethylene group, propylene group, 1,1,2,2-tetramethylethylene group and the like. Among them, a preferable example includes a compound [XIII-a] in which $R^{002}$ and $R^{003}$ are each hydrogen atom or a corresponding boroxin compound of the following formula:

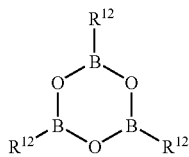

wherein the symbols are the same as defined above. Examples of the solvent include any solvent which does not disturb the reaction, such as dioxane, toluene, dimethoxyethane, ethanol, N,N-dimethylformamide, tetrahydrofuran, water and the like. Examples of the catalyst include a palladium catalyst such as tetrakis(triphenyl-phosphine)palladium (0), palladium (II) acetate, bis(dibenzylideneacetone)palladium (0), bis(triphenyl-phosphine)palladium (II) dichloride, bis(tri-o-tolylphosphine)palladium (II) dichloride, bis(tricyclohexylphosphine)palladium (II) dichloride or [1,1'-bis(diphenylphosphino)ferrocene]palladium (II) dichloride, a nickel catalyst such as 1,3-bis(diphenylphosphino)propane nickel (II) dichloride or bis(triphenylphosphine) nickel (II) dichloride and the like. Examples of the base include potassium phosphate, sodium carbonate, cesium carbonate, sodium hydrogencarbonate, potassium fluoride, triethylamine, lithium chloride and the like. The compound [XIII-a] can be used in an amount of 1.0 to 5.0 moles, preferably 1.1 to 2.0 moles per one mole of the compound [XII-a]. The catalyst can be used in an amount of 0.001 to 0.5 moles, preferably 0.01 to 0.05 moles per one mole of the compound [XII-a]. The base can be used in an amount of 1.0 to 10.0 moles, preferably 2.0 to 5.0 moles per one mole of the compound [XII-a]. The reaction can be carried out at 20 to 150° C., preferably 60 to 120° C.

(2) The reaction of the compound [XII-a] with the nitrogen-containing heterocyclic compound [XIII-b] can be carried out in a solvent in the presence of a base. Examples of the solvent include any solvent which does not disturb the reaction, such as N,N-dimethylformamide, toluene, dioxane, tetrahydrofuran and the like. Examples of the base include potassium carbonate, sodium carbonate, cesium carbonate, sodium hydrogencarbonate, potassium fluoride, triethylamine, diisopropylethylamine, dimethylaminopyridine and the like. The compound [XIII-b] can be used in an amount of 0.8 to 5.0 moles, preferably 1.0 to 1.5 moles per one mole of the compound [XII-a]. The base can be used in an amount of 1.0 to 10.0 moles, preferably 2.0 to 5.0 moles per one mole of the compound [XII-a]. The reaction can be carried out at 80 to 200° C., preferably 120 to 180° C.

Step A3-1:

The reaction of the compound [VI-b] with the compound [VII-b] can be carried out in a solvent or without any solvent. Examples of the solvent include any solvent which does not disturb the reaction, such as dimethylformamide, toluene, dioxane, tetrahydrofuran, dimethoxyethane and the like. The compound [VII-b] can be used in an amount of 0.5 to 5.0 moles, preferably 0.9 to 1.5 moles per one mole of the compound [VI-b]. The reaction can be carried out at 0 to 150° C., preferably 50 to 80° C.

Step A3-2:

The halogenation of the compound [VIII-b] can be carried out in a solvent in the presence of a halogenating agent and in the presence or absence of a base. Examples of the solvent include any solvent which does not disturb the reaction, such as methylene chloride, carbon tetrachloride, chloroform, acetic acid, tetrahydrofuran and the like. Examples of the halogenating agent include bromine, N-bromosuccinimide, N-chlorosuccinimide and the like. Examples of the base include triethylamine, diisopropylethylamine, potassium carbonate, sodium carbonate and the like. The halogenating agent can be used in an amount of 0.5 to 10.0 moles, preferably 1.0 to 3.0 moles per one mole of the compound [VIII-b]. The reaction can be carried out at −40 to 100° C., preferably −5 to 20° C.

Step A3-3:

The reaction of the compound [IX-b] with the compound [i] can be carried out in the same manner as described in Step A1-2.

Step A3-4:

The reaction of the compound [X-b] with the boronic acid compound [XIII-c] or the nitrogen-containing heterocyclic compound [XIII-d] can be carried out in the same manner as described in Step A2-5 (1) or (2), respectively.

(ii) Among the intermediate compounds [II-A], a compound of the following formula [II-A3]:

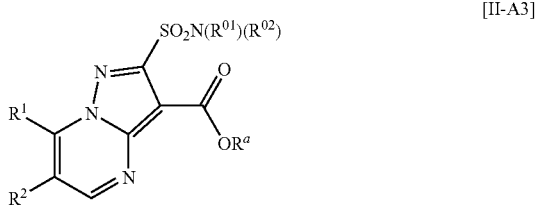

[II-A3]

wherein the symbols are the same as defined above can be prepared in accordance with the following reaction scheme A4.

(Reaction scheme A4)

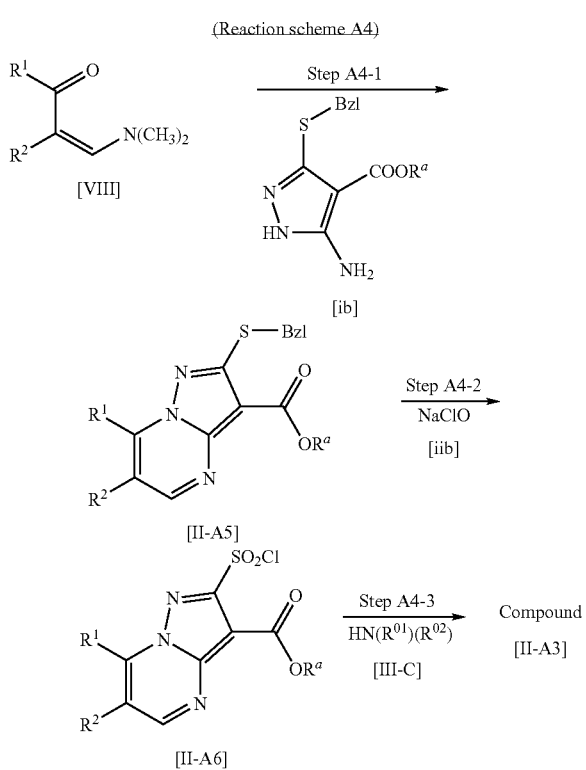

In the above reaction scheme, Bzl is benzyl group and the other symbols are the same as defined above.

Each reaction described in the above-mentioned scheme A4 can be carried out, for example, in accordance with the manner as illustrated bellow.

Step A4-1:
The present reaction can be carried out in the same manner as described in Step A1-2.

Step A4-2:
The reaction of the compound [II-A5] with sodium chlorite can be carried out in a solvent in the presence of an acid such as concentrated hydrochloric acid. Examples of the solvent include any solvent which does not disturb the reaction, such as methylene chloride, chloroform and the like. The sodium chlorite can be used in an amount of 0.5 to 10.0 moles, preferably 1.0 to 3.0 moles per one mole of the compound [II-A5]. The reaction can be carried out at −40 to 100° C., preferably −5 to 20° C.

Step A4-3:
The reaction of the compound [II-A6] with the compound [III-C] can be carried out in the same manner as described in Method B.

(iii) Among the intermediate compounds [II-A], a compound in which $R^0$ is a hydroxyalkyl group can be prepared by, for example, treating a corresponding compound in which $R^0$ is an alkyl group with a brominating agent such as N-bromosuccinimide in a solvent such as carbon tetrachloride, and then reacting the thus-obtained product with an acetate compound such as potassium acetate in a solvent such as dimethylformamide, and further treating the reaction product with a base (e.g., an alkali metal alkoxide such as sodium ethoxide) in a solvent such as a mixture of ethanol and tetrahydrofuran.

(iv) The above-mentioned intermediate compound [II-B] can be prepared by, for example, reacting a compound of the following formula [II-C]:

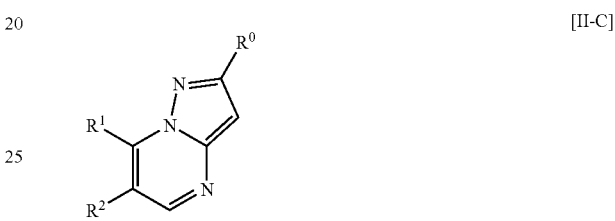

[II-C]

wherein the symbols are the same as defined above with a halogenosulfonate compound of the formula [XIV]:

Hal-SO$_3$H  [XIV]

wherein Hal is a halogen atom in a solvent such as chloroform and then treating the reaction product with a halogenating agent (e.g., thionyl halide such as thionyl chloride).

Throughout the present description and claims, the "halogen atom" means fluorine, chlorine, iodine or bromine atom. The "alkyl group" means a straight or branched chain alkyl group having 1 to 8 carbon atoms, preferably 1 to 6 carbon atoms. The "cycloalkyl group" means a cycloalkyl group having 3 to 8 carbon atoms, preferably 5 to 7 carbon atoms. The "alkylene group" means a straight or branched chain alkylene group having 1 to 8 carbon atoms, preferably 1 to 6 carbon atoms.

EXAMPLES

The compounds of the present invention are illustrated in more detail by the following examples but should not be construed to be limited thereto.

Example A1

To a solution of 3-carboxy-6-(2-chlorophenyl)-7-(4-chlorophenyl)pyrazolo-[1,5-a]pyrimidine (compound obtained in Reference Example 1-(4); 58 mg) and 1-cyanocyclohexylamine hydrochloride (25 mg) in chloroform (1.0 mL containing amylene) were added a 0.5 M solution of 1-hydroxybenzotriazole monohydrate in chloroform (0.45 mL containing amylene), a 0.5 M solution of 1-(3-dimethylamino-propyl)-3-ethylcarbodiimide hydrochloride in N,N-dimethylformamide (0.45 mL) and triethylamine (63 μL), and the mixture was stirred at room temperature overnight. To the reaction mixture were added an aqueous saturated sodium hydrogencarbonate solution (2 mL), water (2 mL) and chloroform (4 mL), and the mixture was vigorously stirred for 15 minutes. The organic layer was separated, and the aqueous layer was extracted with chloroform (3 mL). The combined organic layer was washed successively with an aqueous saturated sodium hydrogencarbonate solution (3 mL) and brine (3 mL) and concentrated in vacuo. The resultant crude product was purified by liquid chromatograph-mass spectrometer (LCMS, column; XTerra MS C18, solvent; 10 mM ammonium carbonate/methanol 40/60 to 10/90) and lyophilized to give 6-(2-chlorophenyl)-7-(4-chlorophenyl)-3-[N-(1-cyanocyclohexyl)carbamoyl]pyrazolo[1,5-a]pyrimidine (15.6 mg; yield: 21%) as a powder.

MS (ESI) m/z; 490 [M+H]$^+$

Example A2

To a solution of the compound obtained in Example A1 (70 mg) in methylene chloride (1.0 mL) were added methanesulfonic acid (84 μL) and a few drops of water, and the mixture was stirred at room temperature overnight and at 35° C. for 4 hours. To the reaction mixture was added successively an aqueous saturated sodium hydrogencarbonate solution and methylene chloride. After stirring, the organic layer was separated and concentrated in vacuo. The resultant crude product was purified by column chromatography on silica gel (solvent; chloroform/methanol=100/0 to 95/5) to give 3-[N-(1-carbamoylcyclohexyl)carbamoyl]-6-(2-chlorophenyl)-7-(4-chlorophenyl)-pyrazolo[1,5-a]pyrimidine (18 mg; yield: 25%) as a pale yellow solid.

MS (APCI) m/z; 508/510 [M+H]$^+$

Example A3

(1) The compound obtained in Reference Example 1-(4) (77 mg) and 4-amino-4-cyanotetrahydrothiopyrane hydrochloride (compound obtained in Reference Example A3-(1); 34 mg) were treated in the same manner as described in Example A1 to give 6-(2-chlorophenyl)-7-(4-chlorophenyl)-3-[N-(4-cyanotetrahydrothiopyran-4-yl)-carbamoyl]-pyrazolo[1,5-a]pyrimidine (50.8 mg; yield: 50%) as a powder.

MS (APCI) m/z; 508/510 [M+H]$^+$ (2) The compound obtained in the above step (1) (47 mg) was dissolved in methylene chloride/methanesulfonic acid (1 mL/18 μL), and thereto was added m-chloroperbenzoic acid (75%, 53 mg). The mixture was stirred at room temperature for 3 hours. To the reaction mixture was added an aqueous saturated sodium hydrogencarbonate solution. After stirring, the organic layer was separated and concentrated in vacuo. The resultant crude product was purified by column chromatography on silica gel (solvent; chloroform/methanol=98/2 to 95/5) to give 3-[N-(4-carbamoyl-1,1-dioxo-tetrahydrothiopyran-4-yl)carbamoyl]-6-(2-chlorophenyl)-7-(4-chlorophenyl)pyrazolo[1,5-a]pyrimidine (18 mg; yield: 35%) as a solid.

MS (APCI) m/z; 558/560 [M+H]$^+$

Example A4

(1) To a solution of the compound obtained in Reference Example 1-(4) (300 mg) and 1-methoxycarbonylcyclohexylamine hydrochloride (181 mg) in dichloromethane (4 mL) were added 1-hydroxybenzotriazole monohydrate (179 mg), 1-(3-dimethylaminopropyl)-3-ethylcarbodiimide hydrochloride (224 mg) and triethylamine (328 μL), and the mixture was stirred at room temperature overnight. To the reaction mixture were added methylene chloride and an aqueous saturated sodium hydrogencarbonate solution. After stirring vigorously for 10 minutes, the organic layer was separated and concentrated in vacuo. The resultant crude product was purified by column chromatography on NH-silica gel (Chromatorex NH silica gel, Fuji Silicia Chem., solvent; hexane/ethyl acetate=70/30 to 50/50) to give 6-(2-chlorophenyl)-7-(4-chlorophenyl)-3-[N-(1-methoxycarbonylcyclohexyl)carbamoyl]pyrazolo[1,5-a]pyrimidine (380 mg; yield: 93%)

MS (APCI) m/z; 523/525 [M+H]$^+$ (2) To a solution of the compound obtained in the above step (1) (200 mg) in ethanol (2 mL) was added an aqueous 2 N sodium hydroxide solution (0.38 mL), and the mixture was stirred at room temperature overnight and at 50° C. for 5 hours. After cooling to room temperature, to the reaction mixture were added successively an aqueous 2 N hydrochloric acid solution (0.38 mL), brine and methylene chloride. The organic layer was separated and concentrated in vacuo. The resultant crude product was purified by column chromatography on silica gel (solvent; chloroform/methanol=99/1 to 92/8) to give 3-[N-(1-carboxycyclohexyl)carbamoyl]-6-(2-chlorophenyl)-7-(4-chlorophenyl)pyrazolo[1,5-a]pyrimidine (180 mg; yield: 92%) as a powder.

MS (APCI) m/z; 509/511 [M+H]$^+$

Example A5

To a solution of the compound obtained in Example A4 (50 mg) and methylamine hydrochloride (8 mg) in methylene chloride (1 mL) were added 1-hydroxybenzotriazole monohydrate (23 mg), 1-(3-dimethylaminopropyl)-3-ethyl-carbodiimide hydrochloride (29 mg) and triethylamine (21 μL), and the mixture was stirred at room temperature overnight. To the reaction mixture were added methylene chloride and an aqueous saturated sodium hydrogencarbonate solution. After stirring vigorously for 10 minutes, the organic layer was separated and concentrated in vacuo. The resultant crude product was purified by column chromatography on silica gel (solvent; chloroform/methanol=100/0 to 95/5) and triturated to give 6-(2-chlorophenyl)-7-(4-chlorophenyl)-3-[N-[1-(N-methylcarbamoyl)cyclohexyl]-carbamoyl]pyrazolo[1,5-a]pyrimidine (25 mg; yield: 61%)

MS (APCI) m/z; 522/524 [M+H]$^+$

Example A6

(1) The compound obtained in Reference Example A6 (2-amino-6-(2-chloro-phenyl)-3-ethoxycarbonyl)-7-(4-trifluoromethylphenyl)pyrazolo[1,5-a]pyrimidine, 3.0 g) was treated in the same manner as described in Reference Example A1-(4) to give 2-amino-3-carboxy-6-(2-chlorophenyl)-7-(4-trifluoromethylphenyl)pyrazolo[1,5-a]pyrimidine as a powder.

(2) The compound obtained in the above step (1) (200 mg) and 1-(2-pyridyl)ethylamine (73 mg) were treated in the same manner as described in Example A1 to give 2-amino-6-(2-chlorophenyl)-7-(4-trifluoromethylphenyl)-3-[N-[1-(2-pyridyl)ethyl]carbamoyl]pyrazolo[1,5-a]pyrimidine (112 mg, yield: 45%) as a powder.

(3) A mixture of the compound obtained in the above step (2) (59 mg), acetyl chloride (156 μL), triethylamine (304 μL) and tetrahydrofuran (5 mL) was stirred at 60° C. overnight. To the reaction mixture was added an aqueous saturated sodium hydrogencarbonate solution at 0° C. After stirring, the mixture was extracted with chloroform, and the extract was dried over magnesium sulfate and filtered. The filtrate was concentrated in vacuo, and the resultant crude product was purified by column chromatography on NH-silica gel (Chromatorex NH silica gel, solvent; hexane/ethyl acetate=50/50 to 30/70) to give 2-acetylamino-6-(2-chlorophenyl)-7-(4-trifluoromethylphenyl)-3-[N-[1-(2-pyridyl)ethyl]carbamoyl]pyrazolo[1,5-a]pyrimidine (50.8 mg; yield: 80%) as a pale yellow powder.

MS (APCI) m/z; 579/581 [M+H]$^+$

Example A7

(1) To a solution of the compound obtained in Reference Example A6 (2.1 g) in water/acetonitrile (21 mL/84 mL) were added 1,4-dichlorobutane (2.9 g), potassium carbonate (3.2 g) and sodium iodide (2.7 g), and the mixture was refluxed for 5 days. After cooling to room temperature, to the reaction mixture were added ethyl acetate and water. After stirring, the organic layer was separated, dried over magnesium sulfate and filtered. The filtrate was concentrated in vacuo, and the resultant crude product was purified by column chromatography on silica gel (solvent; hexane/ethyl acetate=85/15 to 70/30) to give 6-(2-chlorophenyl)-3-ethoxycarbonyl-7-(4-trifluoromethyl-phenyl)-2-(pyrrolidin-1-yl)pyrazolo[1,5-a]pyrimidine (0.61 g; yield: 26%) as a yellow oil.

MS (APCI) m/z; 515/517 [M+H]$^+$ (2) The compound obtained in the above step (1) (610 mg) was treated in the same manner as described in Reference Example A1-(4) to give 3-carboxy-6-(2-chloro-phenyl)-7-(4-trifluoromethylphenyl)-2-(pyrrolidin-1-yl)-pyrazolo[1,5-a]pyrimidine (449 mg), and then the compound (70 mg) was treated in the same manner as described in Example A1 to give 6-(2-chlorophenyl)-7-(4-trifluoromethylphenyl)-3-[N-[1-(2-pyridyl)ethyl]carbamoyl]-2-(pyrrolidin-1-yl)pyrazolo[1,5-a]pyrimidine (15.2 mg).

MS (APCI) m/z; 591/593 [M+H]$^+$

Example A8

(1) The compound obtained in Reference Example A11 (3-carboxy-7-(4-chloro-2-fluorophenyl)-6-(2-chlorophenyl)-pyrazolo[1,5-a]pyrimidine; 39 mg) and methyl 4-amino-1,1-dioxotetrahydrothiopyran-4-carboxylate (20 mg) were treated in the same manner as described in Example A1 to give 7-(4-chloro-2-fluorophenyl)-6-(2-chlorophenyl)-3-[N-(4-methoxycarbonyl-1,1-dioxotetrahydrothiopyran-4-yl)-carbamoyl]pyrazolo[1,5-a]pyrimidine (45 mg, yield: 79%) as a pale yellow powder.

MS (APCI) m/z; 591/593 [M+H]$^+$ (2) The compound obtained in the above step (1) (352 mg) was treated in the same manner as described in Example A4-(2) to give 3-[N-(4-carboxy-1,1-dioxo-tetrahydrothiopyran-4-yl)carbamoyl]-7-(4-chloro-2-fluorophenyl)-6-(2-chlorophenyl)pyrazolo[1,5-a]pyrimidine (301 mg, yield: 88%) as a pale yellow powder.

MS (APCI) m/z; 577/579, [M+H]$^+$ (3) The compound obtained in the above step (2) (70 mg) and ammonium chloride (32 mg) were treated in the same manner as described in Example A1 to give 3-[N-(4-carbamoyl-1,1-dioxotetrahydrothiopyran-4-yl)carbamoyl]-7-(4-chloro-2-fluoro-phenyl)-6-(2-chlorophenyl)pyrazolo[1,5-a]pyrimidine (40 mg, yield: 57%) as a pale yellow powder.

MS (APCI) m/z; 576/578 [M+H]$^+$

Examples A9 to A15

The corresponding starting materials were treated in the same manner as described in Example A1 to give compounds as shown in the following Table 1.

TABLE 1

(No. 1)

| Ex. Nos. | R' | R$^0$ | R | Physicochemical properties etc. |
|---|---|---|---|---|
| A9 | Cl | H | NC-cyclopentyl | solid<br>MS (ESI): 476 [M + H]$^+$ |
| A10 | Cl | H | H$_3$C-cyclohexyl | solid<br>MS (ESI): 479 [M + H]$^+$ |
| A11 | Cl | H | H$_3$C-cyclopropyl | solid<br>MS (ESI): 437 [M + H]$^+$ |
| A12 | CF$_3$ | CH$_3$ | NC-cyclopentyl | powder<br>MS (APCI): 524/526 [M + H]$^+$ |
| A13 | CF$_3$ | CH$_3$ | cyclohexyl-CN | powder<br>MS (APCI): 538/540 [M + H]$^+$ |

(No. 2)

| Ex. Nos. | R' | R | Physicochemical properties etc. |
|---|---|---|---|
| A14 | H | H$_3$C-C(CH$_3$)-pyridyl | powder<br>MS (APCI): 502/504 [M + H]$^+$ |
| A15 | F | CH(CH$_3$)-pyridyl | powder<br>MS (APCI): 506/508 [M + H]$^+$ |

Examples A16 to A18

The corresponding starting materials were treated in the same manner as described in Example A5 to give compounds as shown in the following Table 2.

TABLE 2

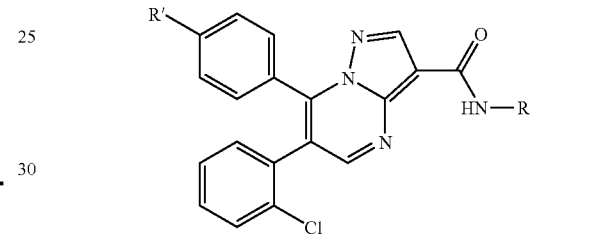

| Ex. Nos. | R' | R | Physicochemical properties etc. |
|---|---|---|---|
| A16 | Cl | (H₃C)₂N-C(=O)-C(CH₃)(cyclohexyl) | powder MS (APCI): 491/493 [M + H]⁺ |
| A17 | CF₃ | H₂N-C(=O)-C(CH₃)(tetrahydrothiopyran-SO₂) | powder MS (APCI): 592/594 [M + H]⁺ |
| A18 | Cl | (H₃C)₂N-CH₂CH₂-NH-C(=O)-C(CH₃)(cyclohexyl) | powder MS (APCI): 579/581 [M + H]⁺ |

Examples A19 to A30

The corresponding starting materials were treated in the same manner as described in Example A4 to give compounds as shown in the following Table 3.

TABLE 3

(No. 1)

| Ex. Nos. | R' | R⁰ | R | Physicochemical properties etc. |
|---|---|---|---|---|
| A19 | Cl | H | CH(CH₃)(CH(CH₃)₂)-COOH type (iPr-CH-COOH) | powder MS (APCI): 483/485 [M + H]⁺ |
| A20 | CF₃ | H | CH(CH₂Ph)-COOH | powder MS (APCI): 565/567 [M + H]⁺ |

TABLE 3-continued

| Ex. Nos. | R' | R⁰ | R | Physicochemical properties etc. |
|---|---|---|---|---|
| A21 | CF₃ | H | CH(iPr)-COOH | powder MS (APCI): 517/519 [M + H]⁺ |
| A22 | CF₃ | H | CH(Ph)(CH₃)-... -COOH | powder MS (APCI): 551/553 [M + H]⁺ |
| A23 | Cl | CH₃ | CH(iPr)-COOH | powder MS (APCI): 497/499 [M + H]⁺ |
| A24 | Cl | CH₃ | C(CH₃)₂-COOH | powder MS (APCI): 483/485 [M + H]⁺ |

(No. 2)

| Ex. Nos. | R' | R | Physicochemical properties etc. |
|---|---|---|---|
| A25 | Cl | CH(CH₃)(Ph) with HOOC | powder MS (APCI): 517/519 [M + H]⁺ |
| A26 | CF₃ | C(CH₃)₂-COOH | powder MS (APCI): 503/505 [M + H]⁺ |
| A27 | Cl | CH(CH₃)(CH₂Ph)-COOH | powder MS (APCI): 531/533 [M + H]⁺ |
| A28 | CF₃ | trans-4-methylcyclohexane-COOH | powder MS (APCI): 543/545 [M + H]⁺ |
| A29 | CF₃ | 4-ethylphenyl-COOH | powder MS (APCI): 551/553 [M + H]⁺ |
| A30 | CF₃ | 3-ethylphenyl-COOH | powder MS (APCI): 551/553 [M + H]⁺ |

Examples A31 to A32

The corresponding starting materials were treated in the same manner as described in Example A1 to give compounds as shown in the following Table 4.

TABLE 4

[Structure: pyrazolo[1,5-a]pyrimidine core with 4-(trifluoromethyl)phenyl, 2-chlorophenyl substituents and a C(O)NH-R group]

| Ex. Nos. | R | Physicochemical properties etc. |
|---|---|---|
| A31 | 1-cyano-cyclohexyl (NC-C(cyclohexyl)) | powder<br>MS (APCI): 524/526 [M+H]+ |
| A32 | 2-(2-pyridyl)propan-2-yl (H3C-C(CH3)-2-pyridyl) | powder<br>MS (APCI): 536/538 [M+H]+ |

Examples A34

(1) The corresponding starting materials were treated in the same manner as described in Reference Example A6 to give 2-amino-6-(2-chlorophenyl)-7-(4-chloro-phenyl)-3-ethoxy-carbonylpyrazolo[1,5-a]pyrimidine as a yellow powder.

MS (APCI) m/z, —-427/429 [M+H]+

(2) To a solution of the compound obtained in the above step (1) (2.64 g) in tetrahydrofuran (50 mL) were added triethylamine (5.17 mL) and methanesulfonyl chloride (2.83 g) at 0° C., and the mixture was stirred for 5 minutes at the same temperature and at room temperature for 1 hour. The reaction mixture was diluted with ethyl acetate, and thereto was added water at 0° C. After stirring, the organic layer was separated, and the aqueous layer was extracted with ethyl acetate. The combined organic layer was dried over magnesium sulfate and filtered. The filtrate was concentrated in vacuo, and the resultant crude product was purified by column chromatography on NH-silica gel (Chromatorex NH silica gel, solvent; chloroform) to give 6-(2-chlorophenyl)-7-(4-chlorophenyl)-3-ethoxycarbonyl-2-[bis(methylsulfonyl)-amino]pyrazolo[1,5-a]pyrimidine (2.91 g, yield: 81%) as a pale yellow solid.

MS (APCI) m/z; 583/585 [M+H]+

(3) To a solution of the compound obtained in the above step (2) (2.91 g) in tetrahydrofuran (60 mL) were added tetrabutylammonium fluoride trihydrate (3.15 g), and the mixture was stirred at room temperature for 30 minutes. To the reaction mixture was added water, and the mixture was stirred. The organic layer was separated, and the aqueous layer was extracted with chloroform. The combined organic layer was concentrated in vacuo, and the resultant crude product was purified by column chromatography on silica gel (solvent; hexane/ethyl acetate=70/30 to 50/50) to give 6-(2-chlorophenyl)-7-(4-chlorophenyl)-3-ethoxycarbonyl-2-(methylsulfonyl-amino)pyrazolo[1,5-a]pyrimidine (2.20 g, yield: 87%) as a pale yellow solid.

MS (APCI) m/z; 505/507 [M+H]+

(4) To a solution of the compound obtained in the above step (3) (0.8 g) in ethanol/tetrahydrofuran (10 mL/20 mL) was added an aqueous 2 N sodium hydroxide solution (4.8 mL), and the mixture was stirred at 40° C. overnight. The precipitates were collected by filtration to give 3-carboxy--(2-chlorophenyl)-7-(4-chlorophenyl)-2-(methylsulfonylamino)pyrazolo[1,5-a]pyrimidine (0.86 g) as a crude product.

MS (APCI) m/z; 477/479 [M+H]+

(5) The compound obtained in the above step (4) (70 mg) and 1-(2-pyridyl)-ethylamine (23 mg) were treated in the same manner as described in Example A1 to give 6-(2-chlorophenyl)-7-(4-chlorophenyl)-2-(methylsulfonylamino)-3-[N-[1-(2-pyridyl)ethyl]carbamoyl]pyrazolo[1,5-a]pyrimidine (27 mg, yield: 32%) as a colorless powder.

MS (APCI) m/z; 581/583 [M+H]+

Example A35

(1) A mixture of the compound obtained in Example A34-(3) (1.0 g), sodium ethoxide (1.35 g) and ethanol (40 mL) was stirred at 80° C. for 10 minutes. Thereto was added dropwise methyl iodide (2.5 mL), and the mixture was stirred for 3 days. The reaction mixture was concentrated in vacuo, and to the residue were added water and ethyl acetate. The organic layer was separated, and the aqueous layer was extracted with ethyl acetate. The combined organic layer was dried over magnesium sulfate and filtered. The filtrate was concentrated in vacuo, and the resultant crude product was purified by column chromatography on NH-silica gel (Chromatorex NH silica gel, solvent; hexane/ethyl acetate 75/25 to 40/60) to give 6-(2-chlorophenyl)-7-(4-chlorophenyl)-3-ethoxycarbonyl-2-[N-methyl-N-(methylsulfonyl)amino]pyrazolo[1,5-a]pyrimidine (1.06 g, yield: 100%) as a colorless powder.

MS (APCI) m/z; 519/521 [M+H]+

(2) To a solution of the compound obtained in the above step (1) (1.06 g) in ethanol/tetrahydrofuran (15 mL/15 mL) was added an aqueous 2 N sodium hydroxide solution (4.1 mL), and the mixture was stirred at 40° C. overnight. The reaction mixture was acidified with an aqueous 2 N hydrochloric acid, concentrated in vacuo and extracted with chloroform. The organic layer was dried over magnesium sulfate and filtered. The filtrate was concentrated in vacuo, and the residue was triturated with diethylether to give 3-carboxy-6-(2-chlorophenyl)-7-(4-chlorophenyl)-2-[N-methyl-N-(methylsulfonyl)amino]-pyrazolo[1,5-a]pyrimidine (0.75 g, yield: 75%) as a pale yellow powder.

MS (APCI) m/z; 491/493 [M+H]+

(3) The compound obtained in the above step (2) (60 mg) and 1-(2-pyridyl)-ethylamine (19 mg) were treated in the same manner as described in Example A1 to give 6-(2-chlorophenyl)-7-(4-chlorophenyl)-2-[N-methyl-N-(methylsulfonyl)amino]-3-[N-[1-(2-pyridyl)ethyl]carbamoyl]-pyrazolo[1,5-a]pyrimidine (57 mg, yield: 79%) as a colorless powder.

MS (APCI) m/z; 595/597 [M+H]+

Examples A36 to A38

The corresponding starting materials were treated in the same manner as described in Example A1 to give compounds as shown in the following Table 5.

TABLE 5

| Ex. Nos. | R¹ | Physicochemical properties etc. |
|---|---|---|
| A36 | H₃C-[piperidine]- | powder MS (APCI): 489/491 [M + H]⁺ |
| A37 | H₃CO-[piperidine]- | powder MS (APCI): 505/507 [M + H]⁺ |
| A38 | H₃CO-[pyrrolidine]- | powder MS (APCI): 491/493 [M + H]⁺ |

Example A39

To a solution of the compound obtained in Reference Example A9 (159 mg) and pyridine (83 μL) in chloroform (5 mL) was added dropwise a solution of the compound obtained in Reference Example A17 (200 mg) in chloroform (2 mL) under ice-cooling, and the mixture was stirred at room temperature for 17 hours. To the reaction mixture was added water, and the mixture was extracted with chloroform. The organic layer was concentrated in vacuo and the resultant crude product was purified by column chromatography on silica gel (solvent; hexane/ethyl acetate=80/20 to 65/35) to give 6-(2-chlorophenyl)-7-(4-trifluoromethylphenyl)-3-[N-(1-methoxy-carbonylcyclohexyl)-sulfamoyl]-2-methylpyrazolo[1,5-a]pyrimidine (205 mg, yield: 82%) as a powder.

MS (APCI) m/z; 607/609 [M+H]⁺

Example A40

To a solution of the compound obtained in Example A39 (190 mg) in methanol (2 mL) was added an aqueous 2 N sodium hydroxide solution (0.39 mL), and the mixture was stirred at 70° C. for 15 hours. After cooling to room temperature, to the reaction mixture was added an aqueous 2 N hydrochloric acid (400 μL), and the mixture was diluted with water. The precipitates were collected by filtration to give 3-[N-(1-carboxycyclohexyl)sulfamoyl]-6-(2-chlorophenyl)-7-(4-trifluoromethylphenyl)-2-methylpyrazolo[1,5-a]pyrimidine (150 mg, yield: 81%) as a powder.

MS (APCI) m/z; 593/595 [M+H]⁺

Example A41

(1) The compound obtained in Reference Example A10 (200 mg) and the compound obtained in Reference Example B15 (63 mg) were treated in the same manner as described in Example A1 to give 6-(2-chlorophenyl)-7-(4-trifluoromethyl-phenyl)-3-[N-(4-methyl-tetrahydrothiopyran-4-yl)carbamoyl]-pyrazolo[1,5-a]pyrimidine 153 mg, yield: 48%) as a powder.

MS (APCI) m/z; 531/533 [M+H]⁺

(2) To a solution of the compound obtained in the above step (1) (95 mg) in methylene chloride (5 mL) was added m-chloroperbenzoic acid (75%, 123 mg) under ice-cooling and the mixture was stirred at room temperature for 21 hours. To the reaction mixture was added an aqueous saturated sodium hydrogencarbonate solution and the mixture was extracted with chloroform. The organic layer was concentrated in vacuo and the resultant crude product was purified by column chromatography on silica gel (solvent; hexane/ethyl acetate=80/20 to 60/40) to give 6-(2-chlorophenyl)-7-(4-trifluoromethylphenyl)-3-[N-(4-methyl-1,1-dioxotetrahydrothiopyran-4-yl)carbamoyl]-pyrazolo[1,5-a]pyrimidine (68 mg, yield: 68%) as a powder.

MS (APCI) m/z; 563/565 [M+H]⁺

Examples A42 to A49

The corresponding starting materials were treated in the same manner as described in Example A41 to give compounds as shown in the following Table 6.

TABLE 6

| Ex. Nos. | R' | R'' | R⁰ | R³ | Physicochemical properties etc. |
|---|---|---|---|---|---|
| A42 | Cl | H | CH₃ | CH₃ | powder MS (APCI): 543/545 [M + H]⁺ |
| A43 | CF₃ | H | CH₃ | CH₃ | powder MS (APCI): 577/579 [M + H]⁺ |
| A44 | Cl | F | CF₃ | CH₃ | powder MS (APCI): 615/617 [M + H]⁺ |
| A45 | Cl | H | CF₃ | CH₃ | powder MS (APCI): 597/599 [M + H]⁺ |
| A46 | Cl | H | —OC₂H₅ | CH₃ | powder MS (APCI): 573/575 [M + H]⁺ |
| A47 | CF₃ | F | H | CH₃ | powder MS (APCI): 581/583 [M + H]⁺ |
| A48 | Cl | F | CH₃ | CH₃ | powder MS (APCI): 561/563 [M + H]⁺ |
| A49 | CF₃ | H | H | COOCH₃ | powder MS (APCI): 607/609 [M + H]⁺ |

Examples A50 to A64

The corresponding starting materials were treated in the same manner as described in Example A1 to give compounds as shown in the following Table 7.

TABLE 7

(No. 1)

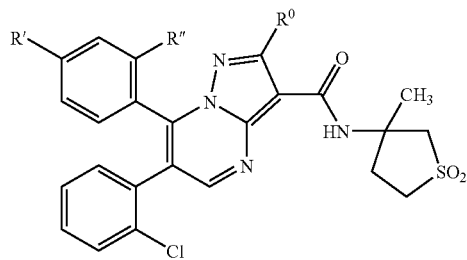

| Ex. Nos. | R' | R" | R⁰ | Physicochemical properties etc. |
|---|---|---|---|---|
| A50 | CHF$_2$ | F | H | powder<br>MS (ESI): 549 [M + H]$^+$ |
| A51 | Cl | H | CH$_3$ | powder<br>MS (ESI): 529 [M + H]$^+$ |
| A52 | CF$_3$ | H | H | powder<br>MS (ESI): 549 [M + H]$^+$ |
| A53 | CF$_3$ | H | CH$_3$ | powder<br>MS (ESI): 563 [M + H]$^+$ |
| A54 | CF$_3$ | H | CHF$_2$ | powder<br>MS (ESI): 599 [M + H]$^+$ |
| A55 | —N(CH$_3$)$_2$ | H | H | powder<br>MS (ESI): 524 [M + H]$^+$ |
| A56 | Cl | H | CF$_3$ | powder<br>MS (ESI): 583 [M + H]$^+$ |
| A57 | CF$_3$ | F | H | powder<br>MS (ESI): 567 [M + H]$^+$ |
| A58 | H | H | CH$_3$ | powder<br>MS (ESI): 495 [M + H]$^+$ |
| A59 | Cl | H | —OC$_2$H$_5$ | powder<br>MS (ESI): 559 [M + H]$^+$ |
| A60 | CF$_3$ | H | —NH$_2$ | powder<br>MS (ESI): 564 [M + H]$^+$ |

(No. 2)

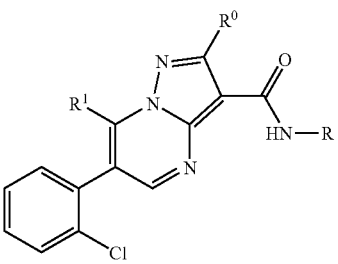

Z: benzyloxycarbonyl group, Boc: tert-butoxycarbonyl group

| Ex. Nos. | R$^1$ | R$^0$ | R | Physicochemical properties etc. |
|---|---|---|---|---|
| A61 | F$_3$C—pyridyl | CH$_3$ | H$_3$C-tetrahydrothiophene-SO$_2$ | powder<br>MS (ESI): 564 [M + H]$^+$ |
| A62 | Cl-phenyl | CH$_3$ | NC-cyclohexyl-CH$_3$ | powder<br>MS (APCI): 504/506 [M + H]$^+$ |
| A63 | Cl-phenyl | CH$_3$ | NC-cyclohexyl(CH$_3$)-NHZ | powder<br>MS (APCI): 653/655 [M + H]$^+$ |

TABLE 7-continued

| | | | | |
|---|---|---|---|---|
| A64 | 4-CF$_3$-C$_6$H$_4$- | H | H$_2$N-C(=O)-[4-methyl-1-BOC-piperidin-4-yl] | powder<br>MS (APCI):<br>643/645<br>[M + H]$^+$ |

Examples A65

(1) To a solution of 1-(tert-butoxycarbonylamino)-cyclopentanecarboxylic acid (2.29 g) in methanol (10 mL) was added dropwise 2M trimethylsilyldiazomethane solution in hexane (11.9 mL) under ice-cooling. The reaction mixture was concentrated, and to the residue was added hexane. The precipitated crystals were collected by filtration, and the filtrate was purified by column chromatography on silica gel (solvent; hexane/ethyl acetate=9/1 to 7/3). The product and the crystals obtained above were combined to give methyl 1-(tert-butoxycarbonylamino)-cyclopentane-carboxylate (2.49 g).

MS (ESI) m/z; 244 [M+H]$^+$ (2) To a solution of the compound obtained in the above step (1) (2.49 g) in tetrahydrofuran (12 mL) was added dropwise 3M methyl magnesium bromide solution in diethylether (13.3 mL) under ice-cooling and under nitrogen atmosphere. The mixture was stirred at room temperature overnight. To the reaction mixture was added water, and the mixture was extracted with ethyl acetate. The organic layer was dried over magnesium sulfate and purified by column chromatography on silica gel (solvent; hexane/ethyl acetate=8/1) to give a mixture of tert-butyl[1-(1-hydroxy-1-methyl-ethyl)cyclopentyl]carbamate and methyl 1-(tert-butoxycarbonylamino) cyclopentane-carboxylate (0.57 g) as a powder.

(3) To a solution of the compound obtained in the above step (2) (0.56 g) in chloroform (5 mL) was added trifluoroacetic acid (2 mL), and the mixture was stirred at room temperature for 10 minutes. The reaction mixture was concentrated in vacuo and, the residue was dissolved in methanol (1.0 mL). Thereto was added concentrated hydrochloric acid (0.6 mL), and the mixture was stirred for 1 minute. The reaction mixture was concentrated in vacuo, and the residue was dissolved in ethanol. The solution was concentrated, and to the residue was added ethanol/diethylether. The mixture was stirred overnight and the precipitated crystals were collected by filtration, washed with diethylether and dried to give a mixture of 1-(1-hydroxy-1-methylethyl)-cyclopentylamine hydrochloride and methyl 1-aminocyclopentanecarboxylate hydrochloride (376 mg) as a powder.

(4) The compound obtained in the above step (3) (56 mg) and 3-carboxy-6-(2-chlorophenyl)-7-(4-chlorophenyl)-pyrazolo[1,5-a]pyrimidine (100 mg) were treated in the same manner as described in Example A4-(1) and the reaction product was dissolved in ethanol (2 mL). Thereto was added an aqueous 2 N sodium hydroxide solution (0.2 mL) and the mixture was stirred at 60° C. for 2.5 hours. After cooling to room temperature, the reaction mixture was neutralized with an aqueous 2 N hydrochloric acid and extracted with dichloromethane. The organic layer was concentrated in vacuo and the resultant crude product was purified by column chromatography on silica gel (solvent; hexane/ethyl acetate=70/30 to 50/50 chloroform/methanol=90/10) to give 6-(2-chlorophenyl)-7-(4-chlorophenyl)-3-[N-[1-(1-hydroxy-1-methylethyl) cyclopentyl]carbamoyl]pyrazolo[1,5-a]pyrimidine (65 mg, yield: 49%; compound a) as a powder and 3-[N-(1-carboxycyclopentyl)-carbamoyl]-6-(2-chlorophenyl)-7-(4-chlorophenyl)pyrazolo[1,5-a]pyrimidine (24 mg, yield: 19%, compound b) as a powder.

Compound a: MS (APCI) m/z; 509/511 [M+H]$^+$

Compound b: MS (APCI) m/z; 495/497 [M+H]$^+$

Examples A66 to A72

The corresponding starting materials were treated in the same manner as described in Example A4-(1) to give compounds as shown in the following Table 8.

TABLE 8

| Ex. Nos. | R' | R$^0$ | R | Physicochemical properties etc. |
|---|---|---|---|---|
| A66 | CF$_3$ | H | H$_3$CO-C(=O)-[3-methyl-tetrahydrothiophen-3-yl] | powder<br>MS (APCI):<br>561/563 [M + H]$^+$ |
| A67 | CF$_3$ | H | H$_3$CO-C(=O)-[3-methyl-thietan-3-yl] | powder<br>MS (APCI):<br>547/549 [M + H]$^+$ |
| A68 | CF$_3$ | H | H$_3$CO-C(=O)-[4-methyl-1-CH$_3$-piperidin-4-yl] | powder<br>MS (APCI):<br>572/574 [M + H]$^+$ |
| A69 | Cl | CH$_3$ | HO-[cyclopentyl] | powder<br>MS (APCI):<br>495/497 [M + H]$^+$ |
| A70 | Cl | CH$_3$ | (H$_3$C)$_2$C(OH)- | powder<br>MS (APCI):<br>469/471 [M + H]$^+$ |
| A71 | CF$_3$ | H | HO-[4-methyl-tetrahydrothiopyran-4-yl] | powder<br>MS (APCI):<br>547/549 [M + H]$^+$ |

TABLE 8-continued

[Structure: pyrazolo-pyrimidine core with R' on upper phenyl, R⁰ substituent, 2-chlorophenyl, and HN—R carboxamide]

| Ex. Nos. | R' | R⁰ | R | Physicochemical properties etc. |
|---|---|---|---|---|
| A72 | Cl | CH₃ | [cyclopentane-spiro-CH₂-NHBoc] | powder MS (APCI): 594/596 [M + H]⁺ |

Examples A73 to A74

The corresponding starting materials were treated in the same manner as described in Example A41-(2) to give compounds as shown in the following Table 9.

TABLE 9

[Structure: 4-(trifluoromethyl)phenyl-pyrazolopyrimidine with 2-chlorophenyl and HN—R carboxamide]

| Ex. Nos. | R | Physicochemical properties etc. |
|---|---|---|
| A73 | H₃CO-C(=O)-[3-methyl-tetrahydrothiophene-3-yl-1,1-dioxide] | powder MS (APCI): 593/595 [M + H]⁺ |
| A74 | H₃CO-C(=O)-[3-methyl-thietane-3-yl-1,1-dioxide] | powder MS (APCI): 579/581 [M + H]⁺ |

Examples A73 to A78

The corresponding starting materials were treated in the same manner as described in Example A4-(2) to give compounds as shown in the following Table 10.

TABLE 10

[Structure: 4-(trifluoromethyl)phenyl-pyrazolopyrimidine with 2-chlorophenyl and HN—R carboxamide]

| Ex. Nos. | R | Physicochemical properties etc. |
|---|---|---|
| A75 | HO-C(=O)-[4-methyl-tetrahydropyran-4-yl sulfone (SO₂)] | powder MS (APCI): 593/595 [M + H]⁺ |
| A76 | HO-C(=O)-[3-methyl-thietane-3-yl-1,1-dioxide] | powder MS (APCI): 565/567 [M + H]⁺ |
| A77 | HO-C(=O)-[4-methyl-1-methylpiperidin-4-yl] | hydrochloride powder MS (APCI): 558/560 [M + H]⁺ |
| A78 | HO-C(=O)-[3-methyl-tetrahydrothiophene-3-yl-1,1-dioxide] | powder MS (ESI): 577/579 [M − H]⁻ |

Examples A79 to A106

The corresponding starting materials were treated in the same manner as described in Example A4-(1) to (2) to give compounds as shown in the following Table 11.

TABLE 11

(No. 1)

[Structure: pyrazolo-pyrimidine core with R' on upper phenyl, R⁰ substituent, 2-chlorophenyl, and HN—R carboxamide]

| Ex. Nos. | R' | R⁰ | R | Physicochemical properties etc. |
|---|---|---|---|---|
| A79 | Cl | H | [trans-4-methylcyclohexane-1-carboxylic acid] | powder MS (APCI): 509/511 [M + H]⁺ |

TABLE 11-continued

| Ex. Nos. | R' | R⁰ | R | Physicochemical properties etc. |
|---|---|---|---|---|
| A80 | CF₃ | H | 1-methylcyclohexane-1-carboxylic acid | powder MS (APCI): 543/545 [M + H]⁺ |
| A81 | Cl | CH₃ | (S)-2-methyl-3-phenylpropanoic acid | powder MS (APCI): 545/547 [M + H]⁺ |
| A82 | Cl | CH₃ | 1-methylcyclohexane-1-carboxylic acid | powder MS (APCI): 523/525 [M + H]⁺ |
| A83 | Cl | H | 2,2-dimethylpropanoic acid | powder MS (APCI): 469/471 [M + H]⁺ |
| A84 | Cl | CH₃ | trans-4-methylcyclohexane-1-carboxylic acid | powder MS (APCI): 523/525 [M + H]⁺ |

(No. 2)

[Structure: pyrazolo[1,5-a]pyrimidine core with R' on 4-phenyl, R⁰ at 2-position, C(O)NH-R at 3-position, 2-chlorophenyl at 6-position]

| Ex. Nos. | R' | R⁰ | R | Physicochemical properties etc. |
|---|---|---|---|---|
| A85 | Cl | H | (S)-2-cyclohexylpropanoic acid | powder MS (APCI): 523/525 [M + H]⁺ |
| A86 | Cl | H | 2-ethyl-2-phenylpropanoic acid | powder MS (APCI): 545/547 [M + H]⁺ |
| A87 | CF₃ | H | 2-ethyl-2-phenylpropanoic acid | powder MS (APCI): 579/581 [M + H]⁺ |
| A88 | Cl | C₂H₅ | 1-methylcyclohexane-1-carboxylic acid | powder MS (APCI): 537/539 [M + H]⁺ |
| A89 | Cl | CH₃ | 2-(4-fluorophenyl)propanoic acid | powder MS (APCI): 549/551 [M + H]⁺ |
| A90 | Cl | CH₃ | 2-(4-methoxyphenyl)propanoic acid | powder MS (APCI): 561/563 [M + H]⁺ |

(No. 3)

[Structure: pyrazolo[1,5-a]pyrimidine core with R' on 4-phenyl, R⁰ at 2-position, C(O)NH-R at 3-position, 2-chlorophenyl at 6-position]

| Ex. Nos. | R' | R⁰ | R | Physicochemical properties etc. |
|---|---|---|---|---|
| A91 | Cl | CH₃ | 2-(4-chlorophenyl)propanoic acid | powder MS (APCI): 565/567 [M + H]⁺ |
| A92 | Cl | CH₃ | 2-(2-chlorophenyl)propanoic acid | powder MS (APCI): 565/567 [M + H]⁺ |
| A93 | Cl | CH₃ | 2-(3-chlorophenyl)propanoic acid | powder MS (APCI): 565/567 [M + H]⁺ |
| A94 | Cl | CH₃ | 2-(4-trifluoromethylphenyl)propanoic acid | powder MS (APCI): 599/601 [M + H]⁺ |
| A95 | Cl | CH₃ | 1-methyl-2,3-dihydro-1H-indene-1-carboxylic acid | powder MS (APCI): 557/559 [M + H]⁺ |
| A96 | Cl | H | (S)-2-phenylpropanoic acid | powder MS (APCI): 517/519 [M + H]⁺ |

TABLE 11-continued

| Ex. No. | R' | R⁰ | R | Physicochemical properties etc. |
|---|---|---|---|---|
| A97 | Cl | CH₃ | 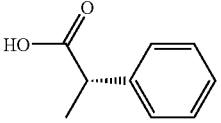 | powder MS (APCI): 531/533 [M + H]⁺ |
| A98 | CF₃ | CH₃ | 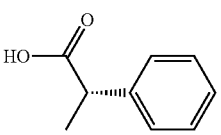 | powder MS (APCI): 565/567 [M + H]⁺ |

(No. 4)

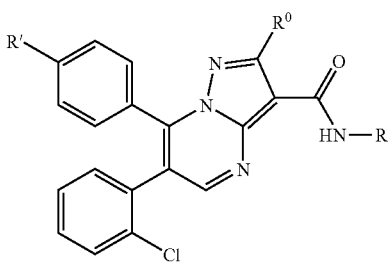

| Ex. Nos. | R' | R⁰ | R | Physicochemical properties etc. |
|---|---|---|---|---|
| A99 | Cl | H₃CO— | 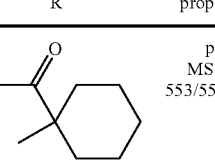 | powder MS (APCI): 553/555 [M + H]⁺ |
| A100 | Cl | CH₃ | 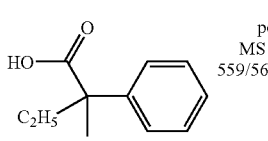 | powder MS (APCI): 559/561 [M + H]⁺ |
| A101 | CF₃ | H | 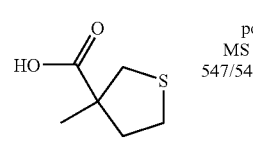 | powder MS (APCI): 547/549 [M + H]⁺ |
| A102 | Cl | CH₃ | 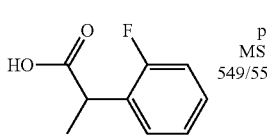 | powder MS (APCI): 549/551 [M + H]⁺ |
| A103 | Cl | CH₃ | 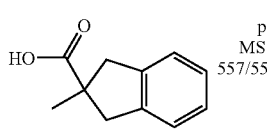 | powder MS (APCI): 557/559 [M + H]⁺ |
| A104 | Cl | H | 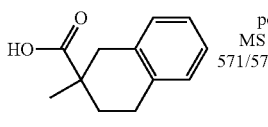 | powder MS (APCI): 571/573 [M + H]⁺ |
| A105 | CF₃ | CH₃ | 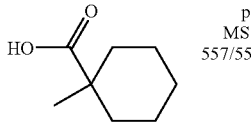 | powder MS (APCI): 557/559 [M + H]⁺ |
| A106 | Cl | CH₃ | 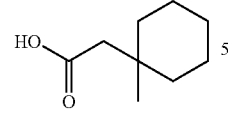 | powder MS (APCI): 537/539 [M + H]⁺ |

Example A107

(1) To a solution of the compound obtained in Example A64 (805 mg) in dioxane (10 mL) was added a solution of 4N hydrochloric acid in dioxane (10 mL) and the mixture was stirred at room temperature for 4 hours. The reaction mixture was diluted with diisopropylether and the precipitates were collected by filtration to give 4-carbamoyl-4-[6-(2-chlorophenyl)-7-(4-trifluoromethylphenyl)pyrazolo[1,5-a]pyrimidine-3-carboxamido]piperidine hydrochloride (784 mg, yield: 100%) as a powder.

MS (APCI) m/z; 543/545 [M+H]⁺

(2) To a solution of the compound obtained in the above step (1) (50 mg) in dimethylformamide (1 mL) were added potassium carbonate (30 mg) and isopropyl iodide (13 μL) and the mixture was stirred at 40° C. for 20 hours. After cooling to room temperature, to the reaction mixture was added water and the mixture was extracted with ethyl acetate. The organic layer was concentrated in vacuo and the resultant crude product was purified by column chromatography on silica gel (solvent; chloroform/methanol=99/1 to 87/13) to give 4-carbamoyl-4-[6-(2-chlorophenyl)-7-(4-trifluoromethylphenyl)pyrazolo[1,5-a]pyrimidine-3-carboxamido]-1-isopropylpiperidine (27 mg, yield: 55%) as a powder.

MS (APCI) m/z; 585/587 [M+H]⁺

Example A108

To a solution of the compound obtained in Example A107-(1) (45 mg) in methylene chloride (2 mL) were added triethylamine (32.5 μL) and methanesulfonyl chloride (7.8 μL) and the mixture was stirred at room temperature for 15 hours. To the reaction mixture was added water and the mixture was extracted with chloroform. The organic layer was concentrated in vacuo and the resultant crude product was purified by column chromatography on silica gel (solvent; hexane/ethyl acetate=30/70 to 0/100) to give 4-carbamoyl-4-[6-(2-chlorophenyl)-7-(4-trifluoromethylphenyl)pyrazolo[1,5-a]pyrimidine-3-carboxamido]-1-methylsulfonylpiperidine (36 mg, yield: 75%) as a powder.

MS (APCI) m/z; 621/623 [M+H]⁺

Examples A109 to A121

The corresponding starting materials were treated in the same manner as described in Example A5 to give compounds as shown in the following Table 12.

TABLE 12

(No. 1)

Structure: pyrazolo[1,5-a]pyrimidine core with R'/R'' substituted phenyl at one position, 2-chlorophenyl at another, R⁰ substituent, and HN—R carboxamide.

Me: methyl group, Et: ethyl group

| Ex. Nos. | R' | R'' | R⁰ | R | Physicochemical properties etc. |
|---|---|---|---|---|---|
| A109 | CF₃ | H | H | 4-methyl-tetrahydropyran-4-yl-carboxamide (H₂N-C(=O)-) | powder MS (APCI): 544/546 [M + H]⁺ |
| A110 | Cl | F | H | 4-methyl-1,1-dioxothian-4-yl-carboxamide | powder MS (APCI): 576/578 [M + H]⁺ |
| A111 | Cl | H | Et | 1-methylcyclohexyl-carboxamide | powder MS (APCI): 536/538 [M + H]⁺ |
| A112 | CF₃ | H | H | 3-methyl-1,1-dioxothiolan-3-yl-(dimethyl)carboxamide (Me₂N-) | powder MS (ESI): 606 [M + H]⁺ |
| A113 | CF₃ | H | H | 4-methyl-tetrahydropyran-4-yl-(dimethyl)carboxamide (Me₂N-) | powder MS (ESI): 572 [M + H]⁺ |
| A114 | CF₃ | H | H | 3-methyl-1,1-dioxothiolan-3-yl-(methyl)carboxamide (MeHN-) | powder MS (ESI): 592 [M + H]⁺ |
| A115 | CF₃ | H | H | 4-methyl-tetrahydropyran-4-yl-(methyl)carboxamide (MeHN-) | powder MS (ESI): 558 [M + H]⁺ |
| A116 | CF₃ | H | H | 3-methyl-1,1-dioxothiolan-3-yl-carboxamide | powder MS (ESI): 578 [M + H]⁺ |

(No. 2)

Structure: pyrazolo[1,5-a]pyrimidine core with R' substituted phenyl, 2-chlorophenyl, R⁰, and HN—R carboxamide.

Me: methyl group

| Ex. Nos. | R' | R⁰ | R | Physicochemical properties etc. |
|---|---|---|---|---|
| A117 | CF₃ | H | 3-methyl-3-(sulfonyl)oxetane carboxamide | powder MS (ESI): 564 [M + H]+ |
| A118 | Cl | CH₃ | 1-methyl-indanyl carboxamide | powder MS (ESI): 556 [M + H]+ |
| A119 | Cl | CH₃ | 2-methyl-indan-2-yl carboxamide | powder MS (ESI): 556 [M + H]+ |
| A120 | Cl | CH₃ | 2-methyl-1,2,3,4-tetrahydronaphthalen-2-yl carboxamide | powder MS (ESI): 570 [M + H]+ |
| A121 | CF₃ | H | 4-methyl-1-methylpiperidin-4-yl carboxamide | powder MS (ESI): 557 [M + H]+ |

Examples A122 to A123

The corresponding starting materials were treated in the same manner as described in Example A108 to give compounds as shown in the following Table 13.

TABLE 13

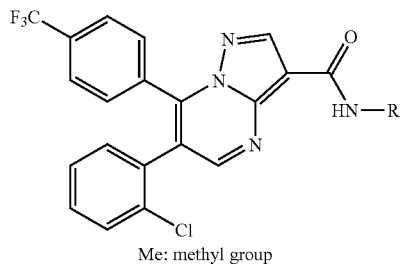

Me: methyl group

| Ex. Nos. | R | Physicochemical properties etc. |
|---|---|---|
| A122 | (4-carbamoyl-4-methylpiperidin-1-yl with N-acetyl) | powder<br>MS (APCI): 585/587 [M + H]⁺ |
| A123 | (4-carbamoyl-4-methylpiperidin-1-yl with N-SO₂NMe₂) | powder<br>MS (APCI): 650/652 [M + H]⁺ |

Examples A124 to A138

The corresponding starting materials were treated in the same manner as described in Example A5 to give compounds as shown in the following Table 14.

TABLE 14
(No. 1)

(pyrazolopyrimidine core with 4-chlorophenyl, 2-chlorophenyl, and C(O)NH—R substituents)

Me: methyl group

| Ex. Nos. | R | Physicochemical properties etc. |
|---|---|---|
| A124 | CH(CH₃)-cyclohexyl-C(O)NMe₂ | powder<br>MS (ESI): 550 [M + H]⁺ |
| A125 | CH(CH₃)-phenyl-C(O)NMe₂ | powder<br>MS (ESI): 544 [M + H]⁺ |
| A126 | CH(CH₃)-phenyl-C(O)NMe₂ | powder<br>MS (ESI): 544 [M + H]⁺ |
| A127 | CH(CH₃)-cyclohexyl-C(O)NHMe | powder<br>MS (ESI): 536 [M + H]+ |
| A128 | CH(CH₃)-phenyl-C(O)NHMe | powder<br>MS (ESI): 530 [M + H]+ |
| A129 | CH(CH₃)-phenyl-C(O)NHMe | powder<br>MS (ESI): 530 [M + H]+ |
| A130 | CH(CH₃)-cyclohexyl-C(O)NH₂ | powder<br>MS (ESI): 522 [M + H]+ |

TABLE 14-continued

| Ex. Nos. | R | Physicochemical properties etc. |
|---|---|---|
| A131 | (2-phenylpropanamide group) | powder MS (APCI): 516/518 [M + H]+ |

(No. 2)

[Structure: 7-(4-chlorophenyl)-6-(2-chlorophenyl)-2-methyl-pyrazolo[1,5-a]pyrimidine-3-carboxamide core with HN—R]

| Ex. Nos. | R | Physicochemical properties etc. |
|---|---|---|
| A132 | H₂N-C(O)-CH(CH₃)-(4-F-phenyl) | powder MS (ESI): 548 [M + H]⁺ |
| A133 | H₂N-C(O)-CH(CH₃)-(4-OCH₃-phenyl) | powder MS (ESI): 560 [M + H]⁺ |
| A134 | H₂N-C(O)-CH(CH₃)-(4-Cl-phenyl) | powder MS (ESI): 564 [M + H]⁺ |
| A135 | H₂N-C(O)-CH(CH₃)-(2-Cl-phenyl) | powder MS (ESI): 564 [M + H]⁺ |
| A136 | H₂N-C(O)-CH(CH₃)-(3-Cl-phenyl) | powder MS (ESI): 564 [M + H]⁺ |
| A137 | H₂N-C(O)-CH(CH₃)-(4-CF₃-phenyl) | powder MS (ESI): 598 [M + H]+ |
| A138 | H₂N-C(O)-CH(CH₃)-(2-F-phenyl) | powder MS (ESI): 548 [M + H]+ |

Examples A139 to A142

The corresponding starting materials were treated in the same manner as described in Example A1 to give compounds as shown in the following Table 15.

TABLE 15

[Structure: pyrazolo[1,5-a]pyrimidine with R' on 4-phenyl, 2-chlorophenyl, R⁰ at 2-position, and C(O)HN—R at 3-position]

| Ex. Nos. | R' | R⁰ | R | Physicochemical properties etc. |
|---|---|---|---|---|
| A139 | Cl | —NHSO₂CH₃ | H₃C-(1-methyl-sulfolan-3-yl) SO₂ | powder MS (ESI): 608 [M + H]⁺ |
| A140 | Cl | —O(CH₂)₂OH | H₃C-(1-methyl-sulfolan-3-yl) SO₂ | powder MS (ESI): 575 [M + H]⁺ |
| A141 | CF₃ | —O(CH₂)₂OH | H₃C-(1-methyl-sulfolan-3-yl) SO₂ | powder MS (ESI): 609 [M + H]⁺ |
| A142 | Cl | —O(CH₂)₂OH | H₃CO-C(O)-(1-methylcyclohexyl) | powder MS (APCI): 583/585 [M + H]⁺ |

Examples A143

The compound obtained in Example A142 (175 mg) was treated in the same manner as described in Example A4-(2) to give 3-[N-(1-carboxycyclohexyl)carbamoyl]-6-(2-chlorophenyl)-7-(4-chlorophenyl)-2-(2-hydroxyethoxy)-pyrazolo[1,5-a]pyrimidine (131 mg, yield: 77%) as a powder.
MS (APCI) m/z; 569/571 [M+H]⁺

Example A144

The compound obtained in Reference Example A18 (6-(2-bromophenyl)-3-carboxy-7-(4-chlorophenyl)pyrazolo[1,5-a]pyrimidine; 500 mg) and the compound obtained in Reference Example A9 (293 mg) were treated in the same manner as described in Example A1 and then the reaction product was treated in the same manner as described in Example A4-(2) to give 6-(2-bromophenyl)-3-[N-(1-carboxy-cyclohexyl)carbamoyl]-7-(4-chlorophenyl)pyrazolo[1,5-a]pyrimidine (648 mg) as a powder.
MS (APCI) m/z; 553/555 [M+H]⁺

Example A145

(1) The compound obtained in Example A144 (100 mg) and ammonium chloride (19 mg) were treated in the same manner as described in Example A5 to give 6-(2-bromophenyl)-3-[N-(1-carbamoylcyclohexyl)carbamoyl]-7-(4-chlorophenyl)-pyrazolo[1,5-a]pyrimidine (84 mg) as a powder.

MS (APCI) m/z; 552/554 [M+H]⁺

(2) A solution of the compound obtained in the above step (1) (83 mg), zinc cyanide (20 mg) and tetrakis(triphenylphosphine)palladium (17 mg) in dimethylformamide (1 mL) was stirred under nitrogen atmosphere at 110° C. for 13 hours. After cooling to room temperature, to the reaction mixture was added water, and the mixture was extracted with ethyl acetate. The organic layer was concentrated in vacuo, and the resultant crude product was purified by column chromatography on silica gel (solvent; hexane/ethyl acetate=67/33 to 10/90) to give 3-[N-(1-carbamoylcyclohexyl)carbamoyl]-7-(4-chlorophenyl)-6-(2-cyanophenyl)pyrazolo[1,5-a]pyrimidine (22 mg, yield: 30%) as a powder.

MS (APCI) m/z; 499/501 [M+H]⁺

Examples A146 to A147

The corresponding starting materials were treated in the same manner as described in Example A1 and then the reaction product was treated in the same manner as described in Example A145 to give compounds as shown in the following Table 16.

TABLE 16

| Ex. Nos. | R⁰ | Physicochemical properties etc. |
|---|---|---|
| A146 | H | powder MS (APCI): 583 [M + H]+ |
| A147 | CH₃ | powder MS (APCI): 597 [M + H]+ |

Examples A148 to A149

The corresponding starting materials were treated in the same manner as described in Example A6 to give compounds as shown in the following Table 17.

TABLE 17

| Ex. Nos. | R | Physicochemical properties etc. |
|---|---|---|
| A148 | H₂NOC-cyclohexyl | powder MS (APCI): 599/601 [M + H]⁺ |
| A149 | H₂NOC-(SO₂-cyclohexyl) | powder MS (APCI): 649/651 [M + H]⁺ |

Examples A150

To a solution of the compound obtained in Example A1 (106 mg) in toluene (4 mL) and dimethylformamide (1.5 mL) were added sodium azide (86 mg) and triethylamine hydrochloride (183 mg), and the mixture was stirred at 120° C. for 24 hours. To the reaction mixture were further added sodium azide (90 mg) and triethylamine hydrochloride (183 mg), and the mixture was stirred for 21 hours. After cooling to room temperature, the reaction mixture was filtered through Celite to remove precipitates, and the filtrate was concentrated in vacuo. The resultant crude product was purified successively by column chromatography on silica gel (solvent; chloroform/methanol=100/0 to 95/5) and gel-permeation chromatography (solvent; chloroform) to give 6-(2-chlorophenyl)-7-(4-chlorophenyl)-3-[N-[1-(1,2,3,4-tetrazol-5-yl)cyclohexyl]carbamoyl]-pyrazolo[1,5-a]pyrimidine (95 mg, yield: 83%) as a powder.

MS (APCI) m/z; 533/535 [M+H]⁺

Example A151

To a solution of the compound obtained in Example A70 (195 mg) in methylene chloride (3 mL) was added m-chloroperbenzoic acid (75%, 180 mg), and the mixture was stirred at room temperature for 1 hour. To the reaction mixture were added an aqueous sodium thiosulfate solution and methylene chloride. The organic layer was separated and concentrated in vacuo. The resultant crude product was purified by column chromatography on NH-silica gel (Chromatorex NH silica gel, solvent; hexane/ethyl acetate=50/50 to 30/70) to give 6-(2-chlorophenyl)-7-(4-trifluoromethylphenyl)-3-[N-(4-hydroxymethyl-1,1-dioxotetrahydrothiopyran-4-yl)-carbamoyl]pyrazolo[1,5-a]pyrimidine (169 mg, yield: 82%) as a pale yellow powder.

MS (APCI) m/z; 579/581 [M+H]⁺

Example A152

To a solution of the compound obtained in Example A62 (50 mg) in tetrahydrofuran-methanol (1 mL/1 mL) was added Raney nickel, and the mixture was stirred under hydrogen atmosphere at 50° C. for 1.5 hour and at room temperature for 3 days. The reaction mixture was filtered, and the filtrate was concentrated in vacuo. The resultant crude product was purified by column chromatography on NH-silica gel (Chromatorex NH silica gel, solvent; chloroform) to give 3-[N-[1-(aminomethyl)-cyclohexyl]carbamoyl]-6-(2-chlorophenyl)-7-(4-chlorophenyl)-2-methylpyrazolo[1,5-a]pyrimidine (35 mg, yield: 69%) as a pale yellow powder.

MS (APCI) m/z; 508/510 [M+H]⁺

Example A153

To a solution of the compound obtained in Example A71 (35 mg) in methylene chloride (0.6 mL) was added trifluoroacetic acid (69 μL), and the mixture was stirred at room temperature overnight. To the reaction mixture was added an aqueous saturated sodium hydrogencarbonate solution, and the mixture was stirred for 5 minutes. The mixture was extracted with methylene chloride, and the organic layer was concentrated in vacuo. The resultant crude product was purified by column chromatography on NH-silica gel (Chromatorex NH silica gel, solvent; hexane/ethyl acetate=60/40 to 30/70) to give 3-[N-[(1-aminocyclopentyl)methyl]carbamoyl]-6-(2-chlorophenyl)-7-(4-chlorophenyl)-2-methylpyrazolo[1,5-a]pyrimidine (14 mg, yield: 48%) as a powder.

MS (APCI) m/z; 494/496 [M+H]+

Example A154

To a solution of the compound obtained in Example A152 (51 mg) and triethylamine (28 μL) in methylene chloride (4 mL) was added dropwise acetyl chloride (9 μL) at room temperature, and the mixture was stirred for 1 hour. To the reaction mixture were added water and methylene chloride, and the organic layer was separated and concentrated in vacuo. The resultant crude product was purified by column chromatography on silica gel (solvent; chloroform/methanol=100/0 to 95/5) to give 3-[N-[1-(acetylaminomethyl)cyclohexyl]carbamoyl]-6-(2-chlorophenyl)-7-(4-chlorophenyl)-2-methylpyrazolo[1,5-a]pyrimidine (36.5 mg, yield: 66%) as a powder.

MS (APCI) m/z; 550/552 [M+H]+

Example A155

The compound obtained in Example A152 (51 mg) and dimethylcarbamoyl chloride (11 μL) were treated in the same manner as described in Example A154 to give 6-(2-chlorophenyl)-7-(4-chlorophenyl)-2-methyl-3-[N-[1-[(3,3-dimethylureido)methyl]cyclohexyl]carbamoyl]pyrazolo[1,5-a]pyrimidine (25.3 mg, yield: 44%) as a powder.

MS (APCI) m/z; 579/581 [M+H]+

Example A156

The compound obtained in Example A152 (51 mg) and methanesulfonyl chloride (9 μL) were treated in the same manner as described in Example A154 to give 6-(2-chlorophenyl)-7-(4-chlorophenyl)-3-[N-[1-(mesylaminomethyl)cyclohexyl]carbamoyl]-2-methylpyrazolo[1,5-a]pyrimidine (39.2 mg, yield: 67%) as a powder.

MS (APCI) m/z; 586/588 [M+H]+

Example A157

The compound obtained in Example A152 (51 mg) and dimethylsulfamoyl chloride (13 μL) were treated in the same manner as described in Example A154 to give 6-(2-chlorophenyl)-7-(4-chlorophenyl)-2-methyl-3-[N-[1-[[(dimethylsulfamoyl)amino]methyl]cyclohexyl]carbamoyl]pyrazolo[1,5-a]pyrimidine (12.3 mg, yield: 20%) as a powder.

MS (APCI) m/z; 615/617 [M+H]+

Examples A158 to A159

The corresponding starting materials were treated in the same manner as described in Example A1 to give compounds as shown in the following Table 18.

TABLE 18

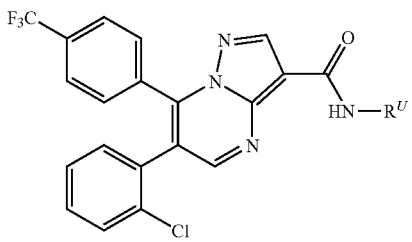

| Ex. Nos. | $R^U$ | Physicochemical properties etc. |
|---|---|---|
| A158 | (trans-4-hydroxy-3-methyl-tetrahydrothiophene-1,1-dioxide) | powder<br>MS (APCI): 551/553 [M + H]+ |
| A159 | (cis-4-hydroxy-3-methyl-tetrahydrothiophene-1,1-dioxide) | powder<br>MS (APCI): 551/553 [M + H]+ |

Examples A160 to A161

The corresponding starting materials were treated in the same manner as described in Example A1 to give compounds as shown in the following Table 19.

TABLE 19

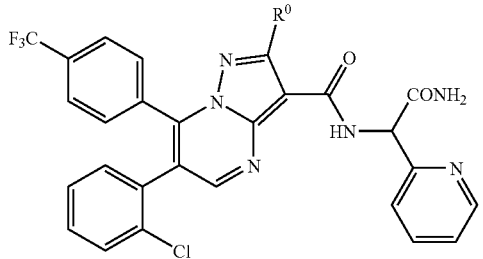

| Ex. Nos. | $R^0$ | Physicochemical properties etc. |
|---|---|---|
| A160 | H | powder<br>MS (APCI): 551/553 [M + H]+ |
| A161 | CH$_3$ | powder<br>MS (APCI): 565/567 [M + H]+ |

Examples A162 to A163

The compound obtained in Example A143 and the corresponding amine compound were treated in the same manner as described in Example A5 to give compounds as shown in the following Table 20.

TABLE 20

| Ex. Nos. | R^U | Physicochemical properties etc. |
|---|---|---|
| A162 | —NH₂ | powder<br>MS (APCI): 568/570 [M + H]⁺ |
| A163 | —NHCH₃ | powder<br>MS (APCI): 582/584 [M + H]⁺ |

Examples A164 to A174

The compound obtained in Example A75 and the corresponding amine compound were treated in the same manner as described in Example A5 to give compounds as shown in the following Table 21.

TABLE 21

| Ex. Nos. | R^t | Physicochemical properties etc. |
|---|---|---|
| A164 | ⟨CH₃⟩NH-CH₂CH₂-OH | powder<br>MS (ESI): 636 [M + H]⁺ |
| A165 | morpholino | powder<br>MS (ESI): 662 [M + H]⁺ |
| A166 | pyrrolidinyl | powder<br>MS (ESI): 646 [M + H]⁺ |
| A167 | —NHCH₃ | powder<br>MS (ESI): 606 [M + H]⁺ |
| A168 | —N(CH₃)₂ | powder<br>MS (ESI): 620 [M + H]⁺ |
| A169 | HN-cyclopropyl | powder<br>MS (ESI): 632 [M + H]⁺ |
| A170 | ⟨CH₃⟩NH-CH₂CH₂-OCH₃ | powder<br>MS (ESI): 650 [M + H]⁺ |

TABLE 21-continued

| Ex. Nos. | R^t | Physicochemical properties etc. |
|---|---|---|
| A171 | (CH₃)₂N-CH₂CH₂-OCH₃ | powder<br>MS (ESI): 664 [M + H]⁺ |
| A172 | CH₃NH-CH₂-CF₃ | powder<br>MS (ESI): 674 [M + H]⁺ |
| A173 | —NHSO₂CH₃ | powder<br>MS (ESI): 670 [M + H]⁺ |
| A174 | CH₃NH-CH₂-CN | powder<br>MS (ESI): 631 [M + H]⁺ |

Examples A175 to A184

The corresponding starting materials were treated in the same manner as described in Example A1, the reaction product was treated in the same manner as described in Example A4-(2) and then the reaction product treated in the same manner as described in Example A5 to give compounds as shown in the following Table 22.

TABLE 22

| Ex. Nos. | R' | R^t | Physicochemical properties etc. |
|---|---|---|---|
| A175 | Cl | NH₂ | powder<br>MS (APCI): 572/574 [M + H]⁺ |
| A176 | Cl | NHCH₃ | powder<br>MS (APCI): 586/588 [M + H]⁺ |
| A177 | Cl | —N(CH₃)₂ | powder<br>MS (ESI): 600/602 [M + H]⁺ |
| A178 | CF₃ | NH₂ | powder<br>MS (APCI): 606/608 [M + H]⁺ |
| A179 | CF₃ | NHCH₃ | powder<br>MS (APCI): 620/622 [M + H]⁺ |
| A180 | CF₃ | —N(CH₃)₂ | powder<br>MS (ESI): 634/636 |

TABLE 22-continued

[Structure: pyrazolo[1,5-a]pyrimidine core with CH3, R' on one phenyl, 2-Cl phenyl, and amide with cyclohexyl bearing SO2 and C(O)R^t group]

| Ex. Nos. | R' | R^t | Physicochemical properties etc. |
|---|---|---|---|
| A181 | Cl | -NH-CH2-CF3 | powder<br>MS (APCI): 654/656<br>[M + H]+ |
| A182 | CF3 | -NH-CH2-CF3 | powder<br>MS (APCI): 688/690<br>[M + H]+ |
| A183 | Cl | -NH-CH2CH2-OCH3 | powder<br>MS (APCI): 630/632<br>[M + H]+ |
| A184 | CF3 | -NH-CH2CH2-OCH3 | powder<br>MS (APCI): 664/666<br>[M + H]+ |

Examples B1

To a solution of the compound obtained in Reference Example B3 (70 mg) in tetrahydrofuran (2 mL) was added a solution of 2 M methylamine in tetrahydrofuran (0.14 mL), and the mixture was stirred at room temperature for 10 minutes. The reaction mixture was concentrated in vacuo, and to the residue was added an aqueous saturated sodium hydrogencarbonate solution. The mixture was extracted with chloroform, and the organic layer was concentrated in vacuo. The resultant crude product was purified by column chromatography on NH-silica gel (Chromatorex NH silica gel, solvent; hexane/ethyl acetate=80/20 to 30/70) to give 6-(2-chlorophenyl)-7-(4-chlorophenyl)-3-ethoxycarbonyl-2-(N-methylsulfamoyl)pyrazolo[1,5-a]pyrimidine (75 mg, yield: 100%) as a colorless powder.

MS (APCI) m/z; 505/507 [M+H]+

Example B2

(1) To a solution of the compound obtained in Example B1 (524 mg) in ethanol/tetrahydrofuran (7 mL/7 mL) was added an aqueous 2N sodium hydroxide solution (1.04 mL), and the mixture was stirred at room temperature for 2 hours. The reaction mixture was weakly acidified with an aqueous 2N hydrochloric acid. The mixture was concentrated in vacuo and extracted with chloroform. The organic layer was dried over magnesium sulfate and filtered. The filtrate was concentrated in vacuo to give 3-carboxy-6-(2-chlorophenyl)-7-(4-chlorophenyl)-2-(N-methylsulfamoyl)-pyrazolo[1,5-a]pyrimidine (543 mg) as a crude product.

(2) The compound obtained in the above step (1) was treated in the same manner as described in Example A1 to give 6-(2-chlorophenyl)-7-(4-chlorophenyl)-2-(N-methylsulfamoyl)-3-[N-(1-pyrrolidinyl)carbamoyl]-pyrazolo[1,5-a]pyrimidine (29 mg) as a pale yellow powder.

MS (APCI) m/z; 545/547 [M+H]+

Example B3

The compound obtained in Reference Example B3 (600 mg) in tetrahydrofuran (12 mL) was added a solution of 2M dimethylamine in tetrahydrofuran (1.17 mL), and the mixture was stirred at room temperature for 30 minutes. The reaction mixture was concentrated in vacuo, and to the residue was added an aqueous saturated sodium hydrogencarbonate solution. The mixture was extracted with chloroform, and the organic layer was concentrated in vacuo. The resultant crude product was purified by column chromatography on NH-silica gel (Chromatorex NH silica gel, solvent; hexane/ethyl acetate=80/20 to 0/100) to give 6-(2-chlorophenyl)-7-(4-chlorophenyl)-3-ethoxycarbonyl-2-(N,N-dimethylsulfamoyl)pyrazolo[1,5-a]pyrimidine (566 mg, yield: 93%) as a colorless powder.

MS (APCI) m/z; 519/521 [M+H]+

Example B4

To a solution of the compound obtained in Reference Example B3 (300 mg) in tetrahydrofuran (10 mL) was added a solution of 0.5M ammonia in 1,4-dioxane (7 mL), and the mixture was stirred at room temperature overnight. The reaction mixture was concentrated in vacuo, and to the residue was added tetrahydrofuran and the mixture was filtered to remove precipitates. The filtrate was concentrated in vacuo, and the resultant crude product was purified by column chromatography on silica gel (solvent; hexane/ethyl acetate=80/20 to 50/50) to give 6-(2-chlorophenyl)-7-(4-chlorophenyl)-3-ethoxycarbonyl-2-sulfamoylpyrazolo[1,5-a]pyrimidine (242 mg, yield: 84%) as a colorless powder.

MS (APCI) m/z; 491/493 [M+H]+

Example B5

To a solution of the compound obtained in Reference Example B7 (40 mg) in chloroform (2 mL) was added ethyl isocyanate (1 mL), and the mixture was refluxed under heating overnight. After cooling to room temperature, to the reaction mixture were added an aqueous sodium hydrogencarbonate solution and chloroform. After stirring, the organic layer was separated and concentrated in vacuo. The resultant crude product was purified by column chromatography on silica gel (solvent; hexane/ethyl acetate=80/20 to 60/40) to give 6-(2-chlorophenyl)-7-(4-chlorophenyl)-3-(N-cyclopentylcarbamoyl)-2-(3-ethylureido)-pyrazolo[1,5-a]pyrimidine (33.3 mg, yield: 72%) as a pale yellow solid.

MS (APCI) m/z; 537/539 [M+H]+

Examples B6 to B24

The corresponding starting materials were treated in the same manner as described in Example B2-(2) to give compounds as shown in the following Table 23.

TABLES 23

(No. 1)

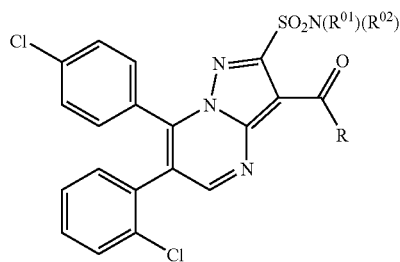

| Ex. Nos. | —N(R$^{01}$)(R$^{02}$) | R | Physicochemical properties etc. |
|---|---|---|---|
| B6 | —NHCH$_3$ | HN—[(3S)-tetrahydrothiophene-SO$_2$], N-methyl | powder MS (APCI): 594/596 [M + H]$^+$ |
| B7 | —NHCH$_3$ | HN—cyclopentyl, N-methyl | powder MS (APCI): 544/546 [M + H]$^+$ |
| B8 | —NHCH$_3$ | N-methyl-N-(pyridin-2-yl)-N'-methylhydrazino | powder MS (APCI): 582/584 [M + H]$^+$ |
| B9 | —N(CH$_3$)$_2$ | HN—[(3S)-tetrahydrothiophene-SO$_2$], N-methyl | powder MS (APCI): 608/610 [M + H]$^+$ |
| B10 | —N(CH$_3$)$_2$ | HN—cyclopentyl, N-methyl | powder MS (APCI): 558/560 [M + H]$^+$ |
| B11 | —N(CH$_3$)$_2$ | HN—N-pyrrolidinyl | powder MS (APCI): 559/561 [M + H]$^+$ |
| B12 | —N(CH$_3$)$_2$ | N-methyl-N-(pyridin-2-yl)-N'-methylhydrazino | powder MS (APCI): 596/598 [M + H]$^+$ |
| B13 | —NH$_2$ | HN—[(3S)-tetrahydrothiophene-SO$_2$], N-methyl | powder MS (APCI): 580/582 [M + H]$^+$ |
| B14 | —NH$_2$ | HN—N-pyrrolidinyl | powder MS (APCI): 531/533 [M + H]$^+$ |
| B15 | —NH$_2$ | N-methyl-N-(pyridin-2-yl)-N'-methylhydrazino | powder MS (APCI): 568/570 [M + H]$^+$ |

TABLES 23-continued (No. 2)

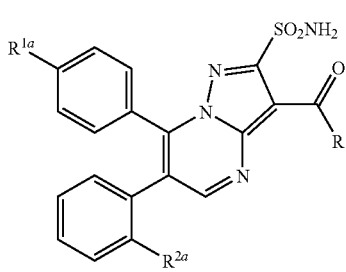

| Ex. Nos. | R$^{1a}$ | R$^{2a}$ | R | Physicochemical properties etc. |
|---|---|---|---|---|
| B16 | Cl | Cl | HN—[(3S)-tetrahydrothiophene-SO$_2$], N-methyl | powder MS (APCI): 580/582 [M + H]$^+$ |
| B17 | Cl | Cl | HN—cyclopentyl, N-methyl | powder MS (APCI): 530/532 [M + H]$^+$ |
| B18 | Cl | Cl | HN—tetrahydro-2H-thiopyran-1,1-dioxide-4-yl, N-methyl | powder MS (APCI): 594/596 [M + H]$^+$ |
| B19 | CF$_3$ | Cl | HN—[(3S)-tetrahydrothiophene-SO$_2$], N-methyl | powder MS (APCI): 614/616 [M + H]$^+$ |
| B20 | CF$_3$ | Cl | HN—[(3R)-tetrahydrothiophene-SO$_2$], N-methyl | powder MS (APCI): 614/616 [M + H]$^+$ |
| B21 | CF$_3$ | Cl | HN—cyclopentyl, N-methyl | powder MS (APCI): 564/566 [M + H]$^+$ |
| B22 | Cl | CN | HN—[(3S)-tetrahydrothiophene-SO$_2$], N-methyl | powder MS (APCI): 571/573 [M + H]$^+$ |
| B23 | Cl | CN | HN—cyclopentyl, N-methyl | powder MS (APCI): 521/523 [M + H]$^+$ |
| B24 | Cl | CN | N-methyl-N-(pyridin-2-yl)-N'-methylhydrazino | powder MS (APCI): 559/561 [M + H]$^+$ |

Examples B25 to B28

The corresponding starting materials were treated in the same manner as described in Example B2 to give compounds as shown in the following Table 24.

TABLE 24

| Ex. Nos. | R | Physicochemical properties etc. |
|---|---|---|
| B25 | HN—(tetrahydrothiophene-1,1-dioxide-3-yl) | powder MS (APCI): 637/639 [M + H]$^+$ |
| B26 | HN—cyclopentyl | powder MS (APCI): 587/589 [M + H]$^+$ |
| B27 | N-methyl-N'-methyl-N'-(2-pyridyl)hydrazino | powder MS (APCI): 625/627 [M + H]$^+$ |
| B28 | HN—N-pyrrolidinyl | powder MS (APCI) 588/590 [M + H]$^+$ |

Example B29

(1) The corresponding starting materials were treated in the same manner as described in Example B2-(2) to give 6-(2-chlorophenyl)-7-(4-chlorophenyl)-3-[N-(1-methoxycarbonylcyclohexyl)carbamoyl]-2-(N-methylsulfamoyl)-pyrazolo[1,5-a]pyrimidine (185 mg) as a pale yellow powder.

MS (APCI) m/z; 616/618 [M+H]$^+$ (2) The compound obtained in the above step (1) (182 mg) was treated in the same manner as described in Example A4-(2) to give 3-[N-(1-carboxycyclohexyl)-carbamoyl]-6-(2-chlorophenyl)-7-(4-chlorophenyl)-2-(N-methylsulfamoyl)-pyrazolo[1,5-a]pyrimidine (5.6 mg) as a powder.

MS (APCI) m/z; 602/604 [M+H]$^+$

Example B30

The compound obtained in Reference Example B5 (35 mg) and the compound obtained in Reference Example B10 (17.5 mg) were treated in the same manner as described in Example A1 to give 3-[N-(1-carbamoylcyclohexyl)carbamoyl]-6-(2-chlorophenyl)-7-(4-chlorophenyl)-2-sulfamoylpyrazolo[1,5-a]pyrimidine (3.6 mg, yield: 8%) as a colorless powder.

MS (APCI) m/z; 587/589 [M+H]$^+$

Example B31

(1) The compound obtained in Example A6-(1) (200 mg) and the compound obtained in Reference Example B11 (137 mg) were treated in the same manner as described in Example A1 to give 2-amino-3-[N-(4-carbamoyl-1,1-dioxo-tetrahydro-thiopyran-4-yl)carbamoyl]-6-(2-chlorophenyl)-7-(4-trifluoromethylphenyl)pyrazolo[1,5-a]pyrimidine (82 mg, yield: 29%) as a pale yellow powder.

MS (APCI) m/z; 607/609 [M+H]$^+$ (2) The compound obtained in the above step (1) (39 mg) was treated in the same manner as described in Example B5 to give 3-[N-(4-carbamoyl-1,1-dioxo-tetrahydrothiopyran-4-yl)carbamoyl]-6-(2-chlorophenyl)-2-(3-ethylureido)-7-(4-trifluoromethylphenyl)pyrazolo[1,5-a]pyrimidine (15 mg, yield: 34%) as a pale yellow powder.

MS (APCI) m/z; 678/680 [M+H]$^+$

Example B32

The compound obtained in Reference Example B17 (500 mg) was treated in the same manner as described in Example A1 and then the reaction product was treated in the same manner as described in Example A41-(2) to give 6-(2-chlorophenyl)-7-(4-trifluoromethylphenyl)-2-hydroxymethyl-3-[N-(4-methyl-1,1-dioxotetrahydrothiopyran-4-yl)-carbamoyl]pyrazolo[1,5-a]pyrimidine (498 mg) as a pale yellow powder.

MS (APCI) m/z; 593/595 [M+H]$^+$

Example B33

To a solution of the compound obtained in Example B32 (335 mg) in dimethylformamide (3.5 mL) was added pyridinium dichromate (1.28 g), and the mixture was stirred at room temperature for 16 hours. The reaction mixture was filtered through a silica gel-pad and washed with chloroform/methanol (9/1). The mother liquor was concentrated in vacuo. The residue was diluted with ethyl acetate, and thereto was added water. The organic layer was separated, washed successively with water and brine, dried over magnesium sulfate and filtered. The filtrate was concentrated in vacuo, and the resultant crude product was purified by column chromatography on silica gel (solvent; chloroform/methanol=100/0 to 85/15) to give 2-carboxy-6-(2-chlorophenyl)-7-(4-trifluoromethylphenyl)-3-[N-(4-methyl-1,1-dioxotetrahydrothiopyran-4-yl)carbamoyl]-pyrazolo[1,5-a]pyrimidine (245 mg, yield: 71%) as a colorless solid.

MS (APCI) m/z; 607/609 [M+H]$^+$

Example B34

The compound obtained in Reference Example B17 (45 mg) was treated in the same manner as described in Example A1 to give 3-[N-(1-carbamoylcyclohexyl)-carbamoyl]-6-(2-chlorophenyl)-7-(4-trifluoromethylphenyl)-2-(hydroxymethyl)pyrazolo[1,5-a]pyrimidine (29 mg, yield: 50%) as a colorless powder.

MS (APCI) m/z; 572/574 [M+H]$^+$

Examples B35 to B38

The compound obtained in Example B33 and the corresponding amine compound were treated in the same manner as described in Example A5 to give compounds as shown in the following Table 25.

TABLE 25

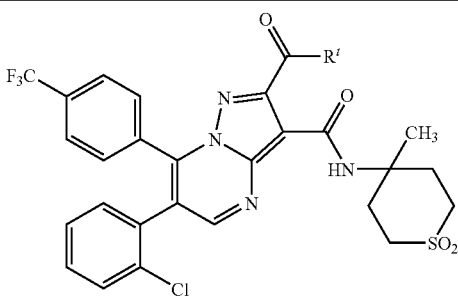

| Ex. Nos. | $R^t$ | Physicochemical properties etc. |
|---|---|---|
| B35 | NH₂ | powder MS (APCI): 606/608 [M + H]⁺ |
| B36 | —NHCH₃ | powder MS (APCI): 620/622 [M + H]⁺ |
| B37 | —N(CH₃)₂ | powder MS (APCI): 634/636 [M + H]⁺ |
| B38 | —NH—N(CH₃)₂ | powder MS (APCI): 649/651 [M + H]⁺ |

Examples B39 to B51

The corresponding starting materials were treated in the same manner as described in Example A1 to give compounds as shown in the following Table 26.

TABLE 26

(No. 1)

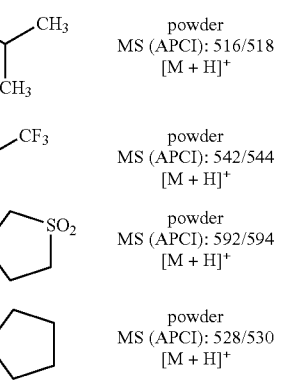

| Ex. Nos. | $R^t$ | $R^U$ | Physicochemical properties etc. |
|---|---|---|---|
| B39 | NH₂ | (tetrahydrothiophene-SO₂, methyl) | powder MS (APCI): 578/580 [M + H]⁺ |
| B40 | NH₂ | isopropyl-CH(CH₃)CH₂CH₃ | powder MS (APCI): 516/518 [M + H]⁺ |
| B41 | NH₂ | CH₂CH₂CF₃ | powder MS (APCI): 542/544 [M + H]⁺ |
| B42 | NH₂ | H₃C-(tetrahydrothiophene-SO₂) | powder MS (APCI): 592/594 [M + H]⁺ |
| B43 | NH₂ | cyclopentyl | powder MS (APCI): 528/530 [M + H]⁺ |

TABLE 26-continued

| B44 | —N(CH₃)₂ | CH(CH₃)CH₂CH₃ (with CH₃) | powder MS (APCI): 544/546 [M + H]⁺ |
|---|---|---|---|
| B45 | —N(CH₃)₂ | CH₂CH₂CF₃ | powder MS (APCI): 570/572 [M + H]⁺ |
| B46 | —N(CH₃)₂ | (tetrahydrothiophene-SO₂) | powder MS (APCI): 606/608 [M + H]⁺ |
| B47 | —N(CH₃)₂ | cyclopentyl | powder MS (APCI): 556/558 [M + H]⁺ |

(No. 2)

| Ex. Nos. | $R^U$ | Physicochemical properties etc. |
|---|---|---|
| B48 | CH(CH₃)CH₂CH₃ | powder MS (APCI): 530/532 [M + H]⁺ |
| B49 | CH₂CH₂CF₃ | powder MS (APCI): 556/558 [M + H]⁺ |
| B50 | (tetrahydrothiophene-SO₂) | powder MS (APCI): 592/594 [M + H]⁺ |
| B51 | cyclopentyl | powder MS (APCI): 542/544 [M + H]⁺ |

Examples B52 to B53

The corresponding starting materials were treated in the same manner as described in Example A41 to give following compounds.

Example B52

2-carbamoyl-6-(2-chlorophenyl)-7-(4-trifluoromethylphenyl)-3-[N-(1,1-dioxo-thiacyclobutan-3-yl)carbamoyl]pyrazolo[1,5-a]pyrimidine (powder)

MS (APCI) m/z; 564/566 [M+H]⁺

Example B53

6-(2-chlorophenyl)-7-(4-trifluoromethylphenyl)-2-hydroxymethyl-3-[N-(1,1-dioxothiacyclobutan-3-yl)-carbamoyl]pyrazolo[1,5-a]pyrimidine (powder)

MS (APCI) m/z; 551/553 [M+H]$^+$

Examples B54 to B120

The corresponding starting materials were treated in the same manner as described in Example A1 to give compounds as shown in the following Table 27.

TABLE 27

(No. 1)

| Ex. Nos. | $R^U$ | Physicochemical properties etc. |
|---|---|---|
| B54 | (1-methyl-1-(pyridin-2-yl)ethyl) | powder MS (APCI): 566/568 [M + H]$^+$ |
| B55 | (3-methyl-1,1-dioxothiolan-3-yl) | powder MS (APCI): 579/581 [M + H]$^+$ |
| B56 | (1-cyano-1-methylcyclohexyl) | powder MS (APCI): 554/556 [M + H]$^+$ |
| B57 | (pyrrolidin-1-yl) | powder MS (APCI): 516/518 [M + H]$^+$ |
| B58 | (1,1-dioxothiomorpholin-4-yl) | powder MS (APCI): 580/582 [M + H]$^+$ |
| B59 | (3-methylbutan-2-yl) | powder MS (APCI): 503/505 [M + H]$^+$ |
| B60 | (3,3,3-trifluoropropyl) | powder MS (APCI): 529/531 [M + H]$^+$ |

TABLE 27-continued (No. 2)

| Ex. Nos. | $R^U$ | Physicochemical properties etc. |
|---|---|---|
| B61 | (1,1-dioxothiomorpholin-4-yl) | powder MS (APCI): 595/597 [M + H]$^+$ |
| B62 | (2-cyanoethyl) | powder MS (APCI): 501/503 [M + H]$^+$ |
| B63 | (tetrahydrofuran-2-ylmethyl) | powder MS (ESI): 546 [M + H]$^+$ |
| B64 | (2-methylbutan-2-yl with extra CH3) | powder MS (ESI): 532 [M + H]$^+$ |
| B65 | CH$_3$ | powder MS (ESI): 476 [M + H]$^+$ |
| B66 | (cyclohexylmethyl) | powder MS (ESI): 558 [M + H]$^+$ |
| B67 | (3,3,3-trifluoropropyl) | powder MS (ESI): 544 [M + H]$^+$ |
| B68 | (isobutyl) | powder MS (ESI): 518 [M + H]$^+$ |
| B69 | (2-fluoroethyl) | powder MS (ESI): 508 [M + H]$^+$ |

(No. 3)

| Ex. Nos. | R' | $R^U$ | Physicochemical properties etc. |
|---|---|---|---|
| B70 | Cl | (2,2-difluoroethyl) | powder MS (ESI): 526 [M + H]$^+$ |
| B71 | Cl | (2-hydroxy-2-methylbutyl) | powder MS (ESI): 534 [M + H]$^+$ |

TABLE 27-continued

| Ex. Nos. | R¹ | R^U | Physicochemical properties etc. |
|---|---|---|---|
| B72 | Cl | 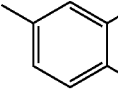 | powder MS (APCI): 574/576 [M + H]+ |
| B73 | Cl |  | powder MS (APCI): 516/518 [M + H]+ |
| B74 | Cl | 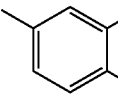 | powder MS (APCI): 516/518 [M + H]+ |
| B75 | F |  | powder MS (APCI): 564/566 [M + H]+ |
| B76 | CHF₂ | 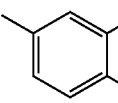 | powder MS (APCI): 534/536 [M + H]+ |

(No. 4)

| Ex. Nos. | R¹ | R^U | Physicochemical properties etc. |
|---|---|---|---|
| B77 | 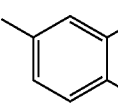 |  | powder MS (APCI): 536/538 [M + H]+ |
| B78 | 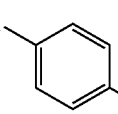 |  | powder MS (APCI): 562/564 [M + H]+ |
| B79 | 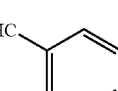 |  | powder MS (APCI): 598/600 [M + H]+ |
| B80 | 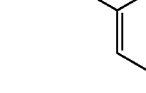 | 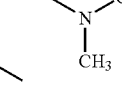 | powder MS (APCI): 549/551 [M + H]+ |
| B81 | 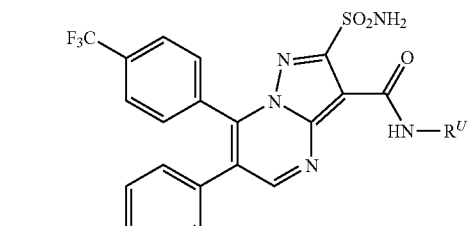 | 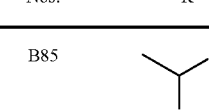 | powder MS (APCI): 505/507 [M + H]+ |
| B82 | 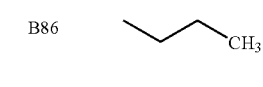 |  | powder MS (APCI): 560/562 [M + H]+ |
| B83 | 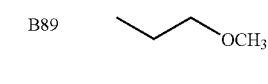 |  | powder MS (APCI): 546/548 [M + H]+ |
| B84 | 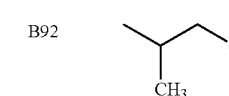 | 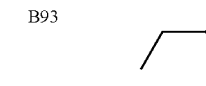 | powder MS (APCI): 521/523 [M + H]+ |

(No. 5)

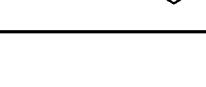

| Ex. Nos. | R^U | Physicochemical properties etc. |
|---|---|---|
| B85 |  | powder MS (ESI): 538 [M + H]+ |
| B86 | | powder MS (ESI): 538 [M + H]+ |
| B87 | | powder MS (ESI): 536 [M + H]+ |
| B88 | | powder MS (ESI): 550 [M + H]+ |
| B89 | | powder MS (ESI): 554 [M + H]+ |
| B90 | | powder MS (ESI): 552 [M + H]+ |
| B91 | | powder MS (ESI): 578 [M + H]+ |
| B92 | | powder MS (ESI): 552 [M + H]+ |
| B93 | | powder MS (ESI): 550 [M + H]+ |
| B94 | | powder MS (ESI): 560 [M + H]+ |

TABLE 27-continued

(No. 6)

Structure: 7-(4-trifluoromethylphenyl)-6-(2-chlorophenyl)pyrazolo[1,5-a]pyrimidine with 2-SO₂NH₂ and 3-C(O)NR^V R^U

| Ex. Nos. | —NR^V R^U | Physicochemical properties etc. |
|---|---|---|
| B95 | CH₃-NH-CH(CH₃)-CH₂-N(CH₃)₂ | powder MS (ESI): 581 [M + H]⁺ |
| B96 | CH₃-NH-CH(CH₃)-CH₂-OCH₃ | powder MS (ESI): 568 [M + H]⁺ |
| B97 | HN-(4,4-difluorocyclohexyl) | powder MS (ESI): 614 [M + H]⁺ |
| B98 | CH₃-HN-C(CH₃)(cyclopropyl) | powder MS (ESI): 550 [M + H]⁺ |
| B99 | CH₃-NH-CH₂-CH₃ | powder MS (APCI): 524/526 [M + H]⁺ |
| B100 | —N(NH)(CH₃)-pyridin-2-yl | powder MS (APCI): 602/604 [M + H]⁺ |
| B101 | (CH₃)₂N-C(CH₃)₂-pyridin-2-yl with N(CH₃) | powder MS (APCI): 629/631 [M + H]⁺ |
| B102 | H₃C-C(CH₃)(NH-)-pyridin-2-yl | powder MS (APCI): 615/617 [M + H]⁺ |
| B103 | CH₃-HN-N-pyrrolidinyl | powder MS (APCI): 565/567 [M + H]⁺ |

(No. 7)

Structure: 7-(4-R'-phenyl)-6-(2-chlorophenyl)pyrazolo[1,5-a]pyrimidine with 2-SO₂NH₂ and 3-C(O)NH-R^U

| Ex. Nos. | R' | R^U | Physicochemical properties etc. |
|---|---|---|---|
| B104 | —OCH₃ | CH(CH₃)-CH₂-OCH₃ | powder MS (APCI): 530/532 [M + H]⁺ |
| B105 | —OCH₃ | CH₂-CF₃ | powder MS (APCI): 540/542 [M + H]⁺ |
| B106 | —OCH₃ | CH(CH₃)-CH₂-CH₃ (sec-butyl) | powder MS (APCI): 514/516 [M + H]⁺ |
| B107 | —OCH₃ | cyclopentyl | powder MS (APCI): 526/528 [M + H]⁺ |
| B108 | CH₃ | CH(CH₃)-CH₂-OCH₃ | powder MS (APCI): 514/516 [M + H]⁺ |
| B109 | CH₃ | CH₂-CF₃ | powder MS (APCI): 524/526 [M + H]⁺ |
| B110 | CH₃ | CH(CH₃)-CH₂-CH₃ | powder MS (APCI): 498/500 [M + H]⁺ |
| B111 | CH₃ | cyclopentyl | powder MS (APCI): 510/512 [M + H]⁺ |

(No. 8)

Structure: 7-R¹-6-(2-chlorophenyl)pyrazolo[1,5-a]pyrimidine with 2-SO₂NH₂ and 3-C(O)NR^V R^U

| Ex. Nos. | R¹ | —NR^V R^U | Physicochemical properties etc. |
|---|---|---|---|
| B112 | piperidin-1-yl | H₃C-C(CH₃)(N(CH₃)-)-pyridin-2-yl | powder MS (APCI): 568/570 [M + H]⁺ |

TABLE 27-continued

| | | | |
|---|---|---|---|
| B113 | piperidine-N-CH(N(H)CH3)-CH(CH3)2 | powder | MS (APCI): 491/493 [M + H]+ |
| B114 | piperidine-N-CH(N(H)CH3)-CF3 | powder | MS (APCI): 517/519 [M + H]+ |
| B115 | piperidine-N-CH(N(H)CH3)-cyclopentyl | powder | MS (APCI): 503/505 [M + H]+ |
| B116 | F-C6H4-CH(N(H)CH3)-CH(CH3)2 | powder | MS (ESI): 502 [M + H]+ |
| B117 | F-C6H4-CH(N(H)CH3)-CF3 | powder | MS (ESI): 528 [M + H]+ |
| B118 | F-C6H4-CH(N(H)CH3)-CH(CH3)CH3 | powder | MS (ESI): 502 [M + H]+ |
| B119 | F-C6H4-CH(NH-CH2-cyclopropyl) | powder | MS (ESI): 500 [M + H]+ |
| B120 | F-C6H4-CH(NH-N(CH3)-2-pyridyl) | powder | MS (APCI): 552/554 [M + H]+ |

Example B121

Under nitrogen atmosphere, to a solution of cyclopentylamine (30 μL) in toluene (1.5 mL) was added a solution of 2M trimethylaluminum in toluene (0.15 mL), and the mixture was stirred at room temperature for 15 minutes. Thereto was added the compound obtained in Reference Example B21 (76 mg), and the mixture was stirred at room temperature for 1 hour and at 100° C. for 17 hours. After cooling to room temperature, the reaction mixture was diluted with ethyl acetate, and thereto was added an aqueous 20% Rochell salt solution. The mixture was extracted with chloroform, and the organic layer was concentrated in vacuo. The resultant crude product was purified by column chromatography on silica gel (solvent; chloroform/methanol 100/0 to 96/4) to give 6-(2-chlorophenyl)-3-[N-(cyclopentyl)carbamoyl]-7-(4-trifluoromethyl-phenyl)-2-ureidopyrazolo[1,5-a]pyrimidine (48 mg, yield: 59%) as a powder.

MS (APCI) m/z; 543/545 [M+H]+

Examples B122 to B125

The corresponding starting materials were treated in the same manner as described in Example B121 to give compounds as shown in the following Table 28.

TABLE 23

Structure: pyrazolo[1,5-a]pyrimidine core with F3C-C6H4-, 2-Cl-C6H4-, NHCONH2, and C(=O)NH-R^U substituents

| Ex. Nos. | $R^U$ | Physicochemical properties etc. |
|---|---|---|
| B122 | -CH(CH3)2 with CH3 | powder MS (APCI): 531/533 [M + H]+ |
| B123 | -CH2CF3 | powder MS (APCI): 557/559 [M + H]+ |
| B124 | tetrahydrothiophene-SO2 | powder MS (APCI): 593/595 [M + H]+ |
| B125 | -N(CH3)2 | powder MS (APCI): 518/520 [M + H]+ |

Reference Example A1

(1) To diethylether (250 mL) was added magnesium (6.04 g) and a catalytic amount of iodine, and the mixture was stirred. Thereto was gradually added dropwise 2-chlorobenzyl chloride (20.0 g), and the mixture was stirred for 1 hour from the time when the temperature of such mixture began to rise. Thereto was added a solution of 4-chlorobenzonitrile (18.8 g) in tetrahydrofuran/diethylether (20 mL/50 mL), and the mixture was stirred for 3 hours. To the reaction mixture was added an aqueous 2N hydrochloric acid solution (150 mL) under ice-cooling, and the mixture was stirred at room temperature for 2 hours. The reaction mixture was extracted with ethyl acetate, and the organic layer was washed successively with water and brine, dried over magnesium sulfate and filtered. The filtrate was concentrated in vacuo, and the resultant crude product was purified by column chromatography on silica gel (solvent: hexane/ethyl acetate=40/1 to 20/1) to obtain (2-chlorobenzyl)(4-chlorophenyl)methanone (24.40 g; yield: 74%) as a powder.

MS (APCI) m/z; 265/267 [M+H]+

(2) A solution of the compound obtained in the above step (1) (6.4 g) and N,N-dimethylformamide dimethylacetal (6.4 mL) in N,N-dimethylformamide (24 mL) was stirred at 150° C. for 4 hours. After cooling the reaction mixture to room temperature, thereto was added water, and the mixture was extracted with a mixture of ethyl acetate and hexane (x 3). The organic layer was washed with brine, dried over magnesium sulfate and filtered. The filtrate was concentrated in vacuo to obtain 1-(4-chlorophenyl)-2-(2-chlorophenyl)-3-(N,N-dimethylamino)-2-propen-1-one as an oil.

(3) The compound obtained in the above step (2) was dissolved in acetic acid (8 mL), and thereto were added 3-amino-4-ethoxycarbonyl-1H-pyrazole (3.75 g) and piperidine (0.48 mL). The mixture was heated at 80° C. for 16 hours. After cooling to room temperature, to the reaction mixture were added water and ethyl acetate. After stirring, the organic layer was washed with brine, dried over magnesium sulfate and filtered. The filtrate was concentrated in vacuo, and the resultant crude product was purified by column chromatography on silica gel (solvent: hexane/ethyl acetate=17/3 to 67/33) to give 6-(2-chlorophenyl)-7-(4-chlorophenyl)-3-ethoxycarbonylpyrazolo[1,5-a]pyrimidine (5.02 g, yield in combined steps (2) and (3): 50%) as a powder.

MS (APCI) m/z; 412/414 [M+H]$^+$ (4) To a solution of the compound obtained in the above step (3) (2.5 g) in ethanol (30 mL) was added an aqueous 2N sodium hydroxide solution (6 mL), and the mixture was stirred at room temperature for 5 hour. To the reaction mixture was added an aqueous 2N hydrochloric acid solution, and the mixture was stirred and concentrated in vacuo. The residue was extracted with ethyl acetate, and the organic layer was washed with brine, dried over magnesium sulfate and filtered. The filtrate was concentrated in vacuo to obtain 3-carboxy-6-(2-chlorophenyl)-7-(4-chlorophenyl)-pyrazolo[1,5-a]pyrimidine (2.1 g, yield: 90%) as a powder.

MS (APCI) m/z; 384/386 [M+H]$^+$

Reference Example A2

(1) To dimethoxyethane (100 mL) were added 4-chlorobenzyl bromide (4.1 g), 4-chlorobenzoyl chloride (2.56 mL), bis(triphenylphosphine)palladium dichloride (702 mg) and zinc powder (2.6 g), and the mixture was stirred for 2 hours under nitrogen atmosphere. The reaction mixture was filtered and the filtrate was concentrated in vacuo and extracted with ethyl acetate. The organic layer was washed with brine, dried over magnesium sulfate and filtered. The filtrate was concentrated in vacuo, and the resultant crude product was purified by column chromatography on silica gel (solvent: hexane/ethyl acetate=49/1 to 9/1) to give (2-chlorobenzyl)(4-chlorophenyl)-methanone (4.85 g, yield: 91%) as a powder.

MS (GC-EI) m/z; 264 [M]$^+$ (2) The compound obtained in the above step (1) was treated in the same manner as described in Reference Example 1(2) to (4) to give 3-carboxyl-6-(2-chlorophenyl)-7-(4-chlorophenyl)pyrazolo[1,5-a]pyrimidine.

Reference Example A3

(1) To a solution of potassium cyanide (5.6 g) and ammonium chloride (5.06 g) in water (17 mL) was added a solution of tetrahydro-4H-thiopyran-4-one (10 g) in methanol (22 mL), and the mixture was refluxed under heating overnight. After cooling to room temperature, to the reaction mixture was added an aqueous 1N sodium hydroxide solution, and the mixture was extracted with diethylether. The organic layer was dried over magnesium sulfate and filtered. The filtrate was concentrated in vacuo, and to a solution of the resultant residue in diethylether was added a solution of 4N hydrochloric acid in ethyl acetate. The precipitates were collected by filtration to give 4-amino-tetrahydrothiopyran-4-carbonitrile (13.6 g, yield: 88%) as a colorless solid.

MS (APCI) m/z; 143 [M+H]$^+$ (2) A solution of the compound obtained in the above step (1) (10.5 g) in an aqueous 6N hydrochloric acid (500 mL) was refluxed under heating overnight. After cooling to room temperature, the reaction mixture was concentrated in vacuo, and the residue was dried to give 4-amino-tetrahydrothiopyran-4-carboxylic acid (10.6 g) as a crude product.

MS (APCI) m/z; 162 [M+H]$^+$ (3) To a solution of the compound obtained in the above step (2) (10.6 g) in methanol (70 mL) was gradually added dropwise thionyl chloride (5.7 mL), and the mixture was refluxed under heating overnight. After cooling to room temperature, the reaction mixture was concentrated in vacuo. The residue was washed with ethyl acetate/diethylether, and thereto was added an aqueous 1N sodium hydroxide solution. The mixture was extracted with chloroform, and the organic layer was dried over magnesium sulfate and filtered. The filtrate was concentrated in vacuo to give methyl 4-amino-tetrahydrothiopyran-4-carboxylate (3.83 g, yield: 39%) as a brown oil.

MS (APCI) m/z; 176 [M+H]$^+$ (4) To a solution of the compound obtained in the above step (3) (100 mg) in methylene chloride (4 mL) was gradually added m-chloroperbenzoic acid (394 mg), and the mixture was stirred at room temperature for 30 minutes. To the reaction mixture was added methanol (4 mL) and thereto was gradually added PL-HCO$_3$ MP resin (0.9 g, Polymer Labs.) The mixture was stirred overnight. The reaction mixture was filtered, and the filtrate was concentrated in vacuo. The resultant crude product was purified by column chromatography on silica gel (solvent: hexane/ethyl acetate=30/70 to 0/100) to give methyl 4-amino-1,1-dioxo-tetrahydrothiopyran-4-carboxylate (38 mg, yield: 32%) as a colorless solid.

MS (ESI) m/z; 208 [M+H]$^+$

Reference Example A4

A solution of ethyl 2-cyano-3,3-bismethylthioacrylate (40.0 g), hydrazine hydrochloride (12.6 g) and sodium acetate (22.6 g) in ethanol (700 mL) was stirred at 90° C. for 2 hours. After cooling to room temperature, the reaction mixture was concentrated in vacuo, and to the residue were added water and ethyl acetate. The organic layer was separated, dried over magnesium sulfate and filtered. The filtrate was concentrated in vacuo, and to the residue was added ethyl acetate and hexane. The precipitates were collected by filtration and dried to give 3-amino-4-ethoxycarbonyl-5-methylthiopyrazole (17.4 g, yield: 47%) as a colorless solid.

MS (APCI) m/z; 202 [M+H]$^+$

Reference Example A5

(1) 2-Chlorobenzyl chloride (50 g) and 4-trifluoromethylbenzonitrile (53.1 g) were treated in the same manner as described in Reference Example A1-(1) to give (2-chlorobenzyl)(4-trifluoromethylphenyl)methanone (42.5 g, yield: 46%) as a powder.

(2) The compound obtained in the above step (1) (15.1 g) and N,N-dimethylformamide dimethylacetal (12.1 g) were treated in the same manner as described in Reference Example A1-(2) to give 2-(2-chlorophenyl)-1-(4-trifluoromethylphenyl)-3-(N,N-dimethylamino)-2-propen-1-one (17.7 g) as a crude oil.

(3) The compound obtained in the above step (2) (17.7 g) and the compound obtained in Reference Example A4 (10.2 g) were treated in the same manner as described in Reference Example A1-(3) to give 6-(2-chlorophenyl)-3-ethoxycarbonyl-7-(4-trifluoromethylphenyl)-2-methylthiopyrazolo[1,5-a]pyrimidine (12.2 g, yield: 46%) as a powder.

MS (APCI) m/z; 492/494 [M+H]$^+$

Reference Example A6

(1) To a solution of 6-(2-chlorophenyl)-3-ethoxycarbonyl-7-(4-trifluoromethyl-phenyl)-2-methylthiopyrazolo[1,5-a]

pyrimidine (compound obtained in Reference Example A5; 11.0 g) in methylene chloride (400 mL) was added m-chloroperbenzoic acid (16.5 g) at 0° C., and the mixture was stirred at room temperature for 3 hours. To the reaction mixture was added dropwise an aqueous sodium thiosulfate solution at 0° C. under stirring, and the mixture was extracted with ethyl acetate. The organic layer was dried over magnesium sulfate and filtered. The filtrate was concentrated in vacuo, and the resultant crude product was washed with ethanol to give 6-(2-chlorophenyl)-3-ethoxycarbonyl-7-(4-trifluoromethylphenyl)-2-methylsulfonylpyrazolo[1,5-a]pyrimidine (10.7 g, yield: 91%) as a powder.

(2) To a solution of the compound obtained in the above step (1) (10.7 g) in dimethylformamide (120 mL) was added sodium azide (5.3 g), and the mixture was stirred at 110° C. for 3 hours. After cooling to room temperature, to the reaction mixture was added water. After stirring, the mixture was extracted with ethyl acetate, and the organic layer was washed with water and concentrated in vacuo. The resultant crude product was purified by column chromatography on silica gel (solvent: hexane/ethyl acetate=80/20 to 65/35) to give 2-azido-6-(2-chlorophenyl)-3-ethoxycarbonyl-7-(4-trifluoromethylphenyl)pyrazolo[1,5-a]pyrimidine (9.7 g, yield: 98%) as a pale yellow solid.

(3) To a solution of the compound obtained in the above step (2) (9.7 g) in tetrahydrofuran (150 mL) was added triphenylphosphine (10.5 g), and the mixture was stirred at 60° C. for 1 hour. After cooling to room temperature, the reaction mixture was concentrated in vacuo, and the resultant crude product was purified by column chromatography on silica gel (solvent: hexane/ethyl acetate=90/10 to 0/100) to give 6-(2-chlorophenyl)-3-ethoxycarbonyl-7-(4-trifluoromethylphenyl)-2-(N-triphenylphosphoranylidenamino)pyrazolo[1,5-a]pyrimidine (11.1 g, yield: 77%) as a yellow solid.

(4) A solution of the compound obtained in the above step (3) (11.1 g) in tetrahydrofuran (28 mL), acetic acid (70 mL) and water (42 mL) was stirred at 100° C. overnight. After cooling to room temperature, the reaction mixture was concentrated in vacuo, and the resultant crude product was purified by column chromatography on silica gel (solvent: hexane/ethyl acetate=85/15 to 60/40) to give 2-amino-6-(2-chlorophenyl)-3-ethoxycarbonyl-7-(4-trifluoromethylphenyl)pyrazolo[1,5-a]pyrimidine (5.2 g, yield: 73%) as a yellow solid.

MS (APCI) m/z; 461/463 [M+H]$^+$

Reference Example A7

(1) To a solution of 1-methylcyclopropanecarboxylic acid (3.52 g) in tert-butanol (50 mL) were added diphenylphosphoryl azide (7.58 mL) and triethylamine (4.90 mL), and the mixture was stirred at 80° C. for 15 hours. After cooling to room temperature, the reaction mixture was concentrated in vacuo. To the residue were added water and an aqueous saturated sodium hydrogencarbonate solution, and the mixture was extracted with diethylether. The organic layer was dried over magnesium sulfate and filtered. The filtrate was concentrated in vacuo, and the resultant crude product was purified by column chromatography on silica gel (solvent: hexane/ethyl acetate=90/10 to 87/13) to give 1-methyl-1-[N-(tert-butoxycarbonyl)amino]-cyclopropane (4.66 g, yield: 77%) as a colorless solid.

MS (APCI) m/z; 172 [M+H]$^+$ (2) To a solution of the compound obtained in the above step (1) (4.66 g) in 1,4-dioxane (10 mL) was added a solution of 4N hydrochloric acid in dioxane (10 mL), and the mixture was stirred at room temperature overnight. To the reaction mixture was added diisopropylether, and the precipitated crystals were collected by filtration to give 1-methylcyclopropylamine hydrochloride (2.69 g, yield: 92%) as a colorless solid.

MS (APCI) m/z; 72 [M+H]$^+$

Reference Example A8

Under nitrogen atmosphere, a solution of anhydrous cerium chloride (5.0 g) in tetrahydrofuran (40 mL) was stirred at room temperature overnight. To the reaction mixture was added dropwise a solution of 1.04M methyl lithium in diethylether (19 mL) under cooling in a dry ice/acetone bath over a period of 20 minutes. The mixture was stirred at the same temperature for 30 minutes, and to the reaction mixture was added dropwise a solution of 2-cyanopyridine (685 mg) in tetrahydrofuran (1 mL). After warming to room temperature over a period of 5 hours, to the reaction mixture was added an aqueous 28% ammonia solution (12.5 mL) under ice-cooling. The mixture was filtered through Celite to remove precipitates. The filtrate was dried over sodium sulfate and filtered. The filtrate was concentrated in vacuo to give 1-methyl-1-(2-pyridyl)ethylamine (863 mg) as a brown oil.

MS (APCI) m/z; 137 [M+H]$^+$

Reference Example A9

To a solution of 1-aminocyclohexanecarboxylic acid (600 mg) in tetrahydrofuran-methanol was added dropwise trimethylsilyl diazomethane (4.2 mL) under ice-cooling and stirring, and the mixture was stirred overnight. The reaction mixture was concentrated in vacuo, and to the residue were added successively diethylether-hexane (1/1) and a solution of 4N hydrochloric acid in ethyl acetate (1.05 mL). The precipitates were collected by filtration and dried to give methyl 1-amino-cyclohexanecarboxylate (423 mg, yield: 52%) as a white powder.

MS (APCI) m/z; 158 [M+H]$^+$

Reference Examples A10 to A13

The corresponding starting materials were treated in the same manner as described in Reference Example A1 to give compounds as shown in the following Table 29.

TABLE 29

| Ref. Ex. Nos. | R$^1$ | R$^0$ | Physicochemical properties etc. |
|---|---|---|---|
| A10 | F$_3$C-(4-methylphenyl) | H | MS (APCI): 418/420 [M + H]$^+$ |

TABLE 29-continued

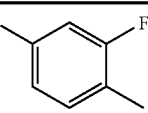

| Ref. Ex. Nos. | R¹ | R⁰ | Physicochemical properties etc. |
|---|---|---|---|
| A11 | 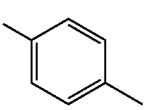 | H | MS (APCI): 402/404 [M + H]⁺ |
| A12 | 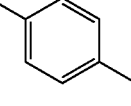 | CH₃ | MS (APCI): 432/434 [M + H]⁺ |
| A13 | 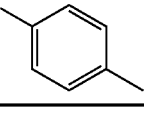 | CH₃ | MS (APCI): 398/400 [M + H]⁺ |

Reference Example A14

(1) To a solution of methyl 2-chlorophenylacetate (10 g) in dimethylformamide (150 mL) was added N,N-dimethylformamide dimethylacetal (14.4 mL), and the mixture was stirred at 85° C. overnight. After cooling to room temperature, to the reaction mixture was added ethyl acetate and water. After stirring, the organic layer was separated, dried over sodium sulfate and filtered, and the filtrate was concentrated in vacuo. The residue was diluted with acetic acid (18 mL), and thereto were added 3-amino-4-ethoxycarbonyl-1H-pyrazole (8.4 g) and piperidine (1.1 mL). The mixture was stirred at 80° C. for 3.5 hours. After cooling to room temperature, to the reaction mixture were added ethyl acetate and water. The mixture was stirred and filtered, and the resultant precipitates were dried to give 3-[2-(2-chlorophenyl)-2-methoxycarbonyl-vinylamino]-4-ethoxycarbonyl-1H-pyrazole (11.8 g, yield: 62%) as a powder.

MS (APCI) m/z; 350/352 [M+H]⁺

(2) To a solution of the compound obtained in the above step (1) (10.7 g) in ethanol (250 mL) was added sodium carbonate (3.24 g), and the mixture was refluxed under heating for 4 days. After cooling to room temperature, the reaction mixture was filtered and the filtrate was concentrated in vacuo. To the residue was added water, and the mixture was stirred and filtered (said filtration procedure was repeated in five times). The resultant precipitates were dried to give 6-(2-chlorophenyl)-3-ethoxycarbonyl-7-oxo-4,7-dihydropyrazolo[1,5-a]pyrimidine (8.5 g, yield: 87%) as a powder.

MS (APCI) m/z; 318/320 [M+H]⁺

(3) To a solution of the compound obtained in the above step (2) (300 mg) in acetonitrile (2 mL) were added N,N-dimethylaniline (319 μL) and phosphorus oxychloride (270 μL), and the mixture was refluxed under heating for 1 day. After cooling to room temperature, the reaction mixture was poured in ice-water, and the mixture was extracted with methylene chloride. The extract was dried over magnesium sulfate and filtered. The filtrate was concentrated in vacuo, and the resultant crude product was purified by column chromatography on silica gel (solvent: hexane/ethyl acetate=80/20 to 60/40) to give 7-chloro-6-(2-chlorophenyl)-3-ethoxycarbonylpyrazolo[1,5-a]pyrimidine (108 mg, yield: 34%) as a powder.

MS (APCI) m/z; 336/338 [M+H]⁺

(4) To a solution of the compound obtained in the above step (3) (500 mg) in dimethylformamide (6 mL) were added 4-pipecoline (210 μL) and potassium carbonate (412 mg), and the mixture was stirred at 80° C. for 2.5 hours. After cooling to room temperature, to the reaction mixture was added water, and the mixture was extracted with ethyl acetate. The organic layer was washed successively with water and brine, dried over sodium sulfate and filtered. The filtrate was concentrated in vacuo, and the resultant crude product was purified by column chromatography on silica gel (solvent: hexane/ethyl acetate=80/20 to 50/50) to give 6-(2-chlorophenyl)-3-ethoxycarbonyl-7-(4-methylpiperidin-1-yl)pyrazolo[1,5-a]pyrimidine (593 mg, yield: 99%) as an oil.

MS (APCI) m/z; 399/401 [M+H]⁺

(5) The compound obtained in the above step (4) (593 mg) was treated in the same manner as described in Reference Example 1-(4) to give 3-carboxy-6-(2-chlorophenyl)-7-(4-methylpiperidin-1-yl)pyrazolo[1,5-a]pyrimidine (500 mg, yield: 91%) as a colorless solid MS (APCI) m/z; 371/373 [M+H]⁺

Reference Example A14B

To a solution of methyl 2-chlorophenylacetate (25 g) in dimethylformamide (400 mL) was added N,N-dimethylformamide dimethylacetal (36 mL), and the mixture was stirred at 90° C. overnight. After cooling to room temperature, to the reaction mixture were added ethyl acetate and water. After stirring, the organic layer was separated, dried over magnesium sulfate and filtered, and the filtrate was concentrated in vacuo. The residue was diluted with acetic acid (60 mL), and thereto was added 3-amino-4-ethoxycarbonyl-5-methyl-1H-pyrazole (19.7 g). The mixture was stirred at 120° C. overnight. After cooling the reaction mixture to room temperature, the precipitates were collected by filtration, washed with ethyl acetate/diisopropylether (1/1) and dried to give 6-(2-chlorophenyl)-3-ethoxycarbonyl-2-methyl-7-oxo-4,7-dihydropyrazolo[1,5-a]pyrimidine (26.0 g) as a powder.

MS (APCI) m/z; 332/334 [M+H]⁺

Reference Examples A15 to A16

The corresponding starting materials were treated in the same manner as described in Reference Example A14 or A14B and then each of the reaction product was treated in the same manner as described in Reference Example A14-(3) to (4) to give compounds as shown in the following Table 30.

TABLE 30

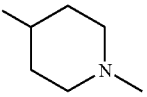

| Ref. Ex. Nos. | R¹ | Physicochemical properties etc. |
|---|---|---|
| A15 | 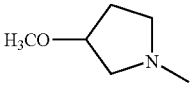 | MS (APCI): 387/389 [M + H]⁺ |
| A16 | 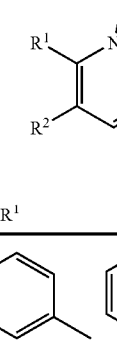 | MS (APCI): 373/375 [M + H]⁺ |

Reference Example A17

(1) The corresponding starting materials were treated in the same manner as described in Reference Example A1-(1) to give (2-chlorobenzyl)(4-trifluoromethyl-phenyl)methanone.

(2) The compound obtained in the above step (1) (3.0 g) and N,N-dimethylformamide dimethylacetal were treated in the same manner as described in Reference Example A1-(2), and then the reaction product and 3-amino-5-methyl-1H-pyrazole (977 mg) were treated in the same manner as described in Reference Example A1-(3) to give 6-(2-chlorophenyl)-7-(4-trifluoromethylphenyl)-2-methyl-pyrazolo[1,5-a]pyrimidine (2.63 g, yield: 67%) as a brown oil.

MS (APCI) m/z; 388/390 [M+H]⁺

(3) To a solution of the compound obtained in the above step (3) (2.27 g) in chloroform (50 mL) was gradually added dropwise chlorosulfonic acid (1.35 mL), and the mixture was stirred at 70° C. for 3.5 hours. The re-action mixture was concentrated in vacuo, and to the residue was added thionyl chloride (20 mL). The mixture was refluxed under heating for 2 hours. The reaction mixture was concentrated in vacuo, and to the residue was added ice-water. The mixture was extracted with chloroform, and the organic layer was dried over sodium sulfate and filtered. The filtrate was concentrated in vacuo, and the resultant crude product was purified by column chromatography on silica gel (solvent: hexane/ethyl acetate=85/15 to 60/40) to give 6-(2-chlorophenyl)-3-chlorosulfonyl-7-(4-trifluoromethylphenyl)-2-methylpyrazolo[1,5-a]pyrimidine (2.71 g, yield: 95%) as a pale yellow solid.

MS (APCI) m/z; 486/488 [M+H]⁺

Reference Examples A18 to A20

The corresponding starting materials were treated in the same manner as described in Reference Example A1 to give compounds as shown in the following Table 31.

TABLE 31

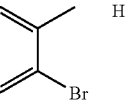

| Ref. Ex. Nos. | R¹ | R² | R⁰ | Physicochemical properties etc. |
|---|---|---|---|---|
| A18 | 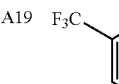 | 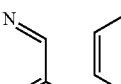 | H | MS (APCI): 428/430 [M + H]⁺ |
| A19 | 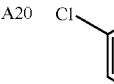 | 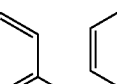 | CH₃ | MS (APCI): 433/435 [M + H]⁺ |
| A20 | 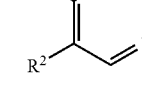 | 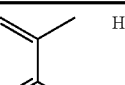 | C₂H₅ | MS (APCI): 412/414 [M + H]⁺ |

Reference Examples A21 to A22

The corresponding starting materials were treated in the same manner as described in Reference Example A2 to give compounds as shown in the following Table 32.

TABLE 32

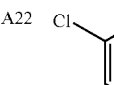

| Ref. Ex. Nos. | R¹ | R² | R⁰ | Physicochemical properties etc. |
|---|---|---|---|---|
| A21 | F₃C, F | F, Cl | H | MS (ESI): 434/436 [M + H]⁺ |
| A22 | Cl, F | F, Cl | CH₃ | MS (APCI): 416/418 [M + H]⁺ |

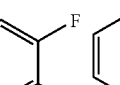

Reference Example A23

(1) To a solution of methyl 2-chlorophenylacetate (7.4 g) in dimethylformamide (110 mL) was added N,N-dimethylformamide dimethylacetal (10.6 mL), and the mixture was stirred at 90° C. overnight. After cooling to room temperature, to the reaction mixture was added water, and the mixture was extracted with ethyl acetate/hexane (4/1, 20 mL×1 and 100 mL×2). The combined organic layer was washed successively with water and brine, dried over magnesium sulfate and filtered. The filtrate was concentrated in vacuo. The residue was diluted with acetic acid (18 mL), and thereto was added 3-amino-4-ethoxycarbonyl-1H-pyrazole (6.2 g). The mixture was stirred at 110° C. overnight. After cooling the reaction mixture to room temperature, the precipitates were collected by filtration, washed successively with ethyl acetate and diisopropylether and dried to give 6-(2-chlorophenyl)-3-ethoxycarbonyl-7-oxo-4,7-dihydropyrazolo[1,5-a]pyrimidine (9.9 g, yield: 78%) as a powder.

MS (APCI) m/z; 318/320 [M+H]$^+$ (2) The compound obtained in the above step (1) (4.8 g) was treated in the same manner as described in Reference Example A14-(3) to give 7-chloro-6-(2-chlorophenyl)-3-ethoxycarbonylpyrazolo[1,5-a]pyrimidine (4.2 g, yield: 85%) as a powder.

MS (APCI) m/z; 336/338 [M+H]$^+$ (3) A solution of the compound obtained in the above step (2) (840 mg), [1,1-bis(diphenylphosphino)ferrocene]-dichloropalladium (II)-methylene chloride complex (61 mg), potassium phosphate (1.6 g) and 2-fluoro-4-formylphenylboronic acid (462 mg) in 1,4-dioxane (25 mL) was stirred at 80° C. under nitrogen atmosphere overnight. After cooling to room temperature, to the reaction mixture were added ethyl acetate and an aqueous saturated sodium hydrogencarbonate solution. The organic layer was separated, washed successively with water and brine, dried over magnesium sulfate and filtered. The filtrate was concentrated in vacuo, and the resultant crude product was purified by column chromatography on silica gel (solvent: hexane/ethyl acetate=70/30 to 50/50) to give 6-(2-chlorophenyl)-3-ethoxycarbonyl-7-(2-fluoro-4-formylphenyl)-pyrazolo[1,5-a]pyrimidine (665 mg, yield: 63%) as a powder.

MS (APCI) m/z; 424/426 [M+H]$^+$ (4) To a solution of the compound obtained in the above step (3) (660 mg) in methylene chloride (0.7 mL) was added bis(2-methoxyethyl)aminosulfur trifluoride (783 μL, Trade Name Deoxo-Fluor, Scott Inc.), and the mixture was stirred at room temperature for 1 day. To the reaction mixture was added an aqueous saturated sodium hydrogencarbonate solution under ice-cooling, and the mixture was stirred for 10 minutes. The mixture was extracted with methylene chloride, and the organic layer was concentrated in vacuo. The resultant crude product was purified by column chromatography on silica gel (solvent: hexane/ethyl acetate=75/25 to 60/40) to give 6-(2-chlorophenyl)-3-ethoxycarbonyl-7-(2-fluoro-4-difluoromethylphenyl)pyrazolo[1,5-a]pyrimidine (295 mg, yield: 42%) as a powder.

MS (APCI) m/z; 446/448 [M+H]$^+$ (5) The compound obtained in the above step (4) (290 mg) was treated in the same manner as described in Reference Example A1-(4) to give 3-carboxy-6-(2-chlorophenyl)-7-(2-fluoro-4-difluoromethylphenyl)-pyrazolo[1,5-a]pyrimidine (208 mg, yield: 77%) as a solid.

MS (APCI) m/z; 418/420 [M+H]$^+$

Reference Example A24

The corresponding starting materials were treated in the same manner as described in Reference Example A23-(1) to (3), and then the reaction product was treated in the same manner as described in Reference Example A23-(5) to give 3-carboxy-6-(2-chlorophenyl)-2-methyl-7-phenylpyrazolo[1,5-a]pyrimidine (250 mg, yield: 94%) as a solid.

MS (APCI) m/z; 364/366 [M+H]$^+$

Reference Example A25

(1) Under nitrogen atmosphere, to a solution of sodium ethoxide (14.32 g) in ethanol (20 mL) was added dropwise ethyl cyanoacetate (4.7 mL), and the mixture was stirred at room temperature for 1 hour. To the reaction mixture was added difluoroacetic acid (4.85 mL), and the mixture was stirred at room temperature for 4 hours and at 60° C. (external temperature) for 17 hours. The reaction mixture was concentrated in vacuo, and to the residue were added toluene (10 mL) and phosphorus chloride (3.2 g). The mixture was stirred at 45° C. for 1 hour. To the reaction mixture was further added phosphorus chloride (1.9 g), and the mixture was stirred at 55° C. for 2 hours. The reaction mixture was cooled in an ice-bath and filtered through Celite, and the filtrate was concentrated in vacuo. To the residue were added ethanol (20 mL), hydrazine monohydrate (0.8 mL) and triethylamine (3.0 mL), and the mixture was stirred at 60° C. for 2 hours. After cooling to room temperature, thereto were added an aqueous saturated sodium hydrogencarbonate solution and water, and the mixture was extracted with chloroform (×4). The combined organic layer was dried over sodium sulfate and filtered. The filtrate was concentrated in vacuo, and the resultant crude product was purified by column chromatography on silica gel (solvent: chloroform/methanol=100/0 to 94/6) and washed with chloroform to give 3-amino-4-ethoxycarbonyl-5-difluoromethyl-1H-pyrazole (1.26 g, yield: 41%) as a colorless solid.

MS (APCI) m/z; 206 [M+H]$^+$ (2) The compound obtained in the above step (1) (400 mg) was treated in the same manner as described in Reference Example A1-(2) to (3) to give 3-carboxy-6-(2-chlorophenyl)-7-(4-chlorophenyl)-2-difluoromethylpyrazolo[1,5-a]pyrimidine (405 mg, yield: 48%) as a powder.

MS (APCI) m/z; 434/436 [M+H]$^+$

Reference Example A26

(1) To a solution of methyl cyanoacetate (14.6 g) in methylene chloride (260 mL) was added trifluoroacetic anhydride (37.2 g), and the mixture was stirred at room temperature. Thereto was gradually added dropwise triethylamine (51.7 mL) at 0° C., and the mixture was stirred at room temperature overnight. To the reaction mixture was added water, and the mixture was extracted with methylene chloride. The organic layer was dried over magnesium sulfate and filtered. The filtrate was concentrated in vacuo to give a mixture (55.3 g) of methyl 2-cyano-2-(2-trifluoroacetyl)acetate (compound 2a) and methyl 2-cyano-4,4,4-trifluoro-3-trifluoromethoxycarbonyl-2-butenoate (compound 2b).

Compound 2a: MS (APCI) m/z; 196 [M+H]$^+$
Compound 2b: MS (APCI) m/z; 292 [M+H]$^+$ (2) To a mixture of the compound 2a and 2b obtained in the above step (1) (27.6 g) in methylene chloride (200 mL) were gradually added dropwise oxalyl chloride (31.6 mL) and a few drops of pyridine, and the mixture was refluxed under heating for 4 hours. The reaction mixture was gradually poured in water, and the mixture was extracted with methylene chloride. The organic layer was dried over magnesium sulfate and filtered. The filtrate was concentrated in vacuo to give methyl 3-chloro-2-cyano-4,4,4-trifluoro-2-butenoate as a crude product.

(3) To the compound obtained in the above step (2) was added water (20 mL), and thereto was gradually added dropwise hydrazine monohydrate (80%, 6.74 g) at 0° C. To the mixture was added triethylamine (2 mL) at room temperature, and the mixture was stirred for 1 hour. To the reaction mixture was added water, and the mixture was extracted with ethyl acetate. The organic layer was dried over magnesium sulfate and filtered. The filtrate was concentrated in vacuo, and to the residue was added chloroform. The precipitates were collected by filtration to give 3-amino-5-trifluoromethyl-4-methoxycarbonyl-1H-pyrazole (3.96 g) as an orange solid.

MS (APCI) m/z; 210 [M+H]$^+$ (4) The compound obtained in the above step (3) (2.37 g) was treated in the same manner as described in Reference Example A1-(2) to (3) to give 3-carboxy-6-(2-chlorophenyl)-7-(4-chlorophenyl)-2-trifluoromethylpyrazolo[1,5-a]pyrimidine (1.81 g) as a crude product (powder).

MS (APCI) m/z; 452/454 [M+H]$^+$

Reference Examples A27 to A28

The corresponding starting materials were treated in the same manner as described in Reference Example A25 or A26 to give compounds as shown in the following Table 33.

TABLE 33

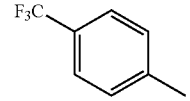

| Ref. Ex. Nos. | R$^1$ | R$^0$ | Physicochemical properties etc. |
| --- | --- | --- | --- |
| A27 | F$_3$C-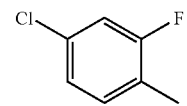 | CHF$_2$ | MS (APCI): 468/470 [M + H]$^+$ |
| A28 | Cl-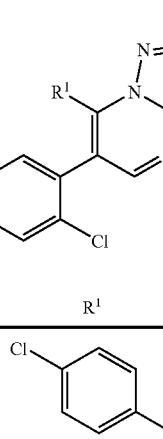-F | CF$_3$ | MS (APCI): 470/472 [M + H]$^+$ |

Reference Examples A29 to A30

The corresponding starting materials were treated in the same manner as described in Reference Example A6, and then the reaction product was treated in the same manner as described in Reference Example A1-(4) to give compounds as shown in the following Table 34.

TABLE 34

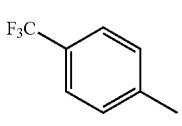

| Ref. Ex. Nos. | R$^1$ | Physicochemical properties etc. |
| --- | --- | --- |
| A29 | Cl- | MS (APCI): 399/401 [M + H]$^+$ |
| A30 | F$_3$C- | MS (APCI): 433/435 [M + H]$^+$ |

Reference Example A31

(1) To a solution of 2-[(cyano)(ethoxycarbonyl)vinyl]-1,3-dioxolane (2.0 g) in ethanol (20 mL) were added hydrazine hydrochloride (748 mg) and sodium acetate (1.34 g), and the mixture was stirred at 80° C. (external temperature) for 1 hour. After cooling to room temperature, the reaction mixture was filtered through Celite, and the filtrate was concentrated in vacuo. The resultant crude product was purified by column chromatography on silica gel (solvent: chloroform/methanol=100/0 to 85/15) to give 3-amino-4-ethoxycarbonyl-5-[2-(hydroxy)ethoxy]-1H-pyrazole (2.01 g, yield: 86%) as a pale pink solid.

MS (APCI) m/z; 216 [M+H]$^+$ (2) The compound obtained in the above step (1) (2.65 g) was treated in the same manner as described in Reference Example A1-(2) to (4) to give 3-carboxy-6-(2-chlorophenyl)-7-(4-chlorophenyl)-2-(2-hydroxyethoxy)pyrazolo[1,5-a]pyrimidine as a powder.

MS (ESI) m/z; 444/446 [M+H]$^+$

Reference Example A32

(1) To a solution of methyl 2-pyridylacetate (3.78 g) in acetic acid (15 mL) was added dropwise an aqueous solution (5 mL) of sodium nitrite (1.75 g) under ice-cooling, and the mixture was stirred at room temperature for 30 minutes. The reaction mixture was neutralized with an aqueous sodium hydrogencarbonate solution, and the mixture was extracted with ethyl acetate. The organic layer was washed with brine, dried over magnesium sulfate and filtered. The filtrate was concentrated in vacuo, and the resultant crude product was purified by column chromatography on silica gel (solvent: hexane/ethyl acetate=75/25 to 25/75) to give methyl(hydroxyimino)(2-pyridyl)acetate (3.72 g, yield: 83%) as a colorless solid.

MS (APCI) m/z; 181 [M+H]$^+$ (2) To a solution of the compound obtained in the above step (1) (1.64 g) in methanol (32 mL) was added 10% palladium-carbon (200 mg), and the mixture was shaken under hydrogen atmosphere/50 Parr for 6 hours. The reaction mixture was filtered, and the filtrate was concentrated in vacuo to give methyl(amino)(2-pyridyl)-acetate (1.52 g, yield: 93%) as an oil.

MS (APCI) m/z; 167 [M+H]$^+$ (3) To a solution of the compound obtained in the above step (2) (659 mg) in chloroform (10 mL) was added a solution of di-tert-butyl dicarbonate (908 mg) in chloroform (10 mL), and the mixture was stirred at room temperature for 1.5 hours. To the reaction mixture was added an aqueous saturated sodium hydrogencarbonate solution. The organic layer was separated and concentrated in vacuo, and the resultant crude product was purified by column chromatography on silica gel (solvent: hexane/ethyl acetate=85/15 to 60/40) to give methyl (tert-butoxycarbonylamino) (2-pyridyl)acetate (123 mg, yield: 12%) as a yellow oil.

MS (APCI) m/z; 267 [M+H]$^+$ (4) To a solution of the compound obtained in the above step (3) (122 mg) in methanol (3 mL) was added an aqueous 2N sodium hydroxide solution (460 μL), and the mixture was stirred at room temperature for 1 hour. The reaction mixture was concentrated in vacuo, and the residue and ammonium chloride (25 mg) were treated in the same manner as described in Example A5. The resultant reaction product was further treated in the same manner as described in Reference Example A7-(2) to give 2-amino-2-(2-pyridyl)acetamide (92 mg, yield: 89%) as a yellow powder.

MS (APCI) m/z; 152 [M+H]$^+$

Reference Example A33

The corresponding starting materials were treated in the same manner as described in Reference Example A23-(1) to (3), and the reaction product was further treated in the same manner as described in Reference Example A23-(5) to give 3-carboxy-6-(2-chlorophenyl)-7-(4-dimethylaminophenyl)pyrazolo[1,5-a]pyrimidine (230 mg, yield: 86%) as a solid.

MS (APCI) m/z; 393/395 [M+H]$^+$

Reference Example B1

(1) Under nitrogen atmosphere, sodium hydride (60%, 6.77 g) was added to dimethylformamide (75 mL). Thereto was added dropwise a solution of ethyl cyanoacetate (9.57 g) in dimethylformamide (15 mL) under cooling (internal temperature: ca. 10° C.) over a period of 15 minutes, and the mixture was stirred at room temperature for 10 minutes. Thereto was added dropwise a solution of carbon disulfide (5.09 mL) in dimethylformamide (12 mL) under cooling (internal temperature ≦10° C.) over a period of 20 minutes. The mixture was stirred at room temperature overnight, and thereto was added dropwise a solution of benzyl bromide (20.1 mL) in dimethylformamide (23 mL) under cooling (internal temperature ≦25° C.). The mixture was stirred at 70° C. for 7 hours and at room temperature overnight. The reaction mixture was poured in ice-water, and the mixture was stirred. The precipitates were collected by filtration and recrystallized from hot ethanol. The resultant crystals were washed with cold ethanol to give ethyl 2-cyano-3,3-bis(benzylthio)acrylate (25.63 g, yield: 82%) as a colorless solid.

MS (APCI) m/z; 370 [M+H]$^+$ (2) To a solution of the compound obtained in the above step (1) (15.0 g) in tetrahydrofuran (16 mL) and ethanol (41 mL) was added a solution of hydrazine monohydrate (2.04 g) in ethanol (18 mL) over a period of 5 minutes, and the mixture was stirred at room temperature overnight. The reaction mixture was concentrated in vacuo, and the residue was recrystallized from diisopropylether/hexane. The resultant crystals were washed with hexane/diisopropylether (4/1) to give 5-amino-3-benzylthio-4-ethoxycarbonyl-1H-pyrazole (9.45 g, yield: 84%) as a colorless solid.

MS (APCI) m/z; 278 [M+H]$^+$

Reference Example B2

The compound obtained in Reference Example B1 (8.15 g) and (2-chlorobenzyl)(4-chlorophenyl)methanone (compound obtained in Reference Example A1-(1), 9.78 g) were treated in the same manner as described in Reference Example A1-(3) to give 2-benzylthio-6-(2-chlorophenyl)-7-(4-chlorophenyl)-3-ethoxycarbonylpyrazolo[1,5-a]pyrimidine (8.24 g, yield: 51%) as a pale yellow solid.

MS (APCI) m/z; 534/536 [M+H]$^+$

Reference Example B3

To a solution of the compound obtained in Reference Example B2 (100 mg) in methylene chloride (1.5 mL) were added water (0.8 mL) and concentrated hydrochloric acid (0.05 mL) under ice-cooling (0° C.). Thereto was added 4% sodium hypochlorite solution (Antiformine, 0.4 mL), and the mixture was stirred for 2 hours. The reaction mixture was extracted with methylene chloride. The organic layer was concentrated in vacuo, and the resultant crude product was purified by column chromatography on silica gel (solvent: hexane/ethyl acetate=80/20 to 65/35) to give 6-(2-chlorophenyl)-7-(4-chlorophenyl)-2-chlorosulfonyl-3-ethoxycarbonylpyrazolo[1,5-a]pyrimidine (78 mg, yield: 82%) as a colorless solid.

MS (APCI) m/z; 510/512 [M+H]$^+$

Reference Example B4

The compound obtained in Reference Example B3 (546 mg) was treated in the same manner as described in Example B2-(1) to give 3-carboxy-6-(2-chlorophenyl)-7-(4-chlorophenyl)-2-(N,N-dimethylsulfamoyl)pyrazolo[1,5-a]pyrimidine (558 mg) as a crude product.

Reference Example B5

The compound obtained in Reference Example B4 (240 mg) was treated in the same manner as described in Example B2-(1) to give 3-carboxy-6-(2-chlorophenyl)-7-(4-chlorophenyl)-2-sulfamoylpyrazolo[1,5-a]pyrimidine (239 mg) as a crude product.

Reference Example B6

A solution of ethyl 2-cyano-3,3-bis(methylthio)-acrylate (40 g), hydrazine hydrochloride (12.6 g) and sodium acetate (22.6 g) in ethanol was stirred at 90° C. for 2 hour. After cooling to room temperature, the reaction mixture was concentrated in vacuo, and to the residue were added water and ethyl acetate. The organic layer was separated, dried over magnesium sulfate and filtered. The filtrate was concentrated in vacuo, and to the residue was added ethyl acetate and hexane. The precipitates were collected by filtration and dried to give 5-amino-4-ethoxycarbonyl-3-methylthio-1H-pyrazole (17.4 g, yield: 47%) as a colorless solid.

Reference Example B7

(1) A solution of the compound obtained in Reference Example B6 (5-amino-4-ethoxycarbonyl-3-methylthio-1H-pyrazole; 6.8 g), 1-(4-chlorophenyl)-2-(2-chlorophenyl)-3-(dimethylamino)-2-propen-1-one (10.9 g) and piperidine (578 mg) in acetic acid (13 mL) was stirred at 80° C. overnight. After cooling to room temperature, to the reaction mixture were added water and ethyl acetate. The organic layer was washed with brine, dried over magnesium sulfate and filtered. The filtrate was concentrated in vacuo, and the resultant crude product was purified by column chromatography on silica gel (solvent: hexane/ethyl acetate=85/15 to 70/30) to give 6-(2-chlorophenyl)-7-(4-chlorophenyl)-3-ethoxycarbonyl-2-methylthiopyrazolo[1,5-a]pyrimidine (5.88 g, yield: 38%) as a pale yellow solid.

(2) The compound obtained in the above step (1) (600 mg) was treated in the same manner as described in Reference Example A1-(4) to give 3-carboxy-6-(2-chlorophenyl)-7-(4-chlorophenyl)-2-methylthiopyrazolo[1,5-a]pyrimidine (502 mg) as a pale yellow powder.

MS (APCI) m/z; 430/432 [M+H]$^+$ (3) To a solution of the compound obtained in the above step (2) (1.0 g) in chloroform (20 mL) were added cyclopentylamine (260 mg), water-soluble carbodiimide hydrochloride. (620 mg) and 1-hydroxybenzotriazole (540 mg), and the mixture was stirred at room temperature overnight. To the reaction mixture were added an aqueous sodium hydrogencarbonate solution and chloroform. After stirring, the organic layer was concentrated in vacuo, and the resultant crude product was purified by column chromatography on silica gel (solvent: hexane/ethyl acetate=82/18 to 67/33) to give 6-(2-chlorophenyl)-7-(4-chlorophenyl)-3-(N-cyclopentylcarbamoyl)-2-methylthiopyrazolo[1,5-a]pyrimidine (940 mg, yield: 81%) as a pale yellow solid.

MS (APCI) m/z; 497/499 [M+H]$^+$ (4) To a solution of the compound obtained in the above step (3) (940 mg) in methylene chloride (40 mL) was added m-chloroperbenzoic acid (1.09 g) under ice-cooling, and the mixture was stirred at room temperature for 3 hours. To the reaction mixture was added an aqueous sodium thiosulfate solution. The mixture was stirred and extracted with chloroform, and the organic layer was concentrated in vacuo. The resultant crude product was purified by column chromatography on NH-silica gel (Chromatorex NH silica gel, solvent: hexane/ethyl acetate=50/50 to 0/100) to give 6-(2-chlorophenyl)-7-(4-chlorophenyl)-3-(N-cyclopentylcarbamoyl)-2-methylsulfonyl-pyrazolo[1,5-a]pyrimidine (1.0 g, yield: 100%) as a colorless solid.

MS (APCI) m/z; 529/531 [M+H]$^+$ (5) To a solution of the compound obtained in the above step (4) (1.5 g) in dimethylformamide (20 mL) was added sodium azide (1.11 g), and the mixture was stirred at 110° C. overnight. After cooling to room temperature, to the reaction mixture was added brine, and the mixture was stirred and extracted with ethyl acetate. The organic layer was washed with water and concentrated in vacuo, and the resultant crude product was purified by column chromatography on silica gel (solvent: hexane/ethyl acetate=80/20 to 30/70) to give 2-azido-6-(2-chlorophenyl)-7-(4-chlorophenyl)-3-(N-cyclopentylcarbamoyl)pyrazolo[1,5-a]pyrimidine (1.15 g) as a yellow solid. To a solution of the compound (870 mg) in tetrahydrofuran (16 mL) was added triphenylphosphine (869 mg), and the mixture was stirred at 40° C. for 1 hour. After cooling to room temperature, the reaction mixture was concentrated in vacuo, and the resultant crude product was purified by column chromatography on silica gel (solvent: chloroform/methanol=100/0 to 97/3) to give 6-(2-chlorophenyl)-7-(4-chlorophenyl)-3-(N-cyclopentylcarbamoyl)-2-triphenylphosphoranylidenaminopyrazolo[1,5-a]pyrimidine (942 mg, yield: 58%) as a yellow solid.

MS (APCI) m/z; 726/728 [M+H]$^+$ (6) To a solution of the compound obtained in the above step (5) (1.1 g) in tetrahydrofuran-water (2.8 mL/4.2 mL) was added acetic acid (7 mL), and the mixture was stirred at 100° C. for 1 hour in a microwave reactor. After cooling to room temperature, to the reaction mixture was added an aqueous 2N sodium hydroxide solution, and the mixture was extracted with chloroform. The extract was dried over magnesium sulfate and filtered. The filtrate was concentrated in vacuo, and the resultant crude product was purified by column chromatography on silica gel (solvent: hexane/ethyl acetate=80/20 to 60/40) to give 2-amino-6-(2-chlorophenyl)-7-(4-chlorophenyl)-3-(N-cyclopentylcarbamoyl)pyrazolo[1,5-a]pyrimidine (529 mg, yield: 75%) as a yellow solid.

MS (APCI) m/z; 466/468 [M+H]$^+$

Reference Example B8

(1) The corresponding starting materials were treated in the same manner as described in Reference Example B2, and the reaction product was further treated in the same manner as described in Reference Example B3 to give 6-(2-chlorophenyl)-2-chlorosulfonyl-3-ethoxycarbonyl-7-(4-trifluoromethylphenyl)pyrazolo[1,5-a]pyrimidine as a colorless powder.

MS (APCI) m/z; 544/546 [M+H]$^+$ (2) The compound obtained in the above step (1) (2.2 g) was treated in the same manner as described in Example B4, and the reaction product was further treated in the same manner as described in Example B2-(1) to give 3-carboxy-6-(2-chloro-phenyl)-7-(4-trifluoromethylphenyl)-2-sulfamoylpyrazolo[1,5-a]pyrimidine (0.45 g) as a pale yellow powder.

MS (APCI) m/z; 497/499 [M+H]$^+$

Reference Example B9

(1) The corresponding starting materials were treated in the same manner as described in Example B2-(1) to give 6-(2-bromophenyl)-3-carboxy-7-(4-chlorophenyl)-2-sulfamoylpyrazolo[1,5-a]pyrimidine (897 mg) as a pale yellow powder.

MS (APCI) m/z; 507/509 [M+H]$^+$ (2) The compound obtained in the above step (1) (150 mg) and cyclopentyl-amine (33 mg) were treated in the same manner as described in Example A1 to give 6-(2-bromophenyl)-7-(4-chlorophenyl)-3-(N-cyclopentylcarbamoyl)-2-sulfamoylpyrazolo[1,5-a]pyrimidine (170 mg, yield: 100%) as a pale yellow powder.

MS (APCI) m/z; 574/576 [M+H]$^+$ (3) The compound obtained in the above step (2) (166 mg) in dimethylformamide (2 mL) was added zinc cyanide (37 mg) and tetrakis(triphenylphosphin)palladium(0) (33 mg), and the mixture was stirred under nitrogen atmosphere at 110° C. overnight. After cooling to room temperature, to the reaction mixture were added water and ethyl acetate. The mixture was stirred, and the organic layer was separated and concentrated in vacuo. The resultant crude product was purified by column chromatography on silica gel (solvent: hexane/ethyl acetate=60/40 to 50/50) to give 7-(4-chlorophenyl)-6-(2-cyanophenyl)-3-(N-cyclopentyl-carbamoyl)-2-sulfamoylpyrazolo[1,5-a]pyrimidine (24 mg, yield: 16%) as a pale yellow powder.

MS (APCI) m/z; 521/523 [M+H]$^+$

Reference Example B10

(1) To a solution of 1-aminocyclohexanecarboxylic acid (5 g) in dioxane (70 mL) was added an aqueous sodium hydroxide solution (4.19 g in 70 mL of water), and thereto was added di-tert-butyl dicarbonate (16.7 g). The mixture was stirred at room temperature overnight. The reaction mixture was concentrated in vacuo, and to the residue were added water and ethyl acetate. The mixture was weakly acidified with an aqueous 2N hydrochloric acid solution and extracted with ethyl acetate. The combined organic layer was washed successively with water and brine, dried over magnesium sulfate and filtered. The filtrate was concentrated in vacuo, and the collected precipitates were washed with diethylether and dried in vacuo to give 1-(tert-butoxycarbonylamino)cyclohexanecarboxylic acid (5.8 g, yield: 69%) as a colorless solid.

MS (APCI) m/z; 244 [M+H]$^+$ (2) The compound obtained in the above step (1) and ammonium chloride (6.4 g) were treated in the same manner as described in Example A1 to give 1-(tert-butoxycarbonylamino)cyclohexan-1-carboxamide (5.4 g, yield: 92%) as a colorless solid.

MS (APCI) m/z; 243 [M+H]$^+$ (3) To the compound obtained in the above step (2) in dioxane (80 mL) was added a solution of 4N hydrochloric acid in dioxane (22.1 mL), and the mixture was stirred at room temperature overnight. To the reaction mixture was added diethylether, and the mixture was stirred. The precipitates were collected by filtration to give 1-aminocyclohexan-1-carboxamide (3.35 g, yield: 85%) as a colorless powder.

MS (APCI) m/z; 143 [M+H]$^+$

Reference Example B11

(1) The compound obtained in Reference Example A3-(2) (8 g) was treated in the same manner as described in Reference Example B10-(1) to give 4-(tert-butoxycarbonylamino)-tetrahydrothiopyran-4-carboxylic acid (10.8 g, yield: 69%) as a pale yellow solid.

MS (APCI) m/z; 262 [M+H]$^+$ (2) The compound obtained in the above step (1) and ammonium chloride (11.1 g) were treated in the same manner as described in Example A1 to give 4-(tert-butoxycarbonylamino)-tetrahydrothiopyran-4-carboxamide (3.3 g, yield: 30%) as a colorless solid.

MS (APCI) m/z; 261 [M+H]$^+$ (3) To a solution of the compound obtained in the above step (2) (3.3 g) in methylene chloride (100 mL) was added portionwise m-chloroperbenzoic acid (8.7 g), and the mixture was stirred at room temperature for 3 hours. The reaction mixture was extracted with chloroform, and the organic layer was washed with an aqueous saturated sodium hydrogencarbonate solution. The aqueous layer was extracted with ethyl acetate, and the combined organic layer was dried over magnesium sulfate and filtered. The filtrate was concentrated in vacuo, and the resultant crude product was purified by column chromatography on silica gel (solvent: chloroform/methanol=98/2 to 90/10) to give 4-(tert-butoxycarbonylamino)-1,1-dioxotetrahydrothiopyran-4-carboxamide (3.3 g, yield: 90%) as a colorless powder.

MS (APCI) m/z; 293 [M+H]$^+$ (4) The compound obtained in the above step (3) (3.3 g) were treated in the same manner as described in Reference Example B10-(3) to give 4-amino-1,1-dioxo-tetrahydrothiopyran-4-carboxamide (2.0 g, yield: 77%) as a colorless powder.

MS (APCI) m/z; 193 [M+H]$^+$

Reference Example B12

(1) A mixture of (R)-methioninol (4.95 g), benzonitrile (8.3 mL) and zinc bromide (250 mg) was stirred at 120° C. for 90 hours under nitrogen atmosphere. After cooling to room temperature, the reaction mixture was filtered, and the filtrate was washed with water and brine, dried over magnesium sulfate and filtered again. The filtrate was concentrated in vacuo, and the resultant crude product was purified by column chromatography on silica gel (solvent; hexane/ethyl acetate=5/1 to 3/1) to give (R)-4-(2-methylthioethyl)-2-phenyl-4,5-dihydrooxazole (3.94 g, yield: 48.6%) as a colorless oil.

MS (APCI) m/z; 222 [M+H]$^+$ (2) To a solution of the compound obtained in the above step (1) (3.94 g) in acetic acid (65 mL) was added concentrated hydrochloric acid (7.7 mL), and the mixture was refluxed under heating overnight. After cooling to room temperature, the reaction mixture was concentrated in vacuo. To the residue were added an aqueous sodium hydroxide solution (50 mL) and chloroform (100 mL), and the mixture was stirred. To the organic layer was added magnesium sulfate and silica gel, and the mixture was stirred and filtered. The filtrate was concentrated in vacuo, and the resultant crude product was washed with isopropylether and dried to give (R)—N-(tetrahydrothien-3-yl)benzamide (2.80 g, yield: 76%) as a colorless solid.

MS (APCI) m/z; 208 [M+H]$^+$ (3) To a solution of the compound obtained in the above step (2) (3.59 g) in methylene chloride (70 mL) was gradually added m-chloroperbenzoic acid (75%, 10 g) under ice-cooling, and the mixture was stirred at room temperature overnight. To the reaction mixture were added water (35 mL), sodium sulfite (3.5 g) and an aqueous saturated sodium hydrogencarbonate solution (100 mL), and the mixture was stirred for 30 minutes and extracted with chloroform. The extract was washed with an aqueous saturated sodium hydrogencarbonate solution, and the organic layer was dried over sodium sulfate and filtered. The filtrate was concentrated in vacuo, and the resultant solid materials were washed with ethyl acetate to give (R)—N-(1,1-dioxo-tetrahydrothien-3-yl)benzamide (3.5 g, yield: 85%) as a colorless solid.

MS (APCI) m/z; 240 [M+H]+

(4) To a solution of the compound obtained in the above step (3) (3.51 g) in ethanol (13 mL) was added an aqueous 6N hydrochloric acid (52 mL), and the mixture was refluxed under heating for 1 day. After cooling to room temperature, the aqueous layer was washed with ethyl acetate and concentrated in vacuo. The precipitated solid materials were washed with ethanol/diethylether, collected by filtration and further washed with diethylether to give (R)—N-(1,1-dioxo-tetrahydrothien-3-yl)amine hydrochloride (2.52 g, yield: 100%) as a colorless solid.

MS (APCI) m/z; 136 [M+H]+

Reference Example B13

(S)-Methioninol (4.83 g) was treated in the same manner as described in Reference Example B12 to give (S)—N-(1,1-dioxo-tetrahydrothien-3-yl)amine hydrochloride (3.86 g) as a colorless solid.

MS (APCI) m/z; 136 [M+H]+

Reference Example B14

To a solution of 4-amino-4-carboxy-tetrahydropyrane hydrochloride (2 g) in methanol was added dropwise a solution of 2M trimethylsilyldiazomethane-diethylether (33 mL) under ice-cooling, and the mixture was stirred at room temperature for 4 days. The reaction mixture was concentrated in vacuo, and the resultant crude product was dissolved in hexane-diethylether (1 mL/1 mL), and thereto was added an aqueous 4N hydrochloric acid. The precipitates were collected by filtration to give 4-amino-4-methoxycarbonyl-tetrahydropyrane (2.13 g, yield: 99%) as white-crystals.

MS (ESI) m/z; 160 [M+H]+

Reference Example B15

(1) Under argon atmosphere, to a solution of tetrahydro-4H-thiopyran-4-one (25.0 g) in diethylether (500 mL) was added dropwise a solution of 3M methylmagnesium bromide in diethylether at 0° C., and the mixture was stirred at the same temperature for 30 minutes. To a reaction mixture was added an aqueous saturated ammonium chloride solution (200 mL), and the mixture was extracted with ethyl acetate (×3). The organic layer was dried over magnesium sulfate and filtered. The filtrate was concentrated in vacuo, and the resultant crude product was purified by a column chromatography on silica gel (solvent; hexane/ethyl acetate=9/1 to 6/1) to give 4-methyltetrahydrothiopyran-4-ol (14.7 g, yield: 52%) as a solid.

(2) To a solution of the compound obtained in the above step (1) (13.7 g) in toluene (100 mL) were added trimethylsilyl azide (14.3 g) and boron trifluoride-diethylether complex (17.6 g), and the mixture was stirred at room temperature overnight. The reaction mixture was poured in water, and the organic layer was separated and washed successively with an aqueous saturated sodium hydrogencarbonate solution, water and brine. The organic layer was dried over magnesium sulfate and filtered. The filtrate was concentrated in vacuo, and the resultant crude product was purified by a column chromatography on silica gel (solvent; hexane/ethyl acetate=10/1) to give 4-azido-4-methyltetrahydrothiopyrane (6.84 g, yield: 42%) as an oil.

MS (APCI) m/z; 130 [M+H−N$_2$]+

(3) To a solution of the compound obtained in the above step (2) (370 mg) in diethylether (12 mL) was added lithium aluminum hydride (446 mg) at 0° C., and the mixture was stirred at room temperature. To the reaction mixture were added water (442 μL), an aqueous 15% sodium hydroxide solution (442 μL) and water (884 μL), and the mixture was stirred. The mixture was filtered through Celite to remove resultant precipitates. The filtrate was concentrated in vacuo to give 1-methyl-tetrahydrothienylamine (221 mg, yield: 72%) as an oil.

MS (APCI) m/z; 132 [M+H]+

Reference Example B16

(1) To a solution of 1,3-dibromo-2,2-dimethoxypropane (26.45 g) in dimethylsulfoxide (200 mL) was added sodium sulfide (9.46 g), and the mixture was stirred at 110 to 140° C. (external temperature) for 30 minutes. The reaction mixture was diluted with diethylether under ice-cooling, and thereto were added an aqueous saturated sodium hydrogencarbonate solution and water. The mixture was extracted with diethylether (×2), and the organic layer was washed with brine, dried over sodium sulfate and filtered. The filtrate was concentrated in vacuo, and the resultant crude product was purified by a column chromatography on silica gel (solvent; hexane/diethylether=100/0 to 15/1) to give 3,3-dimethoxythiacyclobutane (10.55 g, yield: 78%) as a yellow liquid.

MS (APCI) m/z; 103 [M+H−MeOH]+

(2) To a solution of the compound obtained in the above step (1) (9.0 g) in acetone (70 mL) was added ion-exchange resin (Amberlyst 15E, 3.5 g), and the mixture was stirred at room temperature for 21 hours. The reaction mixture was filtered through Celite, and the residue was washed with acetone. The filtrate and the washings were combined and concentrated in vacuo. The precipitates were collected by filtration and washed with cold acetone to give 3-oxothiacyclobutane (1.58 g, yield: 27%) as colorless crystals.

(3) To a solution of potassium cyanide (0.80 g) and ammonium chloride (0.62 g) in water (10 mL) were added ammonium carbonate (3.59 g) and a solution of the compound obtained in the above step (2) (1.0 g) in methanol (10 mL), and the mixture was stirred at 60° C. overnight. To the reaction mixture were added an aqueous 1N sodium hydroxide solution (5 mL) and water (50 mL), and the mixture was extracted with ethyl acetate. The organic layer was washed successively with water and brine, dried over sodium sulfate and filtered. The filtrate was concentrated in vacuo, and the resultant crude product was washed with diisopropylether to give 2-thia-5,7-diazaspiro[3,4]octan-6,8-dione (0.79 g, yield: 44%) as a powder.

MS (ESI) m/z; 157 [M−H]−

(4) A solution of the compound obtained in the above step (3) (0.75 g) in an aqueous 1N sodium hydroxide solution (10 mL) was refluxed under heating for 15 hours. After cooling to room temperature, to the reaction mixture was added concentrated hydrochloric acid (3 mL), and the mixture was concentrated in vacuo to give 3-aminothietan-3-carboxylic acid (1.54 g) as a solid.

MS (APCI) m/z; 134 [M+H]+

(5) To a suspension of the compound obtained in the above step (4) (1.54 g) in methanol (20 mL) was added thionyl chloride (0.50 mL) under ice-cooling, and the mixture was refluxed under heating for 5 hours. The reaction mixture was neutralized with ice-water and an aqueous sodium hydrogencarbonate solution, and the mixture was extracted with chloroform. The organic layer was dried over sodium sulfate and filtered. The filtrate was concentrated in vacuo. To the residue was added a solution of 4N hydrochloric acid in ethyl acetate (2 mL), and the precipitates were collected by filtration and washed successively with diisopropylether and ethyl acetate to give methyl 3-aminothietan-3-carboxylate (0.53 g, yield: 61%) as a powder.

MS (APCI) m/z; 148 [M+H]$^+$

Reference Example B17

(1) To a solution of 6-(2-chlorophenyl)-3-ethoxycarbonyl-7-(4-trifluoro-methylphenyl)-2-methylpyrazolo[1,5-a]pyrimidine (corresponding ethyl ester of the compound obtained in Reference Example A12; 5.35 g) in carbon tetrachloride (73 mL) were added N-bromosuccinimide (6.21 g) and 2,2'-azobisisobutylonitrile (96 mg), and the mixture was stirred at 85° C. (external temperature) for 18 hours. After cooling to room temperature, the reaction mixture was filtered through Celite, and the filtrate was concentrated in vacuo. The resultant crude product was purified by a column chromatography on silica gel (solvent; hexane/ethyl acetate=80/20 to 65/35) to give 2-bromomethyl-6-(2-chlorophenyl)-3-ethoxycarbonyl-7-(4-trifluoromethylphenyl)-pyrazolo[1,5-a]pyrimidine (4.72 g, yield: 75%) as a pale yellow solid.

MS (APCI) m/z; 538/540 [M+H]$^+$ (2) To a solution of the compound obtained in the above step (1) (4.72 g) in dimethylformamide (50 mL) was added potassium acetate (2.58 g), and the mixture was at 60° C. for 1.5 hours. After cooling to room temperature, the reaction mixture was diluted with ethyl acetate, and to the residue was added water. The organic layer was separated and washed successively with water and brine, dried over magnesium sulfate and filtered. The filtrate was concentrated in vacuo, and the resultant crude product was purified by a column chromatography on silica gel (solvent; hexane/ethyl acetate=80/20 to 60/40) to give 2-acetoxymethyl-6-(2-chlorophenyl)-3-ethoxycarbonyl-7-(4-trifluoromethylphenyl)pyrazolo[1,5-a]pyrimidine (1.86 g, yield: 41%) as a colorless powder.

MS (APCI) m/z; 518/520 [M+H]$^+$ (3) To a solution of the compound obtained in the above step (2) (1.86 g) in ethanol-tetrahydrofuran (30 mL/30 mL) was added a solution of 21% sodium ethoxide in ethanol (2.5 mL), and the mixture was stirred at 60° C. for 30 minutes. After cooling to room temperature, the reaction mixture was diluted with ethyl acetate, and thereto was added an aqueous diluted hydrochloric acid solution. The organic layer was separated and washed with brine, dried over magnesium sulfate and filtered. The filtrate was concentrated in vacuo, and the resultant crude product was purified by a column chromatography on silica gel (solvent; hexane/ethyl acetate=85/15 to 55/45) to give 6-(2-chlorophenyl)-3-ethoxycarbonyl-7-(4-trifluoromethylphenyl)-2-hydroxymethyl-pyrazolo[1,5-a]pyrimidine (1.05 g, yield: 62%) as a colorless solid.

MS (APCI) m/z; 476/478 [M+H]$^+$ (4) The compound obtained in the above step (3) (1.03 g) was treated in the same manner as described in Reference Example A1-(4) to give 3-carboxy-6-(2-chlorophenyl)-7-(4-trifluoromethylphenyl)-2-hydroxymethylpyrazolo[1,5-a]pyrimidine (894 mg, yield: 92%) as a pale yellow solid.

MS (APCI) m/z; 448/450 [M+H]$^+$

Reference Examples B18 to B20

The compound obtained in Reference Example B17-(3) was treated in the same manner as described in Example B33, the reaction product and the corresponding amine were treated in the same manner as described in Example A5, and then the reaction product was treated in the same manner as described in Reference Example A1-(4) to give the compounds as shown in the following Table 35.

TABLE 35

| Ref. Ex. Nos. | R$^t$ | Physicochemical properties etc. |
|---|---|---|
| B18 | NH$_2$ | powder |
| B19 | —NHCH$_3$ | powder |
| B20 | —N(CH$_3$)$_2$ | powder |

Reference Example B21

To a solution of the compound obtained in Reference Example A30 (1.00 g) and triethylamine (1.33 mL) in methylene chloride (20 mL) was added triphosgene (350 mg) under ice-cooling, and the mixture was stirred at room temperature for 1.5 hours. To the reaction mixture was added a solution of 0.5M ammonia in dioxane (20 mL), and the mixture was stirred at room temperature for 30 minutes. To the reaction mixture was added water, and the mixture was extracted with chloroform. The organic layer was dried over magnesium sulfate and filtered. The filtrate was concentrated in vacuo, and the resultant crude product was purified by a column chromatography on silica gel (solvent; hexane/ethyl acetate=65/35 to 20/80) to give 3-ethoxycarbonyl-6-(2-chlorophenyl)-7-(4-trifluoromethylphenyl)-2-ureidopyrazolo[1,5-a]pyrimidine (0.70 g, yield: 64%) as a colorless powder.

MS (APCI) m/z; 504/506 [M+H]$^+$

Reference Example B22

(1) To a solution of the compound obtained in Reference Example B16-(2) (100 mg) in ethanol (3 mL) were added hydroxylamine hydrochloride (236 mg) and sodium carbonate (360 mg), and the mixture was refluxed under heating for 17 hours. After cooling to room temperature, to the reaction mixture were added an aqueous saturated sodium hydrogencarbonate solution and water, and the mixture was extracted with chloroform. The organic layer was concentrated in vacuo, and the resultant crude product was purified by a column chromatography on silica gel (solvent; hexane/ethyl acetate=90/10 to 50/50) to give 3-hydroxyiminothiacyclobutane (93 mg, yield: 80%) as a colorless solid.

(2) Under nitrogen atmosphere, to a solution of lithium-aluminum hydride (58 mg) in tetrahydrofuran (2 mL) was added dropwise a solution of the compound obtained in the above step (1) (93 mg) in tetrahydrofuran (1.5 mL) under ice-cooling, and the mixture was stirred at room temperature for 1 hour. To the reaction mixture were added successively water (60 µL), an aqueous 15% sodium hydroxide solution (60 µL) and water (120 µL) under ice-cooling, and the mixture was stirred at room temperature. The reaction mixture was filtered through Celite and the filtrate was concentrated in vacuo to give 3-aminothiacyclobutane as a crude product.

Reference Example B23

(1) The compound obtained in Reference Example B1 was treated in the same manner as described in Reference Example A14B, and then the reaction product was treated in the same manner as described in Reference Example A14-(3) to give 2-benzylthio-7-chloro-6-(2-chlorophenyl)-3-ethoxy-carbonylpyrazolo[1,5-a]pyrimidine as a powder.

MS (APCI) m/z; 458/460 [M+H]$^+$ (2) A solution of the compound obtained in the above step (1) (1.0 g), [1,1'-bis(diphenylphosphino)ferrocene]-palladium(II) dichloride-methylene chloride complex (63 mg), potassium phosphate (1.4 g) and 4-fluorophenylboronic acid (339 mg) in 1,4-dioxane (25 mL) was stirred at 80° C. for 16 hours. After cooling to room temperature, to the reaction mixture was added water, and the mixture was extracted with ethyl acetate. The organic layer was washed with brine, dried over magnesium sulfate and filtered. The filtrate was concentrated in vacuo, and the resultant crude product was purified by a column chromatography on silica gel (solvent; hexane/ethyl acetate=2/1 to 1/1) to give 2-benzylthio-6-(2-chlorophenyl)-3-ethoxycarbonyl-7-(4-fluorophenyl)pyrazolo[1,5-a]pyrimidine (865 mg, yield: 76%) as a powder.

MS (APCI) m/z; 518/520 [M+H]$^+$ (3) The compound obtained in the above step (2) (854 mg) was treated in the same manner as described in Reference Example B3, and then the reaction product was treated in the same manner as described in Example B4 to give 6-(2-chlorophenyl)-3-ethoxycarbonyl-7-(4-fluorophenyl)-2-sulfamoylpyrazolo[1,5-a]pyrimidine (670 mg, yield: 78%) as a powder.

MS (APCI) m/z; 475/477 [M+H]$^+$ (4) The compound obtained in the above step (3) (660 mg) was treated in the same manner as described in Example B2-(1) to give 3-carboxy-6-(2-chlorophenyl)-7-(4-fluorophenyl)-2-sulfamoylpyrazolo[1,5-a]pyrimidine (318 mg, yield: 56%) as a powder.

MS (APCI) m/z; 447/449 [M+H]$^+$

Reference Examples B24 to B28

1) Reference Examples B24 to B25: The corresponding staring materials were treated successively in the same manner as described in Reference Example B1 to B3, Example B4 and Example B2-(1) to give the compounds as shown in the following Table 36.

2) Reference Examples B26 to B27: The corresponding staring materials were treated in the same manner as described in Reference Example B23 to give the compounds as shown in the following Table 36.

3) Reference Examples B28: The corresponding staring materials were treated successively in the same manner as described in Reference Example B23-(1) and Reference Example A14-(4) to (5) to give the compounds as shown in the following Table 36.

TABLE 36

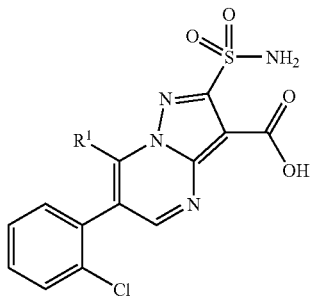

| Ref. Ex. Nos. | $R^1$ | Physicochemical properties etc. |
|---|---|---|
| B24 | Cl, F substituted benzyl | powder |
| B25 | $F_2HC$ substituted benzyl | powder |
| B26 | Me substituted benzyl | powder |
| B27 | MeO substituted benzyl | powder |
| B28 | piperidinylmethyl | powder |

Experiment 1
[Human CB1 Receptor Binding Assay]

(1) Preparation of Human CB1 Receptor (Membrane Fraction):

Materials)

Human CB1-expressing cell line: hCB1/CHO (#ES-110-C, Euroscreen)

Medium: F-12 (GIBCO #11765-062), 10% fetal calf serum, 400 μg/mL of Geneticin (GIBCO #11811-031), 100 units/mL of Penicillin, 100 μg/mL of Streptomycin (GIBCO #15140-122)

Buffer A: 50 mM tris-HCl (pH 7.5) containing ethylenediaminetetraacetic acid (2.5 mM), $MgCl_2$ (5 mM) and sucrose (200 mM)

Method) The receptor-expressing cells cultivated in the above medium were washed with phosphate buffer (×2 times) and thereto was added Buffer A (2 mL) under ice-cooling or 4° C. (the following procedures were also carried out at the same temperature). The cells were collected by using a cell-scraper, treated by a microtip-type ultrasonicator for 20 seconds (pulse-on: 2 sec, pulse-off: 1 sec) and centrifuged (500× g, 15 min). The supernatant was separated and centrifuged (43000×g, 60 min). The resultant pellet was suspended in Buffer A and homogenized with a potter-type homogenizer. To the homogenate was added an equal volume of 80% glycerol and stored at −80° C.

(2) Procedure of CB1 Receptor Binding Assay:
Materials)

Buffer B: 50 mm tris-HCl (pH 7.5) containing ethylenediaminetetraacetic acid (2.5 mM), $MgCl_2$ (5 mM) and bovine serum albumine (2 mg/mL, fatty acid-free, SIGMA-A7030)

Buffer C: 50 mM tris-HCl (pH 7.5) containing ethylenediaminetetraacetic acid (2.5 mM), $MgCl_2$ (5 mM) and bovine serum albumine (2 mg/mL, SIGMA-A7906)

Coating solution: 0.3% ethyleneimine polymer

Radioligand: [$^3$H]-CP55940 (30 nM, 7992 dpm/µL, PerkinElmer, #NET-1051) prepared by diluting 8.3 µM solution of the radioligand with Buffer B Method) Each well of the assay plate (96-well, Corning Costar Code #3371) was filled with Buffer B (140 µL), a solution of each test compound in dimethylsulfoxide (20 µL, final concentration: 0.1%), radioligand (20 µL) and membrane preparation (20 µL, 0.5 to 8.0 µg/20 µL) and the mixture was incubated at room temperature for 90 minutes to proceed the binding reaction. The reaction mixture was filtered through Unifilter GF/B (Packard #6005177) presoaked with the above coating solution to collect the membrane fraction. The plate was washed with Buffer C (200 µL×10 times) and dried at 50° C. for 1 hour and Microscinti 40 (40 µL/well) was added to each well. The bound radiolabel was quantitated by a scintillation counter (Top Count NXT, Packard). $IC_{50}$ value of each test compound against the radioligand-binding to CB1 receptors was calculated on the basis of the quantitated radiolabel activity by using Microsoft Excel 2000 (Microsoft).

(3) Results:

$IC_{50}$ value of each test compound is shown in the following Table 37. Meanwhile, the symbols (++ and +++) are defined as follows:

++: 10 nM<$IC_{50}$<100 nM

+++: 10 nM<$IC_{50}$

TABLE 37

| Test Compound (Example No.) | CB1 receptor-binding activity ($IC_{50}$) |
|---|---|
| Example A5 | ++ |
| Example A10 | ++ |
| Example A13 | ++ |
| Example A15 | ++ |
| Example B6 | ++ |
| Example B12 | ++ |
| Example B14 | +++ |
| Example B15 | +++ |
| Example B23 | +++ |
| Example B26 | ++ |
| Example B30 | ++ |

Experiment 2
[Selectivity of the Test Compound to Human CB1 Receptors]
(1) Materials and Methods
a) Human CB1 receptor-binding assay: The binding assay was conducted in the same manner as described in Experiment 1.
b) Human CB2 receptor-binding assay: The binding assay was conducted in the same manner as described in Experiment 1, except that human CB2-expressing CHO cell line (hCB2/CHO) was used instead of hCB1 cell line. $IC_{50}$ value of each test compound against the radioligand-binding to CB2 receptors was calculated in the manner as described in Experiment 1. Besides, selectivity to CB1 receptors was evaluated in terms of the ratio of $IC_{50}$ value for CB2/$IC_{50}$ value for CB1.

(2) Results: The selectivity of each test compound is shown in the following Table 38. Meanwhile, the symbols (++ and +++) in the Table are the same as defined in Experiment 1.

TABLE 38

| Test Compound (Example No.) | CB1 receptor-binding activity ($IC_{50}$) | Selectivity |
|---|---|---|
| Example A3 | ++ | >500 |
| Example A140 | +++ | |
| Example A146 | ++ | |
| Example A175 | ++ | |
| Example B32 | +++ | |
| Example B36 | +++ | |
| Example B62 | ++ | |
| Example B74 | +++ | |
| Example B84 | ++ | |

INDUSTRIAL APPLICABILITY

The compounds [I] of the present invention are useful for treatment and/or prophylaxis of various CB1 receptor-mediated diseases such as psychosis including schizophrenia.

The compounds [I] of the present invention are also useful for withdrawal from a chronic treatment, alcohol dependence or drug abuse. Furthermore, the compounds [I] of the present invention are useful as an agent for enhancing analgesic activity or an agent for smoking cessation.

The invention claimed is:
1. A compound of the formula [I-I]:

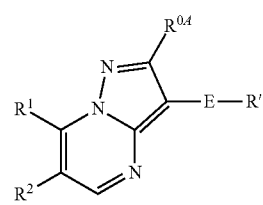

[I-I]

wherein
$R^1$ and $R^2$ are the same or different and each is a phenyl group optionally substituted by one to three substituents selected from the group consisting of halogen atoms, cyano groups, alkyl groups optionally substituted by 1 to 3 halogen atoms, and amino groups optionally substituted by 1 or 2 alkyl groups,
$R^{0.4}$ is (a) a hydrogen atom, (b) an alkyl group optionally substituted by 1 to 3 halogen atoms, (c) an alkyloxy group optionally substituted by a hydroxyl group, (d) a hydroxyalkyl group, (e) an amino group substituted by 1 to 2 groups selected from the group consisting of alkyl groups, alkyl carbonyl groups, and alkylsulfonyl groups, or (f) a 4- to 6-membered nitrogen-containing aliphatic heterocyclic group,
E is a group of the formula: —C(=O)— or —$SO_2$—,
R' is a group of the following formula [i], [ii] or [iii]:

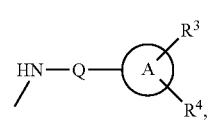

[i]

115

-continued

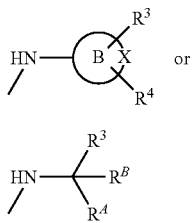

in which Ring A is (a) a $C_{3-8}$ cycloalkyl group optionally fused to a benzene ring or (b) a benzene ring, Q is a single bond or a methylene group, and Ring B is a 4- to 7-membered aliphatic heterocyclic group, said cyclic group binding via its ring-carbon atom to the adjacent nitrogen atom, A1) provided that if R' is a group of the formula [i], then $R^3$ is (a) an alkyl group optionally substituted by a member of the group consisting of hydroxyl groups and amino groups, (b) a cyano group, (c) a carboxyl group, (d) an alkyloxycarbonyl group, (e) —CON($R^e$)($R^f$) wherein $R^e$ and $R^f$ are the same or different and each is a hydrogen atom, an alkyl group, or a dialkylaminoalkyl group, or (f) an acylamino group, and $R^4$ is hydrogen atom or an acylamino group; A2) provided that if R' is a group of the formula [ii], then X is sulfur atom, a group of the formula: —$SO_2$—, an oxygen atom, or a group of the formula: —$NR^k$— in which $R^k$ is an alkyloxycarbonyl group, an alkylsulfonyl group, an alkylcarbonyl group, or a dialkylaminosulfonyl group, $R^3$ is (a) an alkyl group optionally substituted by hydroxyl group, (b) carboxyl group, (c) an alkyloxycarbonyl group, or (d) a group of the formula: —CON($R^e$)($R^f$) in which $R^e$ and $R^f$ are the same or different and each is a hydrogen atom, an alkyl group, or a trihalogenoalkyl group, and $R^4$ is hydrogen atom; or A3) provided that if R' is a group of the formula [iii], then $R^4$ is (a) an alkyl group optionally substituted by a hydroxyl group, (b) a phenyl group optionally substituted by a halogen atom or a trihalogenoalkyl group, or (c) a 5- to 6-membered nitrogen-containing heteroaryl group, $R^B$ is hydrogen atom or an alkyl group, $R^3$ is an alkyl group, a carboxyl group, or a group of the formula: —CON($R^a$)($R^b$) in which $R^a$ and $R^b$ are the same or different and each is a hydrogen atom or an alkyl group, excluding 6-phenyl-7-(4-chlorophenyl)-3-(N-isopropylcarbamoyl) pyrazolo[1,5-a]pyrimidine;

6-(2-chlorophenyl)-7-(4-chlorophenyl)-3-(N-isopropylcarbamoyl)-pyrazolo[1,5-a]pyrimidine;

6-(2-chlorophenyl)-7-(4-chlorophenyl)-3-[N-(α-dimethylbenzy)carbamoyl]pyrazolo[1,5-a]pyrimidine;

6-(2-chlorophenyl)-7-(4-chlorophenyl)-3[N-(α-methylbenzyl)carbamoyl]pyrazolo[1,5-a]pyrimidine;

6-(2-chlorophenyl)-7-(4-chlorophenyl)-3-[N-[1-(2-pyridyl)ethyl]-carbamoyl]pyrazolo[1,5-a]pyrimidine;

6-(2-chlorophenyl)-7-(4-trifluoromethylphenyl)-3-[N-[1-(2-pyridyl)ethyl]carbamoyl]pyrazolo-[1,5-a]pyrimidine; and 6-(2-chlorophenyl)-7-(4-chlorophenyl)-3-[N-(4-cyanobenzyl)carbamoyl]pyrazolo[1,5-a]pyrimidine, or a pharmaceutically acceptable salt thereof.

116

2. A compound of the formula [I-II]:

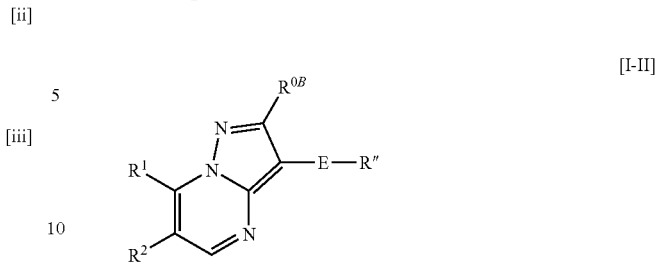

wherein $R^1$ and $R^2$ are the same or different and each is a phenyl group optionally substituted by 1 to 2 substituents selected from the group consisting of halogen atoms, cyano groups, alkyl groups, dihalogenoalkyl groups, and trihalogenoalkyl groups, $R^{OB}$ is a group of the formula: —$SO_2N(R^{O1})(R^{O2})$; a group of the formula: —$NHCONHR^{O3}$; a group of the formula: —CON($R^e$)($R^f$); carboxyl group; or a hydroxyalkyl group, $R^{O1}$ and $R^2$ are the same or different and each hydrogen atom, an alkyl group or a carbamoylalkyl group, $R^{O3}$ is hydrogen atom or an alkyl group, $R^e$ and $R^f$ are the same or different and each is a hydrogen atom, an alkyl group or a dialkylamino group, E is a group of the formula: —C(=O)— or —$SO_2$—, R" is a group of the formula: —N($R^5$)($R^6$), $R^5$ is a hydrogen atom or an alkyl group, and $R^6$ is (a) an alkyl group optionally substituted by 1 to 3 substituents selected from the group consisting of halogen atoms, hydroxyl groups, cyano groups, alkyloxy groups, $C_{3-8}$ cycloalkyl groups, hydroxy-$C_{3-8}$ cycloalkyl groups, amino-$C_{3-8}$ cycloalkyl groups, $C_{3-8}$ cycloalkyl groups substituted by 1 or 2 halogen atoms, dialkylamino groups, carboxyl groups, carbamoyl groups optionally substituted by 1 or 2 alkyl groups, a phenyl group optionally substituted by 1 or 2 halogen atoms, trihalogenoalkyl-phenyl groups, alkyloxyphenyl groups, carboxyphenyl groups, and a saturated or unsaturated 5- to 6-membered nitrogen- or oxygen-containing heterocyclic group, (b) a $C_{3-8}$ cycloalkyl group, said cycloalkyl group being optionally fused to a benzene ring and optionally substituted by 1 to 2 groups selected from cyano groups, alkyl groups, hydroxyalkyl groups, carboxyalkyl groups, aminoalkyl groups, alkylcarbonylamino-alkyl groups, dialkylcarbamoylamino-alkyl groups, alkylsulfonylamino-alkyl groups, dialkylsulfamoylamino-alkyl groups, carboxyl groups, alkyloxycarbonyl groups, phenylalkyloxycarbonyl groups, a group of the formula: —CON($R^{a1}$)($R^{b1}$) in which $R^{a1}$ and $R^{b1}$ are the same or different and each is a hydrogen atom, an alkyl group, or a dialkylamino-alkyl group, and a tetrazolyl group, (c) a saturated or unsaturated 4- to 6-membered nitrogen-, sulfur- or oxygen-containing heterocyclic group optionally substituted by 1 to 3 groups selected from oxo groups, hydroxy groups, cyano groups, alkyl groups, hydroxyalkyl groups, carboxyl groups, alkyloxycarbonyl groups, alkylsulfonyl groups, a group of the formula: —CON($R^{a2}$)($R^{b2}$) in which $R^{a2}$ and $R^{b2}$ are the same or different and each is a hydrogen atom, an alkyl group, a trihalogenoalkyl group, a cyanoalkyl group, a hydroxyalkyl group, an alkyloxyalkyl group, an alkylsulfonyl group, or a $C_{3-8}$ cycloalkyl group, a pyrrolidinylcarbonyl group, and a morpholinocarbonyl group, or (d) an amino group optionally substituted by 1 to 2 groups selected from the group consisting of an alkyl group and a pyridyl group, excluding
6-(2-chlorophenyl)-7-(4-chlorophenyl)-3-[N-(1,1-dioxotetrahydrothien-3-yl)carbamoyl]-2-(hydroxymethyl) pyrazolo[1,5-a]pyrimidine,
or a pharmaceutically acceptable salt thereof.

3. A compound of the formula [I-I-a]:

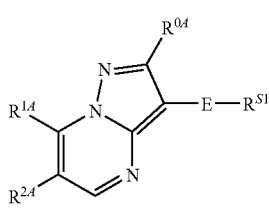

[I-I-a]

wherein
R$^{1A}$ is a phenyl group optionally substituted by one to two group(s) selected from a halogen atom, a difluoroalkyl group, a trifluoroalkyl group and a dialkylamino group,
R$_{2A}$ is a phenyl group optionally substituted by one to two group(s) selected from a halogen atom and cyano group,
R$^{0A}$ is (a) a hydrogen atom, (b) an alkyl group optionally substituted by 1 to 3 halogen atoms, (c) an alkyloxy group optionally substituted by a hydroxyl group, (d) a hydroxyalkyl group, (e) an amino group substituted by 1 to 2 groups selected from the group consisting of alkyl groups, alkylcarbonyl groups, and alkylsulfonyl groups, or (f) a 4- to 6-membered nitrogen-containing aliphatic heterocyclic group,
E is a group of the formula: —C(=O)— or —SO$_2$—,
R$^{S1}$ is a group of the following formula [i-b], [i-c], [i-d], [ii-b], [iii-b] or [iii-c]:

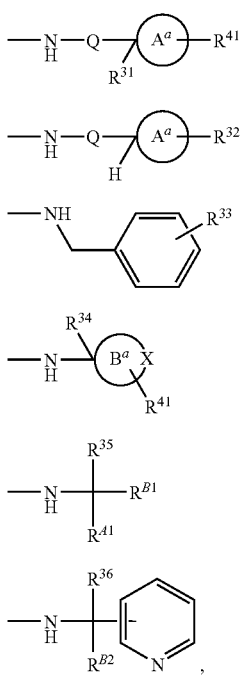

Ring A$^a$ is (a) a C$_{3-8}$ cycloalkyl group or (b) a C$_{5-6}$ cycloalkyl fused to a benzene ring, Q is a single bond or methylene group,
Ring B$^a$ is a 4- to 7-membered aliphatic heteromonocyclic group binding via its ring carbon atom to the adjacent nitrogen atom, X is sulfur atom, —SO—, —SO$_2$—, oxygen atom or a group of the formula: —NR$^k$—, R$^k$ is an alkyl group, an alkylcarbonyl group, an alkyloxycarbonyl group, an alkylsulfonyl group, aminosulfonyl group optionally substituted by one or two alkyl group(s) or a carbamoyl group optionally substituted by one or two alkyl group(s),
R$^{31}$ is (a) cyano group, (b) an alkyl group, (c) a hydroxyalkyl group, (d) an aminoalkyl group optionally substituted by, at the amino moiety, an alkylcarbonyl group, dialkylsulfamoyl group, an alkylsulfonyl group or a dialkylcarbamoyl group, (e) a carboxyalkyl group, (f) carboxyl group, (g) an alkyloxycarbonyl group, (h) a carbamoyl group optionally substituted by one to two group(s) selected from an alkyl group and a dialkylaminoalkyl group, (i) or a group of the following formula:

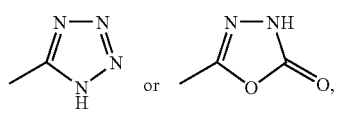

R$^{41}$ is hydrogen atom, amino group or a group of the formula: R$^{xa}$CONH—, R$^{xa}$ is (a) hydrogen atom, (b) an alkyl group optionally substituted by one to three group(s) selected from a halogen atom, cyano group, an alkylsulfonyl group and a pyridyl group, (c) an alkyloxy group optionally substituted by a 6- to 10-membered monocyclic or bicyclic aryl group, (d) a cycloalkyl group, (e) a 6- to 10-membered monocyclic or bicyclic aryl group optionally substituted by one to two group(s) selected from a halogen atom, cyano group, an alkyl group, a trihalogenoalkyl group and an alkyloxy group, (f) an amino group optionally substituted by one or two alkyl group(s) or (g) a saturated or unsaturated 4- to 7-membered nitrogen-containing heteromonocyclic group optionally substituted by one to two group(s) selected from a halogen atom, cyano group, an alkyl group and a trihalogenoalkyl group,
R$^{32}$ is hydroxyl group, carboxyl group, an alkyloxycarbonyl group, amino group or a group of the formula: R$^{xa}$-CONH—,
R$^{33}$ is carboxyl group or an alkyloxycarbonyl group,
R$^{34}$ is (a) cyano group, (b) an alkyl group, (c) a hydroxyalkyl group, (d) an aminoalkyl group, (e) a carboxyalkyl group, (f) carboxyl group, (g) an alkyloxycarbonyl group, (h) a carbamoyl group optionally substituted by one to two group(s) selected from an alkyl group, a hydroxyalkyl group, a cyanoalkyl group, a trihalogenoalkyl group, an alkyloxyalkyl group, a cycloalkyl group, an alkylsulfonyl group and a dialkylamino-alkyl group, (i) a group of the formula:

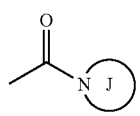

or (j) a group of the following formula:

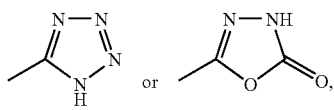

Ring J is a saturated or unsaturated nitrogen-containing 4- to 7-membered heteromonocyclic group optionally containing oxygen atom(s) as a heteroatom(s) other than the nitrogen atom, $R^{35}$ is a hydroxyalkyl group, carboxyl group, an alkyloxycarbonyl group or a carbamoyl group optionally substituted by one or two alkyl group(s), $R^{41}$ is an alkyl group, a cycloalkyl group, a phenyl group optionally substituted by one or two group(s) selected from a halogen atom, an alkyloxy group and a trihalogenoalkyl group or benzyl group, $R^{B1}$ is hydrogen atom or an alkyl group, $R^{36}$ is an alkyl group or carbamoyl group, $R^{B2}$ is hydrogen atom or an alkyl group, excluding 6-(2-chlorophenyl)-7-(4-chlorophenyl)-3-[N-(4-cyano-4-tetrahydro-thiopyranyl)carbamoyl]pyrazolo[1,5-a]pyrimidine;

6-(2-chlorophenyl)-7-4-chloro-phenyl)-3-[N-[1-(2-pyridyl)ethyl]carbamoyl]pyrazolo[1,5-a]pyrimidine; and 6-(2-chlorophenyl)-7-(4-trifluoromethylphenyl)-3-[N-[1-(2-pyridyl)ethyl]carbamoyl]-pyrazolo[1,5-a]pyrimidine, or a pharmaceutically acceptable salt thereof.

4. A compound of the formula [I-II-i]:

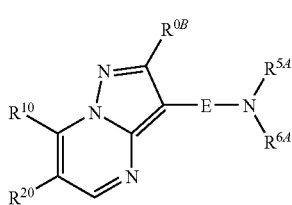

wherein $R^{10}$ and $R^{20}$ are the same or different and each is a phenyl group optionally substituted by one to three group(s) selected from a halogen atom, cyano group, an alkyl group optionally substituted by one to three halogen atom(s), an alkyloxy group optionally substituted by one to three halogen atom(s), an amino group optionally substituted by one to two alkyl group(s), an alkylthio group, an alkylsulfinyl group and an alkylsulfonyl group, $R^{OB}$ is a group of the formula: —$SO_2N(R^{O1})(R^{O2})$, a group of the formula: —$NHCONHR^{O3}$, a group of the formula: —$CON(R^e)(R^f)$, carboxyl group or a hydroxyalkyl group, $R^{O1}$ and $R^{O2}$ are the same or different and each hydrogen atom, an alkyl group or a carbamoylalkyl group, $R^{O3}$ is hydrogen atom or an alkyl group, $R^e$ and $R^f$ are the same or different and each hydrogen atom, an alkyl group or a dialkylamino group, E is a group of the formula: —C(=O)— or —$SO_2$—, $R^{5A}$ is hydrogen atom or an alkyl group, and $R^{6A}$ is (A) an alkyl group optionally substituted by one to three group(s) selected from (a) a halogen atom, (b) hydroxyl group, (c) cyano group, (d) an alkyloxy group, (e) carboxyl group, (f) a carbamoyl group optionally substituted by one or two alkyl group(s), (g) an alkylthio group, (h) an alkylsulfonyl group, (i) a cycloalkyl group optionally substituted by one to two group(s) selected from an alkyl group and hydroxyl group, (j) an amino group optionally substituted by one or two alkyl group(s) and (k) a saturated or unsaturated 4- to 10-membered monocyclic or bicyclic nitrogen-, sulfur- or oxygen-containing heterocyclic group; or (B) a cycloalkyl group optionally fused to a benzene ring and optionally substituted by one to two group(s) selected from (a) an alkyl group optionally substituted by hydroxyl group, carboxyl group and amino group; (b) cyano group; (c) carboxyl group; (d) a group of the formula: $R^{xa}CO$—; (e) a group of the formula: —$N(R^{a1})(R^{b1})$; (f) a group of the formula: —$CON(R^{a1})(R^{b1})$; (g) a 6- to 10-membered monocyclic or bicyclic aryl group; (h) an alkyl group substituted by a 6- to 10-membered monocyclic or bicyclic aryl group; and (i) a saturated or unsaturated 4- to 7-membered nitrogen-containing heteromonocyclic group optionally substituted by one or two oxo group(s), $R^{a1}$ and $R^{b1}$ are the same or different and each hydrogen atom, hydroxyl group, cyano group, an alkyl group, a group of the formula: $R^{xa}CO$—, an alkylsulfonyl group, an aminoalkyl group, a monoalkylamino-alkyl group or a dialkylamino-alkyl group; or (C) a 6- to 10-membered monocyclic or bicyclic aryl group optionally substituted by one to two group(s) selected from cyano group, a trihalogenoalkyl group, an alkyloxy group and carboxyl group; or (D) a saturated or unsaturated 4- to 10-membered nitrogen-containing monocyclic or bicyclic heterocyclic group containing at least one heteroatom selected from sulfur atom, oxygen atom and nitrogen atom and optionally substituted by one to four group(s) selected from (a) a halogen atom, (b) hydroxyl group, (c) oxo group, (d) cyano group, (e) an alkyl group, (f) a trihalogenoalkyl group, (g) a hydroxyalkyl group, (h) an alkyloxyalkyl group, (i) an alkyloxy group, (j) a group of the formula: $R^{xa}CO$—, (k) a cycloalkyl group, (l) an alkylsulfonyl group, (m) an aminosulfonyl group optionally substituted by one or two alkyl group(s), (n) phenylsulfonyl group, (o) amino group, (p) a group of the formula: $R^{xa}CONH$—, (q) a carbamoyl group optionally substituted by one or two alkyl group(s), (r) a 6- to 10-membered monocyclic or bicyclic aryl group optionally substituted by a halogen atom(s), and (s) a saturated or unsaturated 4- to 7-membered sulfur-, oxygen- or nitrogen-containing heteromonocyclic group optionally substituted by one to two group(s) selected from an alkyl group and a trihalogenoalkyl group; or (E) a group of the formula: —$N(R^{81})(R^{91})$, $R^{81}$ is hydrogen atom or an alkyl group, $R^{91}$ is (a) an alkyl group optionally substituted by one to three group(s) selected from a halogen atom, cyano group and a 6- to 10-membered monocyclic or bicyclic aryl group; (b) a cycloalkyl group; (c) a 6- to 10-membered monocyclic or bicyclic aryl group optionally substituted by a group selected from a halogen atom, cyano group, an alkyl group, a trihalogenoalkyl group, an alkyloxy group, a trihalogenoalkyloxy group, an alkylthio group, an alkylsulfonyl group and a group of the formula: $R^{xa}CO$—; (d) a group of the formula: $R^{xa}CO$—; or (e) a saturated or unsaturated 4- to 7-membered sulfur-, oxygen- or nitrogen-containing heteromonocyclic group optionally substituted by a group selected from a halogen atom, an alkyl group, a trihalogenoalkyl group and an alkyloxy group; or
(F) both $R^{5A}$ and $R^{6A}$ combine each other together with the adjacent nitrogen atom to form a saturated or unsaturated 4- to 10-membered nitrogen-containing monocyclic or bicyclic heterocyclic group optionally containing one or two heteroatom(s) other than the nitrogen atom selected from sulfur atom and oxygen atom and optionally substituted by one or two group(s) selected from a halogen atom, oxo group, an alkyl group, a group of the formula: $R^{xa}CO$—and a dialkylaminosulfonyl group,
$R^{xa}$ is (a) hydrogen atom, (b) an alkyl group optionally substituted by one to three group(s) selected from a halogen atom, cyano group, an alkylsulfonyl group and a pyridyl group, (c) an alkyloxy group optionally substituted by a 6- to 10-membered monocyclic or bicyclic aryl group, (d) a cycloalkyl group, (e) a 6- to 10-membered monocyclic or bicyclic aryl group optionally substituted by one to two group(s) selected from a halogen atom, cyano group, an alkyl group, a trihalogenoalkyl group and an alkyloxy group, (f) an amino group optionally substituted by one or two alkyl group(s) or (g) a saturated or unsaturated 4- to 7-membered sulfur-, oxygen- or nitrogen- containing heteromonocyclic group optionally substituted by one to two group(s) selected from a halogen atom, cyano group, an alkyl group and a trihalogenoalkyl group, excluding
6-(2-chlorophenyl)-7-(4-chlorophenyl)-3-[N-(1,1-dioxotetrahydrothien-3-yl)-carbamoyl -2-(hydroxymethyl)pyrazolo[1,5-a]pyrimidine,
or a pharmaceutically acceptable salt thereof.

5. A compound of the formula [I-II-ii]:

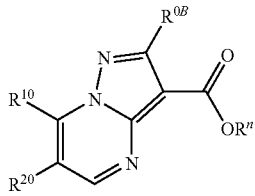

[I-II-ii]

wherein
$R^{10}$ and $R^{20}$ are the same or different and each is a phenyl group optionally substituted by one to three group(s) selected from a halogen atom, cyano group, an alkyl group optionally substituted by one to three halogen atom(s), an alkyloxy group optionally substituted by one to three halogen atom(s), an amino group optionally substituted by one to two alkyl group(s), an alkylthio group, an alkylsulfinyl group and an alkylsulfonyl group,
$R^{0B}$ is a group of the formula: —$SO_2N(R^{01})(R^{02})$, a group of the formula: —$NHCONHR^{03}$, a group of the formula: —$CON(R^e)(R^f)$, or a carboxyl group, $R^{01}$ and $R^{02}$ are the same or different and each hydrogen atom, an alkyl group or a carbamoylalkyl group, $R^{03}$ is hydrogen atom or an alkyl group, $R^e$ and $R^f$ are the same or different and each hydrogen atom, an alkyl group or a dialkylamino group and $R^n$ is an alkyl group,
or a pharmaceutically acceptable salt thereof.

6. The compound according to claim 4 in which $R^{10}$ is a phenyl group optionally substituted by one to two group(s) selected from a halogen atom, an alkyl group, a difluoroalkyl group, a trifluoroalkyl group and a dialkylamino group, $R^{20}$ is a phenyl group optionally substituted by one to two group(s) selected from a halogen atom and cyano group,
$R^{6A}$ is
(A) an alkyl group optionally substituted by a group selected from one to three halogen atom(s), hydroxyl group, cyano group, carboxyl group and an alkyloxycarbonyl group; or
(B) a group of the following formula:

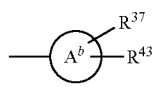

in which Ring $A^b$ is (a) a $C_{3-8}$ cycloalkyl group or (b) a $C_{3-8}$ cycloalkyl group fused to a benzene ring, $R^{37}$ is hydrogen atom, cyano group, an alkyl group, a hydroxyalkyl group, an aminoalkyl group, a carboxyalkyl group, carboxyl group, an alkyloxycarbonyl group, a carbamoyl group optionally substituted by one to two group(s) selected from an alkyl group and a dialkylamino-alkyl group, or a group of the following formula:

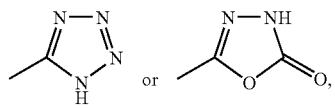

and
$R^{43}$ is hydrogen atom, amino group, an alkyloxycarbonylamino group or benzyloxy-carbonylamino group; or
(C) a phenyl group optionally substituted by one to two group(s) selected from a halogen atom, an alkyloxy group, a trihalogenoalkyl group, carboxyl group and an alkyloxycarbonyl group; or
(D) a cyclic group of the following formula:

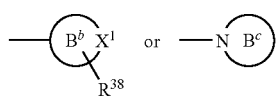

in which Ring $B^b$ is a 4- to 7-membered aliphatic heterocyclic group, said cyclic group binding via its ring-carbon atom to the adjacent nitrogen atom, Ring $B^c$ is a 4- to 7-membered nitrogen-containing aliphatic heteromonocyclic group, $X^1$ is sulfur atom, a group of the formula: —SO—, a group of the formula: —$SO_2$—, oxygen atom or a group of the formula: —$NR^m$—, $R^m$ is an alkyl group, an alkylcarbonyl group, an alkyloxycarbonyl group, an alkylsulfonyl group, an aminosulfonyl group optionally substituted by one or two alkyl group(s) or a carbamoyl group optionally substituted by one or two alkyl group(s), $R^{38}$ is (a) hydrogen atom, (b) a cyano group, (c) an alkyl group, (d) a hydroxyalkyl group, (e) an aminoalkyl group, (f) a carboxyalkyl group, (g) carboxyl group, (h) an alkyloxycarbonyl group, (i) a carbamoyl group optionally substituted by one to two group(s) selected from an alkyl group and a dialkylamino-alkyl group or (j) a group of the following formula:

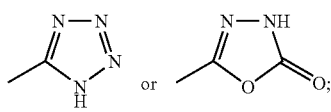

or (E) a group of the formula: —N(R^{8a})(R^{9a}) in which R^{8a} is hydrogen atom or an alkyl group, R^{9a} is an alkyl group, a trihalogenoalkyl group, a cyanoalkyl group, benzyl group, a cycloalkyl group, a phenyl group optionally substituted by a group selected from a halogen atom, cyano group, an alkyl group, a trihalogenoalkyl group, an alkyloxy group, a trihalogenoalkyloxy group, an alkylthio group, an alkylsulfonyl group, an alkyloxycarbonyl group and benzyloxycarbonyl group, an alkyloxycarbonyl group, a benzyloxycarbonyl group or a 5- to 6-membered nitrogen-containing heteroaryl group; or (F) a group of the following formula:

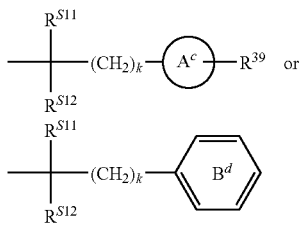

in which Ring $A^c$ is a $C_{3-8}$ cycloalkyl group optionally fused to a benzene ring, Ring $B^d$ is (a) a phenyl group optionally substituted by a halogen atom, cyano group, an alkyloxy group, a trihalogenoalkyl group or carboxyl group or (b) a pyridyl group, $R^{S11}$ is hydrogen atom or an alkyl group, $R^{S12}$ is hydrogen atom, an alkyl group, carboxyl group, carbamoyl group or a mono- or di-alkylcarbamoyl group, $R^{39}$ is hydrogen atom, a halogen atom, cyano group, an alkyl group, a hydroxyalkyl group, a trihalogenoalkyl group, an aminoalkyl group, an alkyloxy group, a carboxyalkyl group, carboxyl group, a carbamoyl group optionally substituted by one to two group(s) selected from an alkyl group and a dialkylaminoalkyl group, amino group, an alkyloxycarbonylamino group or a benzyloxycarbonylamino group, and k is an integer of 0 to 2, or a pharmaceutically acceptable salt thereof.

7. The compound according to claim 5 in which $R^{10}$ is a phenyl group optionally substituted by one to two group(s) selected from a halogen atom, an alkyl group, a difluoroalkyl group, a trifluoroalkyl group and a dialkylamino group and $R^{20}$ is a phenyl group optionally substituted by one to two group(s) selected from a halogen atom and cyano group, or a pharmaceutically acceptable salt thereof.

8. The compound according to claim 1 in which R' is a group of the formula, X is sulfur atom, a group of the formula: —SO₂—, oxygen atom or a group of the formula: —NR^k—, R^k is a $C_{1-6}$ alkyloxy-carbonyl group, a $C_{1-6}$ alkylsulfonyl group, a $C_{1-6}$ alkyl-carbonyl group or a di($C_{1-6}$ alkyl)aminosulfonyl group, $R^3$ is (a) carbamoyl group, (b) a mono- or di($C_{1-6}$ alkyl)-carbamoyl group, (c) a mono(trihalogeno-$C_{1-6}$ alkyl)carbamoyl group, (d) a $C_{1-6}$ alkyloxy-carbonyl group, (e) a $C_{1-6}$ alkyl group or (f) a hydroxy-$C_{1-6}$ alkyl group and $R^4$ is hydrogen atom, or a pharmaceutically acceptable salt thereof.

9. The compound of claim 1, which is
6-(2-chlorophenyl)-7-(4-chlorophenyl)-3-[N-(1-cyanocyclohexy)carbamoyl]-pyrazolo[1,5-a]pyrimidine;
6-(2-chlorophenyl)-7-(4-chlorophenyl)-3-[N-(1-cyanocyclopentyl)carbamoyl]-pyrazolo[1,5-a]pyrimidine;
6-(2-chlorophenyl)-7-(4-chlorophenyl)-3-[N-(1-methylcyclohexyl)carbamoyl]-pyrazolo[1,5-a]pyrimidine;
6-(2-chlorophenyl)-7-(4-chlorophenyl)-3-[N-(1-methylcyclopropyl)carbamoyl]pyrazolo[1,5-a]pyrimidine;
6-(2-chlorophenyl)-3-[N-(1-cyanocyclopentyl)carbamoyl]-7-(4-trifluoromethylphenyl)-2-methylpyrazolo[1,5-a]pyrimidine;
6-(2-chlorophenyl)-3-[N-(1-cyanocyclohexyl)carbamoyl]-7-(4-trifluoromethylphenyl)-2-methylpyrazolo[1,5-a]pyrimidine;
3-[N-(4-carbamoyl-1,1-dioxo-tetrahydrothiopyran-4-yl)carbamoyl]-6-(2-chlorophenyl) -7-(4-chlorophenyl)pyrazolo[1,5-a]pyrimidine;
2-acetylamino-6-(2-chlorophenyl)-7-(4-trifluoromethylphenyl)-3-[N-[1-(2-pyridyl)ethyl]carbamoyl]pyrazolo[1,5-a]pyrimidine;
6-(2-chlorophenyl)-7-(4-chloro-2-fluorophenyl)-3-[N-[1-(2-pyridyl)ethyl]carbamoyl]pyrazolo[1,5-a]pyrimidine;
6-(2-chlorophenyl)-7-(4-trifluoromethylphenyl)-3-[N-[1-(2-pyridyl)ethyl]carbamoyl]-2-(1-pyrrolidinyl)pyrazolo[1,5-a]pyrimidine;
3-[N-(1-carbamoylcyclohexyl)carbamoyl]-6-(2-chlorophenyl)-7-(4-chlorophenyl)pyrazolo[1,5-a]pyrimidine;
6-(2-chlorophenyl)-7-(4-chlorophenyl)-3-[N-[1-methyl-1-(2-pyridyl)ethyl]carbamoyl]pyrazolo[1,5-a]pyrimidine;
6-(2-chlorophenyl)-7-(4-trifluoromethylphenyl)-3-[N-[1-methyl-1-(2-pyridyl) -ethyl]carbamoyl]pyrazolo[1,5-a]pyrimidine;
3-[N-(4-carbamoyl-1,1-dioxo-tetrahydrothiopyran-4-yl)carbamoyl]-6-(2-chlorophenyl) -7-(4-trifluoromethylpheny)pyrazolo[1,5-a]pyrimidine;
3-[N-(1-carboxycyclohexyl)carbamoyl]-6-(2-chlorophenyl)-7-(4-chloropheny)pyrazolo[1,5-a]pyrimidine;
6-(2-chlorophenyl)-7-(4-chlorophenyl)-3-[[1-[N-[2-(N,N-dimethylamino)ethyl]carbamoyl]cyclohexyl]carbamoyl]pyrazolo[1,5-a]pyrimidine;
6-(2-chlorophenyl)-7-(4-chlorophenyl)-3-[N-[1-(N -methylcarbamoyl)cyclohexyl]carbamoyl]pyrazolo[1,5-a] pyrimidine;
6-(2-chlorophenyl)-7-(4-chlorophenyl)-3[N-[1-(N,N -dimethylcarbamoyl)cyclohexyl]carbamoyl]pyrazolo[1,5-a]pyrimidine;
(S)-3-[N-(1-carboxy-2-methylpropyl)carbamoyl]-6-(2-chlorophenyl)-7-(4-chlorophenyl)pyrazolo[1,5-a]pyrimidine;
(S)-3-[N-(1-carboxy-2-methylpropyl)carbamoyl]-6-(2-chlorophenyl)-7-(4-trifluoromethylpheny)pyrazolo[1,5-a]pyrimidine;
(S)-3-[N-(α-carboxybenzyl)carbamoyl]-6-(2-chlorophenyl)-7-(4-trifluoromethylpheny)pyrazolo[1,5-a]pyrimidine;
(S)-3-[N-(1-carboxy-2-methylpropyl)carbamoyl]-6-(2-chlorophenyl)-7-(4-chlorophenyl) -2-methylpyrazolo[1,5-a]pyrimidine;
3-[N-(1-carboxy-1-methylethyl)carbamoyl]-6-(2-chlorophenyl)-7-(4-chlorophenyl)-2-methylpyrazolo[1,5-a]pyrimidine;
3-[N-(α-carboxybenzyl)carbamoyl]-6-(2-chlorophenyl)-7-(4-chlorophenyl)pyrazolo[1,5-a]pyrimidine;

3-[N-(1-carboxy-1-methylethy)carbamoyl]-6-(2-chlorophenyl)-7-(4-trifluoromethylpheny)pyrazolo[1,5-a]pyrimidine;

3-[N-(4-carboxy-1-cyclohexyl)carbamoyl]-6-(2-chlorophenyl)-7-(4-trifluoromethylphenyl)pyrazolo[1,5-a]pyrimidine;

6-(2-chlorophenyl)-7-(4-chlorophenyl)-3-[N-[1-(2-pyridyl)ethyl]carbamoyl]pyrazolo[1,5-a]pyrimidine;

6-(2-chlorophenyl)-3-[N-(1-cyanocyclohexyl)carbamoyl]-7-(4-trifluoromethylpheny)pyrazolo[1,5-a]pyrimidine;

6-(2-chlorophenyl)-7-(4-chlorophenyl)-3[N-(1methoxycarbonylcyclohexyl)carbamoyl]pyrazolo[1,5-a]pyrimidine;

6-(2-chlorophenyl)-7-(4-chlorophenyl)-2-(methylsulfonylamino)-3-[N-[1-(2-pyridyl)ethyl]carbamoyl]pyrazolo[1,5-a]pyrimidine;

6-(2-chlorophenyl)-7-(4-chlorophenyl)-2-[N-methyl-N-(methylsulfonyl)amino]-3-[N-[1-(2-pyridyl)ethyl]carbamoyl]pyrazolo[1,5-a]pyrimidine;

6-(2-chlorophenyl)-7-(4-trifluoromethylphenyl)-3-[N-(1-methoxycarbonylcyclohexyl)sulfamoyl]-2-methylpyrazolo[1,5-a]pyrimidine;

3-[N-(1-carboxycyclohexyl)sulfamoyl]-6-(2-chlorophenyl)-7-(4-trifluoromethylphenyl) -2-methylpyrazolo[1,5-a]pyrimidine;

6-(2-chlorophenyl)-7-(4-chlorophenyl)-3-[N-(4-methoxycarbonyl-1,1-dioxo -tetrahydrothiopyran-4-yl)carbamoyl]pyrazolo[1,5-a]pyrimidine;

6-(2-chlorophenyl)-7-(4-trifluoromethylphenyl)-3-[N-(4-methyl-1,1-dioxo -tetrahydrothiopyran-4-yl)carbamoyl]pyrazolo[1,5-a]pyrimidine;

6-(2-chlorophenyl)-7-(4-chlorophenyl)-2-methyl-3[N-(4-methyl-1,1-dioxo -tetrahydrothiopyran-4-yl)carbamoyl]pyrazolo[1,5-a]pyrimidine;

6-(2-chlorophenyl)-7-(4-trifluoromethylphenyl)-2-methyl-3[N-(4-methyl-1,1-dioxo -tetrahydrothiopyran-4-yl)carbamoyl]pyrazolo[1,5-a]pyrimidine;

6-(2-chlorophenyl)-7-(4-chlorophenyl)-3-[N-(3-hydroxy-2-methylprop-2-yl)carbamoyl]-2-methylpyrazolo[1,5-a]pyrimidine;

6-(2-chlorophenyl)-7-(4-trifluoromethylphenyl)-3[N-(4-hydroxymethyl-1,1-dioxo -tetrahydrothiopyran-4-yl) carbamoyl]pyrazolo[1,5-a]pyrimidine;

6-(2-chlorophenyl)-7-(4-chlorophenyl)-2-trifluoromethyl-3[N-(4-methyl-1,1-dioxo -tetrahydrothiopyran-4-yl)carbamoyl]pyrazolo[1,5-a]pyrimidine;

6-(2-chlorophenyl)-7-(4-chlorophenyl)-2-ethoxy-3-[N-(4-methyl-1,1-dioxo -tetrahydrothiopyran-4-yl)carbamoyl]pyrazolo[1,5-a]pyrimidine;

6-(2-chlorophenyl)-7-(2-fluoro-4-trifluoromethylphenyl)-3[N-(4-methyl-1,1-dioxo -tetrahydrothiopyran-4-yl)carbamoyl]pyrazolo[1,5-a]pyrimidine;

6-(2-chlorophenyl)-7-(4-trifluoromethylphenyl)-3-[N-(3-methoxycarbonyl-1,1-dioxothietan-3-yl)carbamoyl]pyrazolo[1,5-a]pyrimidine;

6-(2-chlorophenyl)-7-(4-chlorophenyl)-3-[N-(1-cyanocyclohexyl)carbamoyl]-2-methylpyrazolo[1,5-a]pyrimidine;

6-(2-chlorophenyl)-7-(4-chlorophenyl)-2-(2-hydroxyethoxy)-3-[N-(3-methyl-1,1-dioxo -tetrahydrothien-3yl)carbamoyl]pyrazolo[1,5-a]pyrimidine;

6-(2-chlorophenyl)-7-(4-trifluoromethylphenyl)-2-(2-hydroxyethoxy)-3-[N-(3-methyl -1,1-dioxotetrahydrothien-3-yl)carbamoyl]pyrazolo[1,5-a]pyrimidine;

6-(2-chlorophenyl)-7-(4-trifluoromethylphenyl)-3-[N-(3-methyl-1,1-dioxotetrahydrothien-3-yl)carbamoyl]pyrazolo[1,5-a]pyrimidine;

6-(2-chlorophenyl)-2-(difluoromethyl)-7-(4-trifluoromethylphenyl)-3-[N-(3-methyl-1,1-dioxotetrahydrothien-3yl)carbamoyl]pyrazolo[1,5-a]pyrimidine;

6-(2-chlorophenyl)-7-(4-chlorophenyl)-2-(trifluoromethyl)-3-[N-(3-methyl-1,1-dioxotetrahydrothien-3-yl)carbamoyl]pyrazolo[1,5-a]pyrimidine;

6-(2-chlorophenyl)-7-(4-trifluoromethylphenyl)-3-[N-[4-(N-methylcarbamoyl)-1,1-dioxotetrahydrothiopyran-4-yl]carbamoyl]pyrazolo[1,5-a]pyrimidine;

6-(2-chlorophenyl)-3-[N-[4[N-(2,2,2-trifluoroethyl)carbamoyl]-1,1-dioxotetrahydrothiopyran-4-yl]carbamoyl]-7-(4-trifluoromethylphenyl)pyrazolo[1,5-a]pyrimidine; or 6-(2-chlorophenyl)-3-[N-[4-[N-(2,2,2-trifluoroethyl)carbamoyl]-1,1-dioxotetrahydrothiopyran-4-yl]carbamoyl]-7-(4-trifluoromethylphenyl)-2-methylpyrazolo[1,5-a]pyrimidine or a pharmaceutically acceptable salt thereof.

10. The compound according to claim 2 in which $R^1$ and $R^2$ are the same or different and each a phenyl group optionally substituted by one to two group(s) selected from a halogen atom, cyano group, a dihalogenoalkyl group and a trihalogenoalkyl group, $R^{OB}$ is a group of the formula: —SO$_2$N($R^{O1}$)($R^{O2}$) and R" is an alkyloxy group, or a pharmaceutically acceptable salt thereof.

11. The compound according to claim 10 in which E is a group of the formula: —C(=O)—, or a pharmaceutically acceptable salt thereof.

12. The compound according to claim 2 in which $R^1$ and $R^2$ are the same or different and each a phenyl group optionally substituted by one to two group(s) selected from a halogen atom, cyano group, an alkyl group, a dihalogenoalkyl group and a trihalogenoalkyl group, $R^{OB}$ is a group of the formula: —NHCONH$R^{O3}$, E is a group of the formula: —C(=O)—, R" is a group of the formula: —N($R^5$)($R^6$), $R^5$ is hydrogen atom, $R^6$ is (a) an alkyl group, (b) a trihalogenoalkyl group, (c) a $C_{3-8}$ cycloalkyl group, (d) a dialkylamino group or (e) a saturated or unsaturated 5- to 6-membered sulfur-containing heterocyclic group optionally substituted by one to three group(s) selected from oxo group, an alkyl group and carbamoyl group, or a pharmaceutically acceptable salt thereof.

13. The compound according to claim 2 in which $R^1$ and $R^2$ are the same or different and each is a phenyl group optionally substituted by one to two group(s) selected from a halogen atom, cyano group, an alkyl group, a dihalogenoalkyl group, a trihalogenoalkyl group and an alkyloxy group, $R^{OB}$ is a group of the formula: —SO$_2$N($R^{O1}$)($R^{O2}$) $R^{O1}$ is hydrogen atom or an alkyl group, $R^{O2}$ is hydrogen atom, an alkyl group or a carbamoylalkyl group, E is a group of the formula: —C(=O)—, R" is a group of the formula: —N($R^5$)($R^6$), $R^5$ is hydrogen atom or an alkyl group, $R^6$ is (a) an alkyl group optionally substituted by one to three group(s) selected from a halogen atom, hydroxyl group, cyano group, an alkyloxy group, a $C_{3-8}$ cycloalkyl group optionally substituted by one to two halogen atom(s), an amino group optionally substituted by one to two alkyl group(s) and a pyridyl group, (b) a $C_{3-8}$ cycloalkyl group optionally substituted by a group selected from an alkyl group and carbamoyl group, (c) an amino group optionally substituted by one to two group(s) selected from an alkyl group and a pyridyl group or (d) a saturated or unsaturated 5- to 6-membered nitrogen- or sulfur-containing heterocyclic group optionally substituted by one to three group(s) selected from oxo group, an alkyl group and carbamoyl group, or a pharmaceutically acceptable salt thereof.

14. The compound according to claim 2 in which $R^1$ and $R^2$ are the same or different and each a phenyl group optionally substituted by one to two group(s) selected from a halogen atom and a trihalogenoalkyl group, $R^{OB}$ is a group of the formula: —CON($R^e$)($R^f$), $R^e$ is hydrogen atom or an alkyl group, $R^f$ is hydrogen atom, an alkyl group or a dialkylamino group, E is a group of the formula: —C(=O)—, R" is a group of the formula: —N($R^5$)($R^6$), $R^5$ is hydrogen atom, $R^6$ is (a) an alkyl group optionally substituted by one to three halogen atom(s), (b) a $C_{3-8}$ cycloalkyl group or (c) a saturated or unsaturated 4- to 6-membered sulfur-containing heterocyclic group optionally substituted by one to three group(s) selected from oxo group and an alkyl group, or a pharmaceutically acceptable salt thereof.

15. The compound according to claim 2 in which $R^1$ and $R^2$ are the same or different and each a phenyl group optionally substituted by one to two group(s) selected from a halogen atom and a trihalogenoalkyl group, $R^{OB}$ is a hydroxyalkyl group, E is a group of the formula: —C(=O)—, R" is a group of the formula: —N($R^5$)($R^6$), $R^5$ is hydrogen atom, $R^6$ is (a) an alkyl group optionally substituted by one to three halogen atom(s), (b) a alkyl group substituted by a pyridyl group, (c) a $C_{3-8}$ cycloalkyl group optionally substituted by a group selected from cyano group and carbamoyl group or (d) a saturated or unsaturated 4- to 6-membered nitrogen-or sulfur-containing heterocyclic group optionally substituted by one to three group(s) selected from oxo group and an alkyl group,
  excluding 6-(2-chlorophenyl)-7-(4-chlorophenyl)-3-[N-(1,1-dioxo-tetrahydrothien-3-yl)carbamoyl]-2-(hydroxymethyl)pyrazolo[1,5-a]pyrimidine,
  or a pharmaceutically acceptable salt thereof.

16. The compound according to claim 2 in which $R^1$ and $R^2$ are the same or different and each a phenyl group optionally substituted by one to two group(s) selected from a halogen atom and a trihalogenoalkyl group, $R^{OB}$ is carboxyl group, E is a group of the formula: —C(=O)—, R" is a group of the formula: —N($R^5$)($R^6$), $R^5$ is hydrogen atom, $R^6$ is a saturated or unsaturated 5- to 6-membered sulfur-containing heterocyclic group optionally substituted by one to three group(s) selected from oxo group and an alkyl group, or a pharmaceutically acceptable salt thereof.

17. The compound according to claim 2 in which $R^1$ and $R^2$ are the same or different and each a halogenophenyl group, $R^{OB}$ is a sulfamoyl group optionally substituted by one to two alkyl group(s), E is a group of the formula: —C(=O)—, R" is an alkyloxy group, or a pharmaceutically acceptable salt thereof.

18. The compound according to claim 13 in which $R^1$ is a phenyl group optionally substituted by one to two group(s) selected from a halogen atom, a $C_{1-6}$ alkyl group, a dihalogeno-$C_{1-6}$ alkyl group and a trihalogeno-$C_{1-6}$ alkyl group, $R^2$ is a phenyl group optionally substituted by one to two group(s) selected from a halogen atom and cyano group, $R^{OB}$ is a group of the formula: —SO$_2$N($R^{O1}$)($R^{O2}$), $R^{O1}$ is hydrogen atom or a $C_{1-6}$ alkyl group, $R^{O2}$ is hydrogen atom, a $C_{1-6}$ alkyl group or a carbamoyl-$C_{1-6}$ alkyl group, $R^5$ is hydrogen atom, $R^6$ is (a) a $C_{1-6}$ alkyl group optionally substituted by one to three group(s) selected from a halogen atom, a $C_{1-6}$ alkyloxy group, a $C_{3-8}$ cycloalkyl group and a pyridyl group, (b) a $C_{3-8}$ cycloalkyl group optionally substituted by a $C_{1-6}$ alkyl group, (c) an amino group optionally substituted by one to two group(s) selected from a $C_{1-6}$ alkyl group and a pyridyl group or (d) a saturated or unsaturated 5- to 6-membered nitrogen- or sulfur-containing heterocyclic group optionally substituted by one to two oxo group(s), or a pharmaceutically acceptable salt thereof.

19. The compound according to claim 14 in which $R^1$ is a trihalogeno-$C_{1-6}$ alkyl-phenyl group, $R^2$ is a halogenophenyl group, $R^{OB}$ is a group of the formula: —CON($R^e$)($R^f$), $R^e$ is hydrogen atom or a $C_{1-6}$ alkyl group, $R^f$ is hydrogen atom or a $C_{1-6}$ alkyl group, $R^5$ is hydrogen atom, $R^6$ is (a) $C_{1-6}$ alkyl group optionally substituted by one to three halogen atom(s) or (b) a saturated or unsaturated 5- to 6-membered sulfur-containing heterocyclic group optionally substituted by one to three group(s) selected from oxo group and a $C_{1-6}$ alkyl group, or a pharmaceutically acceptable salt thereof.

20. The compound according to claim 15 in which $R^1$ is a trihalogeno-$C_{1-6}$ alkyl-phenyl group, $R^2$ is a halogenophenyl group, $R^{OB}$ is a hydroxy-$C_{1-6}$ alkyl group, $R^5$ is hydrogen atom, $R^6$ is (a) a trihalogeno-$C_{1-6}$ alkyl group, (b) a pyridyl-$C_{1-6}$ alkyl group, (c) a $C_{5-7}$ cycloalkyl group substituted by a group selected from cyano group and carbamoyl group or (d) a saturated or unsaturated 5- to 6-membered sulfur-containing heterocyclic group optionally substituted by one to three group(s) selected from oxo group and a $C_{1-6}$ alkyl group, excluding
  6-(2-chlorophenyl)-7-(4-chlorophenyl)-3-[N-(1,1-dioxo-tetrahydrothien-3-yl)carbamoyl]-2-(hydroxymethyl) pyrazolo[1,5-a]pyrimidine,
  or a pharmaceutically acceptable salt thereof.

21. The compound according to claim 17 in which $R^1$ and $R^2$ are the same or different and each a halogenophenyl group, $R^{OB}$ is a $C_{1-6}$ alkyl-sulfamoyl group and R" is a $C_{1-6}$ alkyloxy group,
  or a pharmaceutically acceptable salt thereof.

22. The compound of claim 2, which is
  (R)-6-(2-chlorophenyl)-7-(4-chlorophenyl)-2-(N-methylsulfamoyl)-3-[N-(1,1-dioxotetrahydrothien-3-yl)carbamoyl]pyrazolo[1,5-a]pyrimidine;
  6-(2-chlorophenyl)-7-(4-chlorophenyl)-3[N-(cyclopenty)carbamoyl]-2-(N -methylsulfamoy)pyrazolo[1,5-a]pyrimidine;
  6-(2-chlorophenyl)-7-(4-chlorophenyl)-3-[[N'-methyl-N'-(2-pyridyl)hydrazino]carbonyl]-2-(N-methylsulfamoyl)pyrazolo[1,5-a]pyrimidine;
  (R)-6-(2-chlorophenyl)-7-(4-chlorophenyl)-2-(N,N-dimethylsulfamoyl)-3-[N-(1,1-dioxotetrahydrothien-3-yl)carbamoyl]pyrazolo[1,5-a]pyrimidine;
  6-(2-chlorophenyl)-7-(4-chlorophenyl)-3-[N-(cyclopentyl)carbamoyl]-2-(N,N -dimethylsulfamoyl)pyrazolo[1,5-a]pyrimidine;
  6-(2-chlorophenyl)-7-(4-chlorophenyl)-2-(N,N-dimethylsulfamoyl)-3-[N-(1-pynolidinyl)carbamoyl]pyrazolo[1,5-a]pyrimidine;
  6-(2-chlorophenyl)-7-(4-chlorophenyl)-3-[[N'-methyl-N'-(2-pyridyl)hydrazino]carbonyl]-2-(N,N-dimethylsulfamoyl)pyrazolo[1,5-a]pyrimidine;
  6-(2-chlorophenyl)-7-(4-chlorophenyl)-2-(N-methylsulfamoyl)-3-[N-(1-pyrrolidinyl)carbamoyl]pyrazolo[1,5-a]pyrimidine;
  (R)-6-(2-chlorophenyl)-7-(4-chlorophenyl)-3-[N-(1,1-dioxotetrahydrothien-3-yl)carbamoyl]-2-sulfamoylpyrazolo[1,5-a]pyrimidine;
  6-(2-chlorophenyl)-7-(4-chlorophenyl)-3-[N-(1-pyrrolidinyl)carbamoyl]-2-sulfamoylpyrazolo[1,5-a]pyrimidine;
  6-(2-chlorophenyl)-7-(4-chlorophenyl)-3-[[N'-methyl-N'-(2-pyridyl)hydrazino]carbonyl]-2-sulfamoylpyrazolo[1,5-a]pyrimidine;

(S)-6-(2-chlorophenyl)-7-(4-chlorophenyl)-3-[N-(1,1-dioxotetrahydrothien-3-yl)carbamoyl]-2-sulfamoylpyrazolo[1,5-a]pyrimidine;

6-(2-chlorophenyl)-7-(4-chlorophenyl)-3-[N-(cyclopentyl)carbamoyl]-2-sulfamoylpyrazolo[1,5-a]pyrimidine;

6-(2-chlorophenyl)-7-(4-chlorophenyl)-3-[N-(1,1-dioxotetrahydrothiopyran-4-yl)carbamoyl]-2-sulfamoylpyrazolo[1,5-a]pyrimidine;

(R)-6-(2-chlorophenyl)-7-(4-trifluoromethylphenyl)-3-[N-(1,1-dioxotetrahydrothien-3-yl)carbamoyl]-2-sulfamoylpyrazolo[1,5-a]pyrimidine;

(S)-6-(2-chlorophenyl)-7-(4-trifluoromethylphenyl)-3-[N-(1,1-dioxotetrahydrothien-3-yl)carbamoyl]-2-sulfamoylpyrazolo[1,5-a]pyrimidine;

6-(2-chlorophenyl)-3-[N-(cyclopentyl)carbamoyl]-7-(4-trifluoromethylphenyl)-2-sulfamoylpyrazolo[1,5-a]pyrimidine;

(R)-7-(4-chlorophenyl)-6-(2-cyanophenyl)-3-[N-(1,1-dioxotetrahydrothien-3-yl)carbamoyl]-2-sulfamoylpyrazolo[1,5-a]pyrimidine;

7-(4-chlorophenyl)-6-(2-cyanophenyl)-3-[N-(cyclopentyl)carbamoyl]-2-sulfamoylpyrazolo[1,5-a]pyrimidine;

7-(4-chlorophenyl)-6-(2-cyanophenyl)-3-[[N'-methyl-N'-(2-pyridyl)hydrazino]carbonyl]-2-sulfamoylpyrazolo[1,5-a]pyrimidine;

(R)-2-[N-(carbamoylmethyl)sulfamoyl]-6-(2-chlorophenyl)-7-(4-chlorophenyl)-3-[N -(1,1-dioxotetrahydrothien-3-yl)carbamoyl]pyrazolo[1,5-a]pyrimidine;

2-[N-(carbamoylmethyl)sulfamoyl]-6-(2-chlorophenyl)-7-(4-chlorophenyl)-3-[N -(cyclopentyl)carbamoyl]pyrazolo[1,5-a]pyrimidine;

2-[N-(carbamoylmethyl)sulfamoyl]-6-(2-chlorophenyl)-7-(4-chlorophenyl)-3-[[N'-methyl-N'-(2-pyridyl)hydrazino]carbonyl]pyrazolo[1,5-a]pyrimidine;

2-[N-(carbamoylmethyl)sulfamoyl]-6-(2-chlorophenyl)-7-(4-chlorophenyl)-3-[N-(1-pyrrolidlinyl)carbamoyl]pyrazolo[1,5-a]pyrimidine;

3-[N-(1-carboxycyclohexyl)carbamoyl]-6-(2-chlorophenyl)-7-(4-chlorophenyl)-2-(N -methylsulfamoyl)pyrazolo[1,5-a]pyrimidine;

3-[N-(1-carbamoylcyclohexyl)carbamoyl]-6-(2-chlorophenyl)-7-(4-chlorophenyl)-2-sulfamoylpyrazolo[1,5-a]pyrimidine;

6-(2-chlorophenyl)-7-(4-trifluoromethylphenyl)-2-hydroxymethyl-3-[N-[1-methyl-1-(2-pyridyl)ethyl]carbamoyl]pyrazolo[1,5-a]pyrimidine;

6-(2-chlorophenyl)-7-(4-trifluoromethylphenyl)-2-hydroxymethyl-3-[N-(3-methyl-1,1-dioxotetrahydrothien-3-yl)carbamoyl]pyrazolo[1,5-a]pyrimidine;

6-(2-chlorophenyl)-3-[N-(1-cyanocyclohexyl)carbamoyl]-7-(4-trifluoromethylphenyl)-2-(hydroxymethyl)pyrazolo[1,5-a]pyrimidine;

6-(2-chlorophenyl)-7-(4-trifluoromethylphenyl)-2-hydroxymethyl-3-[N-(4-methyl-1,1-dioxotetrahydrothiopyran-4-yl)carbamoyl]pyrazolo[1,5-a]pyrimidine;

2-carbamoyl-6-(2-chlorophenyl)-7-(4-trifluoromethylphenyl)-3-[N-(4-methyl-1,1-dioxotetrahydrothiopyran-4-yl)carbamoyl]pyrazolo[1,5-a]pyrimidine;

6-(2-chlorophenyl)-7-(4-trifluoromethylphenyl)-2-(N-methylcarbamoyl)-3-[N-(4-methyl -1,1-dioxotetrahydrothiopyran-4-yl)carbamoyl]pyrazolo[1,5-a]pyrimidine;

6-(2-chlorophenyl)-7-(4-chlorophenyl)-3-[N-(2,2-dimethylpropyl)carbamoyl]-2-sulfamoylpyrazolo[1,5-a]pyrimidine;

6-(2-chlorophenyl)-7-(4-chlorophenyl)-3-[N-(cyclohexylmethyl)carbamoyl]-2-sulfamoylpyrazolo[1,5-a]pyrimidine;

6-(2-chlorophenyl)-7-(4-chlorophenyl)-3-[N-(2,2,2-trifluoroethyp)carbamoyl]-2-sulfamoylpyrazolo[1,5-a]pyrimidine;

6-(2-chlorophenyl)-7-(4-chlorophenyl)-3-[N-(3-methylpropyl)carbamoyl]-2-sulfamoylpyrazolo[1,5-a]pyrimidine;

6-(2-chlorophenyl)-7-(4-chlorophenyl)-3-[N-(2,2-difluoroethyl)carbamoyl]-2-sulfamoylpyrazolo[1,5-a]pyrimidine;

6-(2-chlorophenyl)-7-(4-chlorophenyl)-3-[N-(cyclopropylmethyl)carbamoyl]-2-sulfamoylpyrazolo[1,5-a]pyrimidine;

6-(2-chlorophenyl)-7-(4-chlorophenyl)-3-[N-(1-methylcyclopropyl)carbamoyl]-2-sulfamoylpyrazolo[1,5-a]pyrimidine;

6-(2-chlorophenyl)-3-[N-(2,2,2-trifluoroethyl)carbamoyl]-7-(4-trifluoromethylphenyl)-2-(hydroxymethyl)pyrazolo[1,5-a]pyrimidine;

6-(2-chlorophenyl)-7-(4-difluoromethylphenyl)-3-[N-(isobutyl)carbamoyl]-2-sulfamoylpyrazolo[1,5-a]pyrimidine;

2-carbamoyl-6-(2-chlorophenyl)-3-[N-(2,2,2-trifluoroethyl)carbamoyl]-7-(4-trifluoromethylphenyl)pyrazolo[1,5-a]pyrimidine;

6-(2-chlorophenyl)-7-(4-chloro-2-fluorophenyl)-3-[N-(2,2,2-trifluoroethyl)carbamoyl]-2-sulfamoylpyrazolo[1,5-a]pyrimidine;

6-(2-chlorophenyl)-7-(4-difluoromethylphenyl)-3-[N-(2,2,2-trifluoroethyl)carbamoyl]-2-sulfamoylpyrazolo[1,5-a]pyrimidine;

6-(2-chlorophenyl)-7-(4-trifluoromethylphenyl)-3-[N-(n-propyl)carbamoyl]-2-sulfamoylpyrazolo[1,5-a]pyrimidine;

6-(2-chlorophenyl)-7-(4-trifluoromethylphenyl)-3-[N-(isobutyl)carbamoyl]-2-sulfamoylpyrazolo[1,5-a]pyrimidine;

6-(2-chlorophenyl)-7-(4-trifluoromethylphenyl)-3-[N-(1-methylpropyl)carbamoyl]-2-sulfamoylpyrazolo[1,5-a]pyrimidine;

6-(2-chlorophenyl)-7-(4-trifluoromethylphenyl)-3-[N-(3-methoxyprop-2-yl)carbamoyl]-2-sulfamoylpyrazolo[1,5-a]pyrimidine;

6-(2-chlorophenyl)-7-(4-trifluoromethylphenyl)-3-[N-(1-methylcyclopropyl)carbamoyl]-2-sulfamoylpyrazolo[1,5-a]pyrimidine;

6-(2-chlorophenyl)-3-[N-(2,2,2-trifluoroethyl)carbamoyl]-7-(4-fluorophenyl)-2-sulfamoylpyrazolo[1,5-a]pyrimidine;

6-(2-chlorophenyl)-7-(4-trifluoromethylphenyl)-3-[[N'-methyl-N'-(2-pyridyl)hydrazino]carbonyl]-2-sulfamoylpyrazolo[1,5-a]pyrimidine;

6-(2-chlorophenyl)-7-(4-trifluoromethylphenyl)-3-[N-(2,2,2-trifluoroethyl)carbamoyl]-2-(dimethylcarbamoyppyrazolo[1,5-a]pyrimidine;

6-(2-chlorophenyl)-7-(4-trifluoromethylphenyl)-3-[N-[1-methyl-1-(2-pyridyl)ethyl]carbamoyl]-2-sulfamoylpyrazolo[1,5-a]pyrimidine;

6-(2-chlorophenyl)-3-[N-(3-methoxyprop-2-yl)carbamoyl]-7-(4-methylphenyl)-2-sulfamoylpyrazolo[1,5-a]pyrimidine;

6-(2-chlorophenyl)-3-[N-(2,2,2-trifluoroethyl)carbamoyl]-7-(4-methylphenyl)-2-sulfamoylpyrazolo[1,5-a]pyrimidine;

6-(2-chlorophenyl)-3-[N-(isobutyl)carbamoyl]-7-(4-methylphenyl)-2-sulfamoylpyrazolo[1,5-a]pyrimidine; or 6-(2-chlorophenyl)-3-[N-(cyclopentyl)carbamoyl]-7-(4-methylphenyl)-2-sulfamoylpyrazolo[1,5-a]pyrimidine; or a pharmaceutically acceptable salt thereof.

23. A pharmaceutical composition comprising as an active ingredient a compound of the formula:

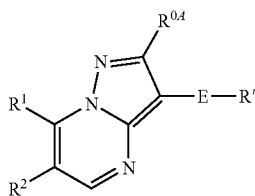

[I-I]

wherein
R$^1$ and R$^2$ are the same or different and each is a phenyl groups optionally substituted by 1 to 3 substituents selected from the group consisting of halogen atoms, cyano groups, alkyl groups optionally substituted by 1 to 3 halogen atoms, and an amino group optionally substituted by 1 or 2 alkyl groups, R$^{OA}$ is (a) a hydrogen atom, (b) an alkyl group optionally substituted by 1 to 3 halogen atoms, (c) an alkyloxy group optionally substituted by a hydroxyl group, (d) a hydroxyalkyl group, (e) an amino group substituted by 1 to 2 groups selected from the group consisting of alkyl groups, alkyl carbonyl groups, and alkylsulfonyl groups, or (f) a 4- to 6-membered nitrogen-containing aliphatic heterocyclic group, E is a group of the formula: —C(=O)— or —SO$_2$—, R' is a group of the following formula [i], [ii] or [iii]:

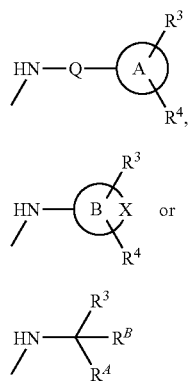

in which Ring A is (a) a C$_{3-8}$ cycloalkyl group optionally fused to a benzene ring or (b) a benzene ring, Q is a single bond or a methylene group, Ring B is a 4- to 7-membered aliphatic heterocyclic group, said cyclic group binding via its ring-carbon atom to the adjacent nitrogen atom, A1) provided that if R' is a group of the formula, then R$^3$ is (a) an alkyl group optionally substituted by a group selected from hydroxyl group and amino group, (b) a cyano group, (c) a carboxyl group, (d) an alkyloxycarbonyl group, (e) —CON(R$^e$)(R$^f$) wherein R$^e$ and R$^f$ are the same or different and each is a hydrogen atom, an alkyl group, or a dialkylaminoalkyl group, or (f) an acylamino group, and R$^4$ is hydrogen atom or an acylamino group; A2) provided that if R' is a group of the formula, then X is sulfur atom, a group of the formula: —SO$_2$—, an oxygen atom, or a group of the formula: —NR$^k$— in which R$^k$ is an alkyloxycarbonyl group, an alkylsulfonyl group, an alkylcarbonyl group, or a dialkylaminosulfonyl group, R$^3$ is (a) an alkyl group optionally substituted by a hydroxyl group, (b) a carboxyl group, (c) an alkyloxycarbonyl group, or (d) a group of the formula: —CON(R$^e$)(R$^f$) in which R$^e$ and R$^f$ are the same or different and each is a hydrogen atom, an alkyl group, or a trihalogenoalkyl group, and R$^4$ is hydrogen atom; or A3) provided that if R' is a group of the formula [iii], then R$^4$ is (a) an alkyl group optionally substituted by a hydroxyl group, (b) a phenyl group optionally substituted by a halogen atom or a trihalogenoalkyl group, or (c) a 5- to 6-membered nitrogen-containing heteroaryl group, R$^B$ is hydrogen atom or an alkyl group, R$^3$ is an alkyl group, a carboxyl group, or a group of the formula: —CON(R$^a$)(R$^b$) in which R$^a$ and R$^b$ are the same or different and each is a hydrogen atom or an alkyl group, excluding 6-phenyl-7-(4-chlorophenyl)-3-(N-isopropylcarbamoyl) pyrazolo[1,5-a]pyrimidine;

6-(2-chlorophenyl)-7-(4-chloro-phenyl)-3-(N-isopropylcarbamoyl)pyrazolo[1,5-a]pyrimidine;

6-(2-chlorophenyl)-7-(4-chlorophenyl)-3-[N-(α-dimethylbenzyl)carbamoyl]-pyrazolo[1,5-a]pyrimidine;

6-(2-chlorophenyl)-7-(4-chlorophenyl)-3-[N-(α-methylbenzyl)carbamoyl]pyrazolo[1,5-a]pyrimidine;

6-(2-chlorophenyl)-7-(4-chlorophenyl)-3-[N-[1-(2-pyridyl)ethyl]carbamoyl]pyrazolo[1,5-a]pyrimidine;

6-(2-chlorophenyl)-7-(4-trifluoromethylphenyl)-3-[N-[1-(2-pyridyl)ethyl]carbamoyl]-pyrazolo[1,5-a]pyrimidine; and 6-(2-chlorophenyl)-7-(4-chlorophenyl)-3-[N-(4-cyanobenzyl)carbamoyl]-pyrazolo[1,5-a]pyrimidine, or a pharmaceutically acceptable salt thereof.

24. A pharmaceutical composition comprising as an active ingredient a compound of the formula [I-II]:

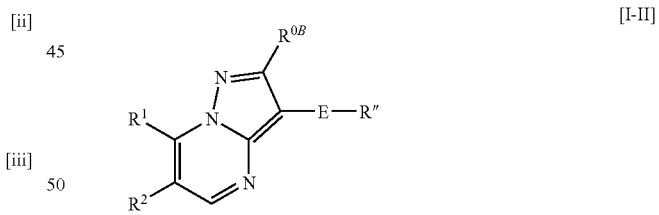

[I-II]

wherein
R$^1$ and R$^2$ are the same or different and each is a phenyl group optionally substituted by 1 to 2 substituents selected from the group consisting of halogen atoms, cyano groups, alkyl groups, dihalogenoalkyl groups, and trihalogenoalkyl groups, R$^{OB}$ is a group of the formula: —SO$_2$N(R$^{O1}$)(R$^{O2}$); a group of the formula: —NHCONHR$^{O3}$; a group of the formula: —CON(R$^e$)(R$^f$); carboxyl group; or a hydroxyalkyl group, R$^{O1}$ and R$^{O2}$ are the same or different and each hydrogen atom, an alkyl group or a carbamoylalkyl group, R$^{O3}$ is hydrogen atom or an alkyl group, R$^e$ and R$^f$ are the same or different and each hydrogen atom, an alkyl group or a dialkylamino group, E is a group of the formula: —C(=O)— or —SO$_2$—, R" is a group of the formula: —N(R$^5$)(R$^6$), R$^5$ is a hydrogen atom or an alkyl group, and R$^6$ is (a) an alkyl group optionally substituted by 1 to 3 substituents selected from the group consisting of halogen atoms, hydroxyl groups, cyano groups, alkyloxy groups, C$_{3-8}$ cycloalkyl groups, hydroxy-C$_{3-8}$ cycloalkyl groups, amino-C$_{3-8}$ cycloalkyl groups, C$_{3-8}$ cycloalkyl groups substituted by 1 or 2 halogen atoms, dialkylamino groups, carboxyl groups, carbamoyl groups optionally substituted by 1 or 2 alkyl groups, a phenyl group optionally substituted by 1 or 2 halogen atoms, trihalogenoalkyl-phenyl groups, alkyloxyphenyl groups, carboxyphenyl groups, and a saturated or unsaturated 5- to 6-membered nitrogen- or oxygen-containing heterocyclic group, (b) a C$_{3-8}$ cycloalkyl group, said cycloalkyl group being optionally fused to a benzene ring and optionally substituted by 1 to 2 groups selected from cyano groups, alkyl groups, hydroxyalkyl groups, carboxyalkyl groups, aminoalkyl groups, alkylcarbonylamino-alkyl groups, dialkylcarbamoylamino-alkyl groups, alkylsulfonylamino-alkyl groups, dialkylsulfamoylamino-alkyl groups, carboxyl groups, alkyloxycarbonyl groups, phenylalkyloxycarbonyl groups, a group of the formula: —CON(R$^{a1}$)(R$^{b1}$) in which R$^{a1}$ and R$^{b1}$ are the same or different and each is a hydrogen atom, an alkyl group, or a dialkylamino-alkyl group, and a tetrazolyl group, (c) a saturated or unsaturated 4- to 6-membered nitrogen-, sulfur- or oxygen-containing heterocyclic group optionally substituted by 1 to 3 groups selected from oxo groups, hydroxy groups, cyano groups, alkyl groups, hydroxyalkyl groups, carboxyl groups, alkyloxycarbonyl groups, alkylsulfonyl groups, a group of the formula: —CON(R$^{a2}$)(R$^{b2}$) in which R$^{a2}$ and R$^{b2}$ are the same or different and each is a hydrogen atom, an alkyl group, a trihalogenoalkyl group, a cyanoalkyl group, a hydroxyalkyl group, an alkyloxyalkyl group, an alkylsulfonyl group, or a C$_{3-8}$ cycloalkyl group, a pyrrolidinylcarbonyl group, and a morpholinocarbonyl group, or (d) an amino group optionally substituted by 1 to 2 groups selected from the group consisting of an alkyl group and a pyridyl group, excluding 6-(2-chlorophenyl)-7-(4-chlorophenyl)-3-[N-(1,1-dioxotetrahydrothien-3-yl)carbamoyl]-2-(hydroxymethyl) pyrazolo[1,5-a]pyrimidine, or a pharmaceutically acceptable salt thereof.

25. The compound of claim 1, which is

3-[N-(4-carbamoyl-1,1-dioxo-tetrahydrothiopyran-4-yl) carbamoyl]-6-(2-chlorophenyl) -7-(4-chlorophenyl) pyrazolo[1,5-a]pyrimidine or a pharmaceutically acceptable salt thereof.

26. A compound which is 6-(2-chlorophenyl)-7-(4-chlorophenyl)-3-[N-(1-cyanocyclopentyl)carbamoyl]-pyrazolo[1,5-a]-pyrimidine or a pharmaceutically acceptable salt thereof.

27. A compound which is 6-(2-chlorophenyl)-7-(4-chlorophenyl)-3-[N-(1-methylcyclohexyl)carbamoyl]-pyrazolo[1,5-a]-pyrimidine or a pharmaceutically acceptable salt thereof.

28. A compound which is

3-[N-(4-carbamoyl-1,1-dioxo-tetrahydrothiopyran-4-yl) carbamoyl]-6-(2-chlorophenyl) -7-(4-trifluoromethylphenyl)pyrazolo[1,5-a]pyrimidine or a pharmaceutically acceptable salt thereof.

29. The compound of claim 3, which is (S)-3-[N-(1-carboxy-2-phenylethyl)carbamoyl]-6-(2-chlorophenyl)-7-(4-trifluoromethylphenyl)pyrazolo[1,5-a]pyrimidine;

3-[N-(1-carboxy-2-phenylethyl)carbamoyl]-6-(2-chlorophenyl)-7-(4-chlorophenyl)pyrazolo[1,5-a]pyrimidine;

3-[N-(4-carboxybenzyl)carbamoyl]-6-(2-chlorophenyl)-7-(4-trifluoromethylphenyl)pyrazolo[1,5-a]pyrimidine; or 3-[N-(3-carboxybenzyl)carbamoyl]-6-(2-chlorophenyl)-7-(4-trifluoromethylphenyl)pyrazolo[1,5-a]pyrimidine;

or a pharmaceutically acceptable salt thereof.

30. The compound of claim 5, which is 6-(2-chlorophenyl)-7-(4-chlorophenyl)-3-ethoxycarbonyl-2-(N-methylsulfamoyl)pyrazolo[1,5-a]pyrimidine; or 6-(2-chlorophenyl)-7-(4-chlorophenyl)-3-ethoxycarbonyl-2-(N,N-dimethylsulfamoyl)pyrazolo[1,5-a]pyrimidine;

or a pharmaceutically acceptable salt thereof.

* * * * *